United States Patent
Khatri et al.

(10) Patent No.: US 11,274,345 B2
(45) Date of Patent: Mar. 15, 2022

(54) METHODS FOR DIAGNOSIS OF BACTERIAL AND VIRAL INFECTIONS

(71) Applicant: The Board of Trustees of the Leland Stanford Junior University, Stanford, CA (US)

(72) Inventors: Purvesh Khatri, Menlo Park, CA (US); Timothy E. Sweeney, San Francisco, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 335 days.

(21) Appl. No.: 16/096,261

(22) PCT Filed: Jun. 5, 2017

(86) PCT No.: PCT/US2017/036003
§ 371 (c)(1),
(2) Date: Oct. 24, 2018

(87) PCT Pub. No.: WO2017/214061
PCT Pub. Date: Dec. 14, 2017

(65) Prior Publication Data
US 2019/0144943 A1 May 16, 2019

Related U.S. Application Data

(60) Provisional application No. 62/346,962, filed on Jun. 7, 2016.

(51) Int. Cl.
*C12Q 1/68* (2018.01)
*C12Q 1/6883* (2018.01)
*C12Q 1/689* (2018.01)
*C12Q 1/70* (2006.01)

(52) U.S. Cl.
CPC ........... *C12Q 1/6883* (2013.01); *C12Q 1/689* (2013.01); *C12Q 1/701* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2004/0038201 A1 | 2/2004 | Nau et al. |
| 2011/0275542 A1 | 11/2011 | Eden et al. |
| 2012/0053073 A1 | 3/2012 | Kassis |
| 2015/0017630 A1* | 1/2015 | Oved ................... G01N 27/447 435/5 |

FOREIGN PATENT DOCUMENTS

| | | |
|---|---|---|
| CN | 103119444 A | 5/2013 |
| CN | 104204803 A | 12/2014 |
| CN | 104487593 A | 4/2015 |
| CN | 105247075 A | 1/2016 |
| CN | 105531590 A | 4/2016 |
| JP | 2015510122 A | 4/2015 |
| KR | 20090023360 A | 3/2009 |
| WO | WO 2007/059119 A2 | 5/2007 |
| WO | WO 2013/162651 A1 | 10/2013 |
| WO | WO 2015/155517 A1 | 10/2015 |

OTHER PUBLICATIONS

Handbook of Chemistry and Physics, 49th Edition, 1968, Weast (ed.), The Chemical Rubber Co., Cleveland, Ohio, p. 245.*
Ramirez et al. Differential Responses to Rhinovirus- and Influenza-associated Pulmonary Exacerbations in Patients with Cystic Fibrosis. Ann Am Thorac Soc; 2014; 11; 4: 554-561. (Year: 2014).*
Berghe et al. Regulated necrosis: the expanding network of non-apoptotic cell death pathways. Nat. Rev. Mol. Cell Biol.; 2014; 15: 135-147. (Year: 2014).*
Tolfvenstam et al. Characterization of early host responses in adults with dengue disease. BMC Infect. Dis. ; 2011;11; 209: p. 1-7. (Year: 2011).*
Sweeney et al. A comprehensive time-course-based multicohort analysis of sepsis and sterile inflammation reveals a robust diagnostic gene set. Science Translational Medicine; May 7, 2015; 287: p. 1-16. (Year: 2015).*
Sweeney et al. Science Translational Medicine, May 7, 2015, 287, p. 1-16. (Year: 2015).*
Ramirez et al. Ann Am Thorac Soc, 2014, 11, 4, 554-561. (Year: 2014).*
Berghe et al. Nat. Rev. Mol. Cell Biol., 2014, 15, 135-147. (Year: 2014).*
Tolfvenstam et al. BMC Infect. Dis., 2011, 11, 207, p. 1-7. (Year: 2011).*
Hu et al., "Gene expression profiles in febrile children with defined viral and bacterial infection", PNAS, 2013, 110(31): 12792-12797.
McHugh et al., "A Molecular Host Response Assay to Discriminate Between Sepsis and Infection-Negative Systemic Inflammation in Critically Ill Patients: Discovery and Validation in Independent Cohorts", PLOS Med, 2015, 12(12): e1001916. doi:10.1371/journal.pmed.1001916.
Scicluna et al., "A Molecular Biomarker to Diagnose Community-acquired Pneumonia on Intensive Care Unit Admission", American Journal of Respiratory and Critical Care Medicine, 2015, 192(7): 826-835.
Suarez et al., "Superiority of Transcriptional Profiling Over Procalcitonin for Distinguishing Bacterial From Viral Lower Respiratory Tract Infections in Hospitalized Adults", Transcriptional Profiles for Diagnosis of LRTI, JID, 2015, 212:213-222.
Tsalik et al., "Host gene expression classifiers diagnose acute respiratory illness etiology", Sci Transl Med., 2016, 8 (322): 322ra11. doi:10.1126/scitranslmed.aad6873.

(Continued)

*Primary Examiner* — Juliet C Switzer
*Assistant Examiner* — Wahwah T Johnson
(74) *Attorney, Agent, or Firm* — James S. Keddie; Bozicevic, Field & Francis LLP

(57) ABSTRACT

Methods for diagnosis of bacterial and viral infections are disclosed. In particular, the invention relates to the use of biomarkers that can determine whether a patient with acute inflammation has a bacterial or viral infection.

9 Claims, 39 Drawing Sheets

(56) References Cited

OTHER PUBLICATIONS

Zaas et al., "A Host-Based RT-PCR Gene Expression Signature to Identify Acute Respiratory Viral Infection", Sci Transl Med., 2013, 5(203): 203ra126. doi:10.1126/scitranslmed.3006280.

Madsen-Bouterse et al., "Original Article: The Transcriptome of the Fetal Inflammatory Response Syndrome : Cord Bloode Leukocyte Transcriptome in FIRS", American Journal of Reproductive Immunology, 2010, 63(1):73-92.

Sweeney et al.,"A comprehensive time-course Based multicohort analysis of sepsis and sterile inflammation reveals a robust diagnostic gene set", Science Translational Medicine, 2015, 7(287):287ra71.

Sweeney et al., "Robust classification of bacterial and viral infections via integrated host gene expression diagnostics", Science Translational Medicine, 2016, 8(346):346ra91.

\* cited by examiner

|  |  | Predicted | | |
|---|---|---|---|---|
|  |  | Non-infected | bacterial | viral |
| Ground Truth | Non-infected | 137 | 115 | 67 |
|  | bacterial | 19 | 504 | 13 |
|  | viral | 1 | 94 | 107 |

FIG. 3C

| Organism Type | Count |
|---|---|
| Bacillus sp. | 1 |
| Bacteroides | 1 |
| E. coli | 6 |
| Enterobacter cloacae | 3 |
| Enterococcus faecalis | 2 |
| Gram negative rods | 5 |
| Gram positive cocci | 1 |
| Group A streptococcus | 2 |
| Group B streptococcus | 3 |
| H. influenzae | 1 |
| Klebsiella oxytoca | 1 |
| Klebsiella pneumoniae | 6 |
| Moraxella catarrhalis | 2 |
| Neisseria meningitidis | 3 |
| Pneumococcus | 4 |
| Pseudomonas | 3 |
| Staph aureus | 5 |
| Enterovirus | 1 |
| Metapneumovirus | 1 |
| Influenza A | 4 |
| Influenza A (H1N1) | 1 |
| Respiratory syncytial virus | 1 |
| Rhinovirus | 1 |
| West Nile Virus | 1 |

FIG. 4A

|  | Predicted | | |
|---|---|---|---|
| | Non-infected | bact | viral |
| Ground Truth — Non-infected | 22 | 13 | 1 |
| Ground Truth — bact | 3 | 44 | 2 |
| Ground Truth — viral | 2 | 3 | 6 |

FIG. 4E

| | N bacterial | N viral | Mean SMS Bacterial | Mean SMS Viral | Wilcoxon W Statistic | Wilcoxon P.value |
|---|---|---|---|---|---|---|
| EMEXP3589 | 4 | 5 | 0.372 | -0.298 | 14 | 0.413 |
| GSE15297 | 5 | 8 | 0.208 | -0.13 | 21 | 0.943 |
| GSE20346 | 12 | 8 | -0.0292 | 0.0438 | 43 | 0.734 |
| GSE25504 gpl13667 | 11 | 3 | 0.37 | -1.36 | 32 | 0.011 |
| GSE25504 gpl6947 | 26 | 1 | 0.0888 | -2.31 | 26 | 0.0741 |
| GSE40012 | 36 | 11 | 0.0348 | -0.114 | 192 | 0.892 |
| GSE40396 | 8 | 22 | 0.182 | -0.0661 | 95 | 0.765 |
| GSE42026 | 18 | 41 | 0.531 | -0.233 | 536 | 0.00537 |
| GSE60244 | 22 | 71 | 0.188 | -0.0583 | 901 | 0.28 |
| GSE63990 | 70 | 115 | 0.662 | -0.403 | 6410 | 1.59E-11 |
| GSE66099 | 109 | 11 | 0.0595 | -0.59 | 792 | 0.0808 |

|  |  | Predicted | | |
|---|---|---|---|---|
|  |  | Healthy & SIRS | bacterial | viral |
| Ground Truth | Healthy & SIRS | 560 | 245 | 72 |
| | bacterial | 19 | 505 | 12 |
| | viral | 1 | 94 | 107 |

FIG. 21B

|  |  | Predicted | | |
|---|---|---|---|---|
|  |  | sterile SIRS | bact | viral |
| Ground Truth | sterile SIRS | 25 | 56 | 7 |
|  | bact | 2 | 66 | 2 |
|  | viral | 14 | 41 | 60 |

METHODS FOR DIAGNOSIS OF BACTERIAL AND VIRAL INFECTIONS

CROSS-REFERENCING

This application is the national phase under 35 U.S.C. 0 371 of International Application No. PCT/US2017/036003, filed on Jun. 5,2017, which claims the benefit of U.S. provisional application Ser. No. 62/346,962, filed on Jun. 7, 2016, which application not incorporated by reference herein.

STATEMENT REGARDING FEDERALLY SPONSORED RESEARCH OR DEVELOPMENT

This invention was made with Government support under contracts AI109662 and A1057229 awarded by the National Institutes of Health. The Government has certain rights in the invention.

TECHNICAL FIELD

The present invention pertains generally to methods for diagnosis of bacterial and viral infections. In particular, the invention relates to the use of biomarkers that can distinguish whether a patient with acute inflammation has a bacterial or viral infection.

BACKGROUND

Early and accurate diagnosis of infection is key to improving patient outcomes and reducing antibiotic resistance. The mortality rate of bacterial sepsis increases 8% for each hour by which antibiotics are delayed; however, giving antibiotics to patients without bacterial infections increases rates of morbidity and antimicrobial resistance. The rate of inappropriate antibiotic prescriptions in the hospital setting is estimated at 30-50%, and would be aided by improved diagnostics[2,3]. Strikingly, close to 95% of patients given antibiotics for suspected enteric fever have negative cultures[4]. There is currently no gold-standard point of care diagnostic that can broadly determine the presence and type of infection. Thus, the White House has established a National Action Plan for Combating Antibiotic-Resistant Bacteria, which called for "point-of-need diagnostic tests to distinguish rapidly between bacterial and viral infections"[5]. While new PCR-based molecular diagnostics can profile pathogens directly from a blood culture[6], such methods rely on the presence of adequate numbers of pathogens in the blood. Moreover, they are limited to detecting a discrete range of pathogens. As a result, there is growing interest in molecular diagnostics that profile the host gene response. These include diagnostics that can distinguish the presence of infection as compared to inflamed but non-infected patients, such as our 11-gene 'Sepsis MetaScore'[7] (SMS) (which has been validated across multiple cohorts[8]) among others[9,10]. Other groups have focused on gene sets that can distinguish between types of infections, such as bacterial versus viral infections[11,13]. Tsalik et al. described a model that distinguishes among all three classes (i.e., non-infected patients and those with bacterial or viral illness), though this model required the measurement of 122 probes[14]. We also previously described a 'Meta-Virus Signature' that describes a common response to viral infection, but contained too many genes (396) for clinical application[15]. Overall, while great promise has been shown in this field, no host gene expression infection diagnostic has yet made it into clinical practice.

The data from these biomarker studies and dozens of other genome-wide expression studies in sepsis and acute infections have been published and deposited for further study in public databases such as NIH Gene Expression Omnibus (GEO) and EBI ArrayExpress. These data are a largely untapped resource that can be used for both biomarker discovery and validation. We have previously shown that our integrated multi-cohort analysis of gene expression produces robust diagnostic tools for sepsis[7], specific types of viral infections[15], and active tuberculosis[16]. Further, these data are also useful as a benchmarking and validation tool for novel host gene expression diagnostics[17]. However, such validation in public data has previously been limited to only those cohorts which contain at least two classes of interest (i.e., in which a direct comparison between classes is possible), since inter-study technical differences preclude direct comparison of diagnostic scores between cohorts.

There remains a need for sensitive and specific diagnostic tests that can distinguish between bacterial and viral infections.

SUMMARY

The invention relates to the use of biomarkers that can determine whether a patient with acute inflammation has a bacterial or viral infection. These biomarkers can be used alone or in combination with one or more additional biomarkers or relevant clinical parameters in prognosis, diagnosis, or monitoring treatment of an infection.

In one embodiment, the invention is drawn to a method of developing a classification used for diagnosing an infection in a patient, the method including: (a) measuring levels of expression of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection; wherein the first set of biomarkers include at least one of TSPO, EMR1, NINJ2, ACPP, TBXAS1, PGD, S100A12, SORT1, TNIP1, RAB31, SLC12A9, PLP2, IMPA2, GPAA1, LTA4II, RTN3, CETP, TALD01, IIK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers include at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB; (b) using the levels of expression of the biomarkers to develop a classification or generative algorithm which can determine presence or probability of bacterial or viral infection in the patient; and (c) applying the algorithm to diagnose the patient as having or as likely to have bacterial or viral infection.

In one embodiment, the invention is drawn to a method for diagnosis of an infection in a patient, the method including analyzing levels of expression of at least two genes, wherein the at least two genes are predictive of either a viral or bacterial infection; and wherein the levels of expression of the at least two genes provide an area under a curve for predicting a viral or bacterial infection of at least 0.80; and diagnosing the patient as having either a bacterial or viral infection.

In one embodiment, the invention is drawn to a method for diagnosing and treating an infection in a patient, the method including (a) obtaining a biological sample from the patient; (b) measuring the levels of expression of IFI27, JUP, LAX1, HK3, TNIP1, GPAA1, and CTSB biomarkers in the biological sample; (c) analyzing the levels of expression of each biomarker in conjunction with respective reference value ranges for the biomarkers, wherein increased levels of expression of the IFI27, JUP, LAX1 biomarkers compared to the reference value ranges for the biomarkers for a control subject indicate that the patient has a viral infection, and increased levels of expression of the HK3, TNIP1, GPAA1, CTSB biomarkers compared to the reference value ranges for the biomarkers for a control subject indicate that the patient has a bacterial infection; and (d) administering an effective amount of an anti-viral agent to the patient if the patient is diagnosed with a viral infection or administering an effective amount of an antibiotic to the patient if the patient is diagnosed with a bacterial infection.

In any embodiment, the biological sample can include whole blood or peripheral blood mononucleated cells (PBMCS).

In any embodiment, the levels of the biomarkers can be compared to time-matched reference values for infected or non-infected subjects.

In any embodiment, the method can include calculating a bacterial/viral metascore for the patient based on the levels of the biomarkers, wherein a positive bacterial/viral metascore for the patient indicates that the patient has a viral infection and a negative bacterial/viral metascore for the patient indicates that the patient has a bacterial infection.

In any embodiment, the method can include normalizing data using COCONUT normalization.

In any embodiment, the patient can be a human being.

In any embodiment, measuring the level of the plurality of biomarkers can include performing microarray analysis, polymerase chain reaction (PCR), reverse transcriptase polymerase chain reaction (RT-PCR), a Northern blot, or a serial analysis of gene expression (SAGE).

In one embodiment, the invention is drawn to a method of diagnosing and treating a patient having inflammation, the method including (a) obtaining a biological sample from the patient; (b) measuring levels of expression of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in the biological sample; (c) first analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the patient has an infection, and absence of differential expression of the CEACAM1, ZDHHC19, C9orf95, GNA15, BATF, C3AR1, KIAA1370, TGFBI, MTCH1, RPGRIP1, and HLA-DPB1 biomarkers compared the non-infected control subject indicates that the patient does not have an infection; (d) further analyzing the levels of expression of the IFI27, JUP, LAX1, HK3, TNIP1, GPAA1, and CTSB biomarkers, if the patient is diagnosed as having an infection, wherein increased levels of expression of the IFI27, JUP, LAX1 biomarkers compared to reference value ranges for the biomarkers for a control subject indicate that the patient has a viral infection, and increased levels of expression of the HK3, TNIP1, GPAA1, CTSB biomarkers compared to the reference value ranges for the biomarkers for the control subject indicate that the patient has a bacterial infection; and (e) administering an effective amount of an anti-viral agent to the patient if the patient is diagnosed with a viral infection, or administering an effective amount of an antibiotic to the patient if the patient is diagnosed with a bacterial infection.

In any embodiment, the method can include calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition.

In any embodiment, the method can include calculating a bacterial/viral metascore for the patient if the patient is diagnosed as having an infection, wherein a positive bacterial/viral metascore for the patient indicates that the patient has a viral infection and a negative bacterial/viral metascore for the patient indicates that the patient has a bacterial infection.

In any embodiment, the levels of the biomarkers can be compared to time-matched reference values for infected or non-infected subjects.

In any embodiment, the non-infectious inflammatory condition can be selected from the group of systemic inflammatory response syndrome (SIRS), an autoimmune disorder, a traumatic injury, and surgery.

In any embodiment, the patient can be a human being.

In any embodiment, measuring the levels of the biomarkers can include performing microarray analysis, polymerase chain reaction (PCR), reverse transcriptase polymerase chain reaction (RT-PCR), a Northern blot, or a serial analysis of gene expression (SAGE).

In one embodiment, the invention is drawn to a kit including agents for measuring the levels of IFI27, JUP, LAX1, HK3, TNIP1, GPAA1, and CTSB biomarkers.

In any embodiment, the kit can include agents for measuring the levels of CEACAM1, ZDHHC19, C9orf95, GNA15, BATF, C3AR1, KIAA1370, TGFBI, MTCH1, RPGRIP1, and HLA-DPB1 biomarkers In any embodiment, the kit can include a microarray.

In any embodiment, the microarray can include an oligonucleotide that hybridizes to an IFI27 polynucleotide, an oligonucleotide that hybridizes to a JUP polynucleotide, an oligonucleotide that hybridizes to a LAX1 polynucleotide, an oligonucleotide that hybridizes to a HK3 polynucleotide, an oligonucleotide that hybridizes to a TNIP1 polynucleotide, an oligonucleotide that hybridizes to a GPAA1 polynucleotide, and an oligonucleotide that hybridizes to a CTSB polynucleotide.

In any embodiment the microarray can include an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

In any embodiment, the kit can include information, in electronic or paper form, with instructions to correlate the detected levels of each biomarker with sepsis.

In one embodiment, the method is drawn to a computer implemented method for diagnosing a patient suspected of having an infection, the computer performing steps of: (a) receiving inputted patient data including values for the levels of IFI27, JUP, LAX1, HK3, TNIP1, GPAA1, and CTSB biomarkers in a biological sample from the patient; b) analyzing the level of each of the biomarkers and comparing with respective reference value ranges for the biomarkers; c) calculating a bacterial/viral metascore for the patient based on the levels of the biomarkers, wherein a positive bacterial/viral metascore for the patient indicates that the patient has a viral infection and a negative bacterial/viral metascore for the patient indicates that the patient has a bacterial infection; and (d) displaying information regarding the diagnosis of the patient.

In any embodiment, the biological sample can include whole blood or peripheral blood mononucleated cells (PBMCS).

In one embodiment, the invention is drawn to a diagnostic system for performing the computer implemented method, the diagnostic system including a) a storage component for storing data, wherein the storage component has instructions for determining the diagnosis of the patient stored therein; b) a computer processor for processing data, wherein the computer processor is coupled to the storage component and configured to execute the instructions stored in the storage component in order to receive patient data and analyze patient data according to one or more algorithms; and (c) a display component for displaying information regarding the diagnosis of the patient.

In any embodiment, the storage component can include instructions for calculating the bacterial/viral metascore.

In one embodiment, the invention is drawn to a computer implemented method for diagnosing a patient having inflammation, the computer performing steps of: a) receiving inputted patient data including values for the levels of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in a biological sample from the patient; b) analyzing the levels of each of the biomarkers and comparing with respective reference value ranges for the biomarkers; c) calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition; d) calculating a bacterial/viral metascore for the patient if the sepsis score indicates that the patient has an infection, wherein a positive bacterial/viral metascore for the patient indicates that the patient has a viral infection and a negative bacterial/viral metascore for the patient indicates that the patient has a bacterial infection; and e displaying information regarding the diagnosis of the patient.

In any embodiment, the biological sample can include whole blood or peripheral blood mononucleated cells (PBMCS).

In one embodiment, the invention is drawn to a diagnostic system for performing the computer implemented method, the diagnostic system including a) a storage component for storing data, wherein the storage component has instructions for determining the diagnosis of the patient stored therein; b) a computer processor for processing data, wherein the computer processor is coupled to the storage component and configured to execute the instructions stored in the storage component in order to receive patient data and analyze patient data according to one or more algorithms; and c) a display component for displaying information regarding the diagnosis of the patient.

In any embodiment, the storage component can include instructions for calculating the sepsis metascore and the bacterial/viral metascore.

In one embodiment, the invention is drawn to a method for diagnosing and treating an infection in a patient, the method including: a) obtaining a biological sample from the patient; b) measuring the levels of expression of a set of viral response genes and a set of bacterial response genes in the biological sample, wherein the set of viral response genes includes one or more genes selected from the group of OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, STAT1, and the set of bacterial response genes includes one or more genes selected from the group of SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4H, TALDO1, TKT, PYGL, CETP, PROS1, RTN3, CAT, CYBRD1; and c) analyzing the levels of expression of each biomarker in conjunction with respective reference value ranges for a noninfected control subject, wherein differential expression of the viral response genes compared to the reference value.

In any embodiment, the set of viral response genes and the set of bacterial response genes can be selected from the group of: a) a set of viral response genes including OAS2 and CUL1 and a set of bacterial response genes including SLC12A9, ACPP, STAT5B; b) a set of viral response genes including ISG15 and CHST12 and a set of bacterial response genes including EMR1 and FLII; c) a set of viral response genes including IFIT1, SIGLEC1, and ADA and a set of bacterial response genes including PTAFR, NRD1, PLP2; d) a set of viral response genes including MX1 and a set of bacterial response genes including DYSF, TWF2; e) a set of viral response genes including RSAD2 and a set of bacterial response genes including SORT1 and TSPO; f) a set of viral response genes including IFI44L, GZMB, and KCTD14 and a set of bacterial response genes including TBXAS1, ACAA1, and S100A12; g) a set of viral response genes including LY6E and a set of bacterial response genes including PGD and LAPTM5; h) a set of viral response genes including IFI44, HESX1, and OASL and a set of bacterial response genes including NINJ2, DOK3, SORL1, and RAB31; and i) a set of viral response genes including OAS1 and a set of bacterial response genes including IMPA2 and LTA4H.

In any embodiment, the biological sample can include whole blood or peripheral blood mononucleated cells (PBMCS).

In any embodiment, the levels of the biomarkers can be compared to time-matched reference values for infected or non-infected subjects.

In any embodiment, the method can include calculating a bacterial/viral metascore for the patient t based on the levels of the biomarkers, wherein a positive bacterial/viral metascore for the patient indicates that the patient has a viral infection and a negative bacterial/viral metascore for the patient indicates that the patient has a bacterial infection.

In any embodiment, the method can include measuring levels of expression of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in the biological sample; and analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the patient has an infection, and absence of differential expression of the CEACAM1, ZDHHC19, C9orf95, GNA15, BATF, C3AR1, KIAA1370, TGFBI, MTCH1, RPGRIP1, and HLA-DPB1 biomarkers compared the non-infected control subject indicates that the patient does not have an infection.

In one embodiment, the invention is drawn to a kit including agents for measuring the levels of expression of a set of viral response genes and a set of bacterial response genes selected from the group of: (a) a set of viral response genes including OAS2 and CUL1 and a set of bacterial response genes including SLC12A9, ACPP, STAT5B; (b) a set of viral response genes including ISG15 and CHST12 and a set of bacterial response genes including EMR1 and FLII; b) a set of viral response genes including IFIT1, SIGLEC1, and ADA and a set of bacterial response genes including PTAFR, NRD1, PLP2; c) a set of viral response genes including MX1 and a set of bacterial response genes including DYSF, TWF2; d) a set of viral response genes including RSAD2 and a set of bacterial response genes including SORT1 and TSPO; e) a set of viral response genes including IFI44L, GZMB, and KCTD14 and a set of bacterial response genes including TBXAS1, ACAA1, and S100A12; f) a set of viral response genes including LY6E and a set of bacterial response genes including PGD and LAPTM5; g) a set of viral response genes including IFI44, HESX1, and OASL and a set of bacterial response genes including NINJ2, DOK3, SORL1, and RAB31; and h) a set of viral response genes including OAS1 and a set of bacterial response genes including IMPA2 and LTA4H.

In any embodiment, the kit can include a microarray.

In one embodiment, the invention is drawn to a computer implemented method for diagnosing a patient suspected of having an infection, the computer performing steps of: a) receiving inputted patient data including values for the levels of expression in a biological sample of a set of viral response genes and a set of bacterial response genes in the biological sample, wherein the set of viral response genes includes one or more genes selected from the group of OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, STAT1, and the set of bacterial response genes includes one or more genes selected from the group of SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4H, TALDO1, TKT, PYGL, CETP, PROS1, RTN3, CAT, CYBRD1; b) analyzing the levels of expression of the set of viral response genes and the set of bacterial response genes and comparing with respective reference value ranges for a noninfected control subject; c) calculating a bacterial/viral metascore for the patient based on the levels of expression of the set of viral response genes and the set of bacterial response genes; and (d) displaying information regarding the diagnosis of the patient.

In one embodiment, the invention is drawn to a diagnostic system for performing the computer implemented method, the diagnostic system including a) a storage component for storing data, wherein the storage component has instructions for determining the diagnosis of the patient stored therein; b) a computer processor for processing data, wherein the computer processor is coupled to the storage component and configured to execute the instructions stored in the storage component in order to receive patient data and analyze patient data according to one or more algorithms; and c) a display component for displaying information regarding the diagnosis of the patient.

In one embodiment, the invention includes a method for diagnosing an infection in a patient, including (a) measuring levels of expression of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection; wherein the first set of biomarkers include at least one of TSPO, EMR1, NINJ2, ACPP, TBXAS1, PGD, S100A12, SORT1, TNIP1, RAB31, SLC12A9, PLP2, IMPA2, GPAA1, LTA4H, RTN3, CETP, TALD01, HK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers include at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB; and (b) analyzing the levels of expression of each biomarker in conjunction with respective reference value ranges for the biomarkers to determine a viral or bacterial infection.

In any embodiment, the method can include administering an effective amount of an anti-viral agent to the patient if the patient is diagnosed with a viral infection or administering an effective amount of an antibiotic to the patient if the patient is diagnosed with a bacterial infection.

In any embodiment, the levels of expression of the at least two biomarkers can provide an area under a curve of at least 0.80.

In any embodiment, the first set of biomarkers can include at least one of HK3, TNIP1, GPAA1, and CTSB; and the second set of biomarkers can include at least one of IFI27, JUP, and LAX1.

In any embodiment, the biological sample can include whole blood or peripheral blood mononucleated cells (PBMCS).

In any embodiment, the levels of the biomarkers can be compared to time-matched reference values for infected or non-infected subjects.

In any embodiment, the method can include calculating a bacterial/viral metascore for the patient based on the levels of the biomarkers, wherein a positive bacterial/viral metascore for the patient indicates that the patient has a viral infection and a negative bacterial/viral metascore for the patient indicates that the patient has a bacterial infection.

In any embodiment, the method can include normalizing data using COCONUT normalization; COCONUT normalization including the steps of (a) separating data from multiple cohorts into healthy and diseased components; (b) co-normalizing the healthy components using ComBat co-normalization without covariates; (c) obtaining ComBat estimated parameters for each dataset for the healthy component; and (d) applying the ComBat estimated parameters onto the diseased component.

In any embodiment, the patient can be a human being.

In any embodiment, measuring the level of the plurality of biomarkers can include performing microarray analysis, polymerase chain reaction (PCR), reverse transcriptase polymerase chain reaction (RT-PCR), a Northern blot, or a serial analysis of gene expression (SAGE).

In one embodiment, the invention can include a method of diagnosing and treating a patient having inflammation, the method including the steps of (a) measuring levels of expression of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in a biological sample of the patient; (b) first analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the patient has an infection, and absence of differential expression of the CEACAM1, ZDHHC19, C9orf95, GNA15, BATF, C3AR1, KIAA1370, TGFBI, MTCH1, RPGRIP1, and HLA-DPB1 biomarkers compared the non-infected control subject indicates that the patient does not have an infection; and; (c) further analyzing the levels of expression of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection; wherein the first set of biomarkers include at least one of TSPO, EMR1, NINJ2, ACPP, TBXAS1, PGD, S100A12, SORT1, TNIP1, RAB31, SLC12A9, PLP2, IMPA2, GPAA1, LTA4H, RTN3, CETP, TALDO1, HK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers include at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB to determine a bacterial or viral infection.

In any embodiment, the method can include calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition.

In any embodiment, the method can include calculating a bacterial/viral metascore for the patient if the patient is diagnosed as having an infection, wherein a positive bacterial/viral metascore for the patient indicates that the patient has a viral infection and a negative bacterial/viral metascore for the patient indicates that the patient has a bacterial infection.

In any embodiment, the levels of the biomarkers can be compared to time-matched reference values for infected or non-infected subjects.

In any embodiment, the non-infectious inflammatory condition can be selected from the group of systemic inflammatory response syndrome (SIRS), an autoimmune disorder, a traumatic injury, and surgery.

In any embodiment, the patient can be a human being.

In any embodiment, measuring the levels of the biomarkers can include performing microarray analysis, polymerase chain reaction (PCR), reverse transcriptase polymerase chain reaction (RT-PCR), a Northern blot, or a serial analysis of gene expression (SAGE).

In one embodiment, the method is drawn to a kit, the kit including agents for measuring the levels of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection wherein the first set of biomarkers includes at least one of TSPO, EMR1, NINJ2, ACPP, TBXAS1, PGD, S100A12, SORT1, TNIP1, RAB31, SLC12A9, PLP2, IMPA2, GPAA1, LTA4H, RTN3, CETP, TALDO1, HK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers includes at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB.

In any embodiment, the kit can include agents for measuring the levels of CEACAM1, ZDHHC19, C9orf95, GNA15, BATF, C3AR1, KIAA1370, TGFBI, MTCH1, RPGRIP1, and HLA-DPB1 biomarkers.

In any embodiment, the kit can include a microarray.

In any embodiment, the microarray can include an oligonucleotide that hybridizes to an IFI27 polynucleotide, an oligonucleotide that hybridizes to a JUP polynucleotide, an oligonucleotide that hybridizes to a LAX1 polynucleotide, an oligonucleotide that hybridizes to a HK3 polynucleotide, an oligonucleotide that hybridizes to a TNIP1 polynucleotide, an oligonucleotide that hybridizes to a GPAA1 polynucleotide, and an oligonucleotide that hybridizes to a CTSB polynucleotide.

In any embodiment, the microarray can include an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

In any embodiment, the kit can include information, in electronic or paper form, having instructions to correlate the detected levels of each biomarker with sepsis.

In one embodiment, the invention is drawn to a computer implemented method for diagnosing a patient suspected of having an infection, the computer performing steps of: (a) receiving inputted patient data including values for the levels of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection; wherein the first set of biomarkers include at least one of TSPO, EMR1, NINJ2, ACPP, TBXAS1, PGD, S100A12, SORT1, TNIP1, RAB31, SLC12A9, PLP2, IMPA2, GPAA1, LTA4H, RTN3, CETP, TALD01, HK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers include at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB biomarkers in the biological sample from the patient; (b) analyzing the level of each of the biomarkers and comparing with respective reference value ranges for the biomarkers; (c) calculating a bacterial/viral metascore for the patient based on the levels of the biomarkers, wherein a positive bacterial/viral metascore for the patient indicates that the patient has a viral infection and a negative bacterial/viral metascore for the patient indicates that the patient has a bacterial infection; and (d) displaying information regarding the diagnosis of the patient.

In any embodiment, the biological sample can include whole blood or peripheral blood mononucleated cells (PBMCS). In one embodiment, the invention is drawn to a diagnostic system carrying out the computer implemented method, including (a) a storage component for storing data, wherein the storage component has instructions for determining the diagnosis of the patient stored therein; (b) a computer processor for processing data, wherein the computer processor is coupled to the storage component and configured to execute the instructions stored in the storage component in order to receive patient data and analyze patient data according to one or more algorithms; and (c) a display component for displaying information regarding the diagnosis of the patient.

In any embodiment, the storage component can include instructions for calculating the bacterial/viral metascore.

In one embodiment, the invention is drawn to a computer implemented method for diagnosing a patient having inflammation, the computer performing the steps of (a) receiving inputted patient data having values for the levels of IFI27, JUP, LAX 1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in a biological sample from the patient; (b) analyzing the levels of each of the biomarkers and comparing with respective reference value ranges for the biomarkers; (c) calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition; (d) calculating a bacterial/viral metascore for the patient if the sepsis score indicates that the patient has an infection, wherein a positive bacterial/viral metascore for the patient indicates that the patient has a viral infection and a negative bacterial/viral metascore for the patient indicates that the patient has a bacterial infection; and (e) displaying information regarding the diagnosis of the patient.

In any embodiment, the biological sample can include whole blood or peripheral blood mononucleated cells (PBMCS).

In one embodiment, the invention is drawn to a diagnostic system carrying out the computer implemented method, including (a) a storage component for storing data, wherein the storage component has instructions for determining the diagnosis of the patient stored therein; (b) a computer processor for processing data, wherein the computer processor is coupled to the storage component and configured to execute the instructions stored in the storage component in order to receive patient data and analyze patient data according to one or more algorithms; and (c) a display component for displaying information regarding the diagnosis of the patient.

In any embodiment, the storage component can include instructions for calculating the sepsis metascore and the bacterial/viral metascore.

In one embodiment, the invention is drawn to a method for diagnosing and treating an infection in a patient, the method including (a) obtaining a biological sample from the patient; (b) measuring the levels of expression of any set of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection; wherein the first set of biomarkers include at least one of TSPO, EMR1, NINJ2, ACPP, TBXAS1, PGD, S100A12, SORT1, TNIP1, RAB31, SLC12A9, PLP2, IMPA2, GPAA1, LTA4H, RTN3, CETP, TALD01, HK3, ACAA1, CAT, DOK3, SORL1, PYGL, DYSF, TWF2, TKT, CTSB, FLII, PROS1, NRD1, STAT5B, CYBRD1, PTAFR, and LAPTM5; and wherein the second set of biomarkers include at least one of OAS1, IFIT1, SAMD9, ISG15, HERC5, DDX60, HESX1, IFI6, MX1, OASL, LAX1, IFIT5, IFIT3, KCTD14, OAS2, RTP4, PARP12, LY6E, ADA, IFI44L, IFI27, RSAD2, IFI44, OAS3, IFIH1, SIGLEC1, JUP, STAT1, CUL1, DNMT1, IFIT2, CHST12, ISG20, DHX58, EIF2AK2, XAF1, and GZMB; and (c) analyzing the levels of expression of each biomarker in conjunction with respective reference value ranges for a noninfected control subject, wherein differential expression of the viral response genes compared to the reference value ranges for a noninfected control subject indicate that the patient has a viral infection, and differential expression of the bacterial response genes compared to the reference value ranges for a noninfected control subject indicate that the patient has a bacterial infection.

In any embodiment, the set of viral and bacterial response genes can be selected from the group of: (a) a set of viral response genes including OAS2 and CUL1 and a set of bacterial response genes including SLC12A9, ACPP, STAT5B; (b) a set of viral response genes including ISG15 and CHST12 and a set of bacterial response genes including EMR1 and FLII; (c) a set of viral response genes including IFIT1, SIGLEC1, and ADA and a set of bacterial response genes including PTAFR, NRD1, PLP2; (d) a set of viral response genes including MX1 and a set of bacterial response genes including DYSF, TWF2; (e) a set of viral response genes including RSAD2 and a set of bacterial response genes including SORT1 and TSPO; (f) a set of viral response genes including IFI44L, GZMB, and KCTD14 and a set of bacterial response genes including TBXAS1, ACAA1, and S100A12; (g) a set of viral response genes including LY6E and a set of bacterial response genes including PGD and LAPTM5; (h) a set of viral response genes including IFI44, HESX1, and OASL and a set of bacterial response genes including NINJ2, DOK3, SORL1, and RAB31; and (i) a set of viral response genes including OAS1 and a set of bacterial response genes including IMPA2 and LTA4H.

In any embodiment, the biological sample can include whole blood or peripheral blood mononucleated cells (PBMCS).

In any embodiment, the levels of the biomarkers can be compared to time-matched reference values for infected or non-infected subjects.

In any embodiment, the method can include calculating a bacterial/viral metascore for the patient based on the levels of the biomarkers, wherein a positive bacterial/viral metascore for the patient indicates that the patient has a viral infection and a negative bacterial/viral metascore for the patient indicates that the patient has a bacterial infection.

In any embodiment, the method can include measuring levels of expression of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in the biological sample; and analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the patient has an infection, and absence of differential expression of the CEACAM1, ZDHHC19, C9orf95, GNA15, BATF, C3AR1, KIAA1370, TGFBI, MTCH1, RPGRIP1, and HLA-DPB1 biomarkers compared the non-infected control subject indicates that the patient does not have an infection.

In one embodiment, the method is drawn to a kit, the kit including agents for measuring the levels of expression of a set of viral response genes and a set of bacterial response genes selected from (a) a set of viral response genes including OAS2 and CUL1 and a set of bacterial response genes including SLC12A9, ACPP, STAT5B; (b) a set of viral response genes including ISG15 and CHST12 and a set of bacterial response genes including EMR1 and FLII; (c) a set of viral response genes including IFIT1, SIGLEC1, and ADA and a set of bacterial response genes including PTAFR, NRD1, PLP2; (d) a set of viral response genes including MX1 and a set of bacterial response genes including DYSF, TWF2; (e) a set of viral response genes including RSAD2 and a set of bacterial response genes including SORT1 and TSPO; (f) a set of viral response genes including IFI44L, GZMB, and KCTD14 and a set of bacterial response genes including TBXAS1, ACAA1, and S100A12; (h) a set of viral response genes including IFI44, HESX1, and OASL and a set of bacterial response genes including NINJ2, DOK3, SORL1, and RAB31; and (i) a set of viral response genes including OAS1 and a set of bacterial response genes including IMPA2 and LTA4H.

In any embodiment, the kit can include a microarray.

In one embodiment, the invention is drawn to a computer implemented method for diagnosing a patient suspected of having an infection, the computer performing the steps of (a) receiving inputted patient data including values for the levels of expression of at least two biomarkers in a biological sample of a patient; the at least two biomarkers selected from either or both of a first set of biomarkers wherein a higher level of expression indicates a bacterial infection, and a second set of biomarkers wherein a higher level of expression indicates a viral infection, wherein the set of viral response genes includes one or more genes selected from the group of OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, STAT1, and the set of bacterial response genes includes one or more genes selected from the group of SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4H, TALDO1, TKT, PYGL, CETP, PROS1, RTN3, CAT, CYBRD1; (b) analyzing the levels of expression of the set of viral response genes and the set of bacterial response genes and comparing with respective reference value ranges for a noninfected control subject; (c) calculating a bacterial/viral metascore for the patient based on the levels of expression of the set of viral response genes and the set of bacterial response genes; and (d) displaying information regarding the diagnosis of the patient.

In one embodiment, the invention is drawn to a diagnostic system performing the computer implemented method, the diagnostic system including (a) a storage component for storing data, wherein the storage component has instructions for determining the diagnosis of the patient stored therein; (b) a computer processor for processing data, wherein the computer processor is coupled to the storage component and configured to execute the instructions stored in the storage component in order to receive patient data and analyze patient data according to one or more algorithms; and (c) a display component for displaying information regarding the diagnosis of the patient.

These and other embodiments of the subject invention will readily occur to those of skill in the art in view of the disclosure herein.

BRIEF DESCRIPTION OF THE FIGURES

FIGS. 3A-3C show an integrated antibiotics decision model (IADM) across COCONUT-co-normalized public gene expression data that matched inclusion criteria. FIG.

3A shows an IADM schematic. FIG. 3B shows a distribution of scores and cutoffs for IADM in COCONUT-co-normalized data. FIG. 3C shows a confusion matrix for diagnosis. Bacterial infection sensitivity: 94.0%; Bacterial infection specificity: 59.8%; Viral infection sensitivity: 53.0%; Viral infection specificity: 90.6%.

FIGS. 4A-4E show targeted NanoString gene expression data from children with SIRS/sepsis from the GPSSSI cohort never tested with microarrays (total N=96, of which SIRS=36, bacterial sepsis=49, viral sepsis=11). FIG. 4A shows the breakdown of infected patients by organism type. FIGS. 4B and 4C show ROC curves for the SMS and the bacterial/viral metascore. FIG. 4D shows the distribution of scores and cutoffs for IADM. FIG. 4E shows a confusion matrix for IADM; Bacterial infection sensitivity: 89.7%; Bacterial infection specificity: 70.0%; Viral infection sensitivity: 54.5%; Viral infection specificity: 96.5%.

FIG. 5B shows the distribution of SMS in patients with bacterial versus viral infections. Of 11 datasets, there were only three for which the SMS distribution showed a significant difference between bacterial and viral infections.

FIG. 12A shows raw data and FIG. 12B shows COCONUT co-normalized data. COCONUT co-normalization resets each gene to be at the same location and scale for control patients. Distribution of a gene within a dataset is unchanged (median difference in T-statistics for healthy versus disease within datasets is 0, range (-1e-13, 1e-13), across all genes and all datasets). Housekeeping gene ATP6V1B1 exhibits expected invariance with respect to disease, and is invariant across datasets after normalization. A gene expected to be induced by disease, e.g., CEACAM1, exhibits invariance across healthy controls, but can vary in disease states between datasets. Upper color bars indicate datasets; lower color bar indicate disease class.

FIG. 19A shows age versus SMS by pathogen type, to assess whether pathogen type is driving age differences in SMS. FIG. 19B shows the log10(age) vs. SMS by pathogen type, showing that at extremes of age, the SMS may have a different attainable maximum. FIG. 19C shows the log10(age) versus SMS by dataset, demonstrating that the relationship between age and SMS is dataset-independent. FIGS. 19A-19C only include infected patient samples; FIG. 19D shows both healthy and noninfected SIRS samples in addition to show the baseline across ages. In all cases, the GSE25504 age data are randomly distributed according to the mean age given in their manuscript, roughly 2 weeks +/−1 week, to show data density. All ages=0 were reset as age=1/365.

FIGS. 21A and 21B show the IADM across COCONUT-co-normalized public gene expression data including healthy controls. The included datasets (and the score cutoffs used) are the same as those in FIGS. 3A-3C. FIG. 21A shows the distribution of scores for IADM in COCONUT-co-normalized data. FIG. 21B shows a confusion matrix for diagnosis. Bacterial infection sensitivity: 94.2%; Bacterial infection specificity: 68.5%; Viral infection sensitivity: 53.0%; Viral infection specificity: 94.1%. 'SIRS' refers to non-infected inflammation.

FIGS. 23A-23D show results for the GSE63990 dataset (adults with acute respiratory infections). FIGS. 23A and 23B show ROC curves for the Sepsis MetaScore and the bacterial/viral metascore. FIG. 23C shows the distribution of scores and cutoffs for IADM. FIG. 23D shows a confusion matrix for IADM; Bacterial infection sensitivity: 94.3%; Bacterial infection specificity: 52.2%; Viral infection sensitivity: 52.2%; Viral infection specificity: 94.3%.

DETAILED DESCRIPTION

Figure 1A:
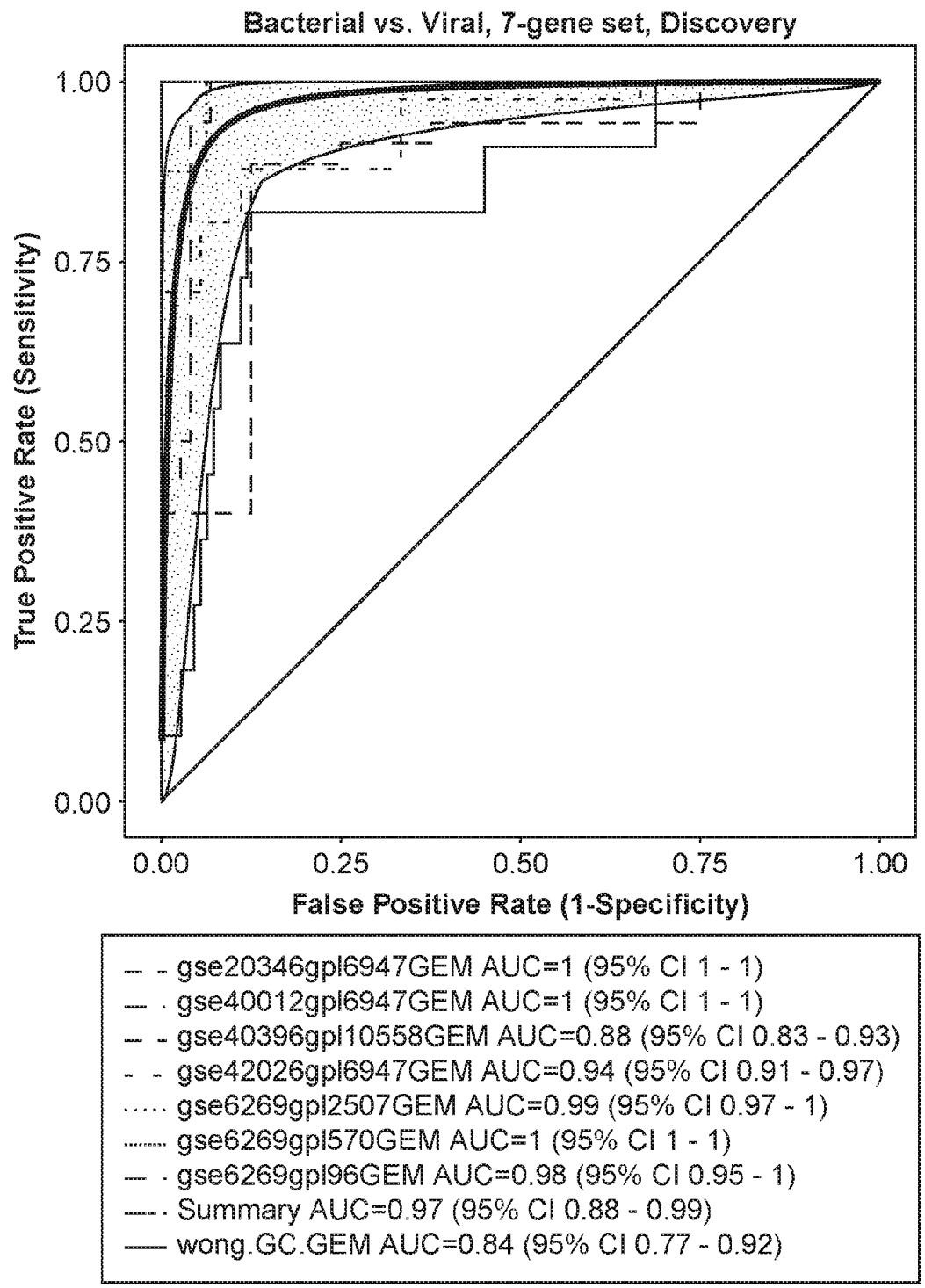
FIGS. 1A and 1B show summary Receiver Operating Characteristic (ROC) curves for (FIG. 1A) discovery and (FIG. 1B) direct validation datasets for the bacterial/viral metascore. A summary ROC curve is shown in black, with 95% confidence intervals in dark grey.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., J. E. Bennett, R. Dolin, and M. J. Blaser *Mandell, Douglas, and Bennett's Principles and Practice of Infectious Diseases* (Saunders, 8th edition, 2014); J. R. Brown *Sepsis: Symptoms, Diagnosis and Treatment* (Public Health in the 21st Century Series, Nova Science Publishers, Inc., 2013); *Sepsis and Noninfectious Systemic Inflammation: From Biology to Critical Care* (J. Cavaillon, C. Adrie eds., Wiley-Blackwell, 2008); Sepsis: *Diagnosis, Management and Health Outcomes* (Allergies and Infectious Diseases, N. Khardori ed., Nova Science Pub Inc., 2014); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

The term Area Under the Curve (AUC) as used herein will be understood to refer to the area under a Receiving Operating Characteristic Curve (ROC Curve).

A "biomarker" in the context of the present invention refers to a biological compound, such as a polynucleotide which is differentially expressed in a sample taken from patients having an infection as compared to a comparable sample taken from control subjects (e.g., a person with a negative diagnosis, normal or healthy subject, or non-infected subject). The biomarker can be a nucleic acid, a fragment of a nucleic acid, a polynucleotide, or an oligonucleotide that can be detected and/or quantified. Biomarkers include polynucleotides comprising nucleotide sequences from genes or RNA transcripts of genes, including but not limited to, IFI27, JUP, LAX1, OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, STAT1, HK3, TNIP1, GPAA1, CTSB, SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4H, TALDO1, TKT, PYGL, CETP, PROS1, RTN3, CAT, CYBRD1, CEACAM1, ZDHHC19, C9orf95, GNA15, BATF, C3AR1, KIAA1370, TGFBI, MTCH1, RPGRIP1, and HLA-DPB1.

"Viral response genes" refer to genes that are differentially expressed in a sample taken from patients having a viral infection as compared to a comparable sample taken from control subjects (e.g., a person with a negative diagnosis, normal or healthy subject, or non-infected subject). Viral response genes include, but are not limited to, IFI27, JUP, LAX1, OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, and STAT1.

"Bacterial response genes" refer to genes that are differentially expressed in a sample taken from patients having a bacterial infection as compared to a comparable sample taken from control subjects (e.g., a person with a negative diagnosis, normal or healthy subject, or non-infected subject). Bacterial response genes include, but are not limited to, HK3, TNIP1, GPAA1, CTSB, SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4II, TALDO1, TKT, PYGL, CETP, PROS1, RTN3, CAT, and CYBRD1.

"Sepsis response genes" refer to genes that are differentially expressed in a sample taken from patients having sepsis or an infection as compared to a comparable sample taken from control subjects (e.g., a person with a negative diagnosis, normal or healthy subject, or non-infected subject). Sepsis response genes include, but are not limited to, CEACAM1, ZDHHC19, C9orf95, GNA15, BATF, C3AR1, KIAA1370, TGFBI, MTCH1, RPGRIP1, and HLA-DPB1.

The terms "polypeptide" and "protein" refer to a polymer of amino acid residues and are not limited to a minimum length. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation, hydroxylation, oxidation, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), and any other type of polynucleotide which is an N- or C-glycoside of a purine or pyrimidine base. There is no intended distinction in length between the terms "polynucleotide," "oligonucleotide," "nucleic acid" and "nucleic acid molecule," and these terms are used interchangeably.

The phrase "differentially expressed" refers to differences in the quantity and/or the frequency of a biomarker present in a sample taken from patients having, for example, an infection (e.g., viral infection or bacterial infection) as compared to a control subject or non-infected subject. For example, a biomarker can be a polynucleotide which is present at an elevated level or at a decreased level in samples of patients with an infection (e.g., viral infection or bacterial infection) compared to samples of control subjects. Alternatively, a biomarker can be a polynucleotide which is detected at a higher frequency or at a lower frequency in samples of patients with an infection (e.g., viral infection or bacterial infection) compared to samples of control subjects. A biomarker can be differentially present in terms of quantity, frequency or both.

A polynucleotide is differentially expressed between two samples if the amount of the polynucleotide in one sample is statistically significantly different from the amount of the polynucleotide in the other sample. For example, a polynucleotide is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polynucleotide is differentially expressed in two sets of samples if the frequency of detecting the polynucleotide in samples of patients' suffering from sepsis, is statistically significantly higher or lower than in the control samples. For example, a polynucleotide is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A "similarity value" is a number that represents the degree of similarity between two things being compared. For example, a similarity value may be a number that indicates the overall similarity between a patient's expression profile using specific phenotype-related biomarkers and reference value ranges for the biomarkers in one or more control samples or a reference expression profile (e.g., the similarity to a "viral infection" expression profile or a "bacterial infection" expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

As used herein, a "biological sample" refers to a sample of tissue, cells, or fluid isolated from a subject, including but not limited to, for example, blood, buffy coat, plasma, serum, blood cells (e.g., peripheral blood mononucleated cells (PBMCS)), fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

A "test amount" of a biomarker refers to an amount of a biomarker present in a sample being tested. A test amount can be either an absolute amount (e.g., μg/ml) or a relative amount (e.g., relative intensity of signals).

A "diagnostic amount" of a biomarker refers to an amount of a biomarker in a subject's sample that is consistent with a diagnosis of an infection (e.g., viral infection or bacterial infection). A diagnostic amount can be either an absolute amount (e.g., µg/ml) or a relative amount (e.g., relative intensity of signals).

A "control amount" of a biomarker can be any amount or a range of amount which is to be compared against a test amount of a biomarker. For example, a control amount of a biomarker can be the amount of a biomarker in a person without an infection (e.g., viral infection or bacterial infection). A control amount can be either in absolute amount (e.g., µg/ml) or a relative amount (e.g., relative intensity of signals).

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) Nature 349:293-299; and U.S. Pat. No. 4,816,567); F(ab')$_2$ and F(ab) fragments; F$_v$ molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, e.g., Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, e.g., Riechmann et al. (1988) Nature 332:323-327; Verhoeyan et al. (1988) Science 239: 1534-1536; and U.K. Patent Publication No. GB 2,276,169, published 21 Sep. 1994); and, any functional fragments obtained from such molecules, wherein such fragments retain specific-binding properties of the parent antibody molecule.

"Detectable moieties" or "detectable labels" contemplated for use in the invention include, but are not limited to, radioisotopes, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), beta-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding β-galactosidase), and xanthine guanine phosphoribosyltransferase (XGPRT), beta-glucuronidase (gus), Placental Alkaline Phosphatase (PLAP), Secreted Embryonic alkaline phosphatase (SEAP), or firefly or bacterial luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the invention, skilled artisans will be aware of additional labels that can be used.

"Developing a classifier" refers to using input variables to generate an algorithm or classifier capable of distinguishing between two or more states.

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The invention is based on the discovery of biomarkers that can be used for diagnosis of an infection (see Example 1). In particular, the invention relates to the use of biomarkers that can be used to determine whether a patient with acute inflammation has a bacterial or viral infection that would benefit from treatment with an antibiotic or antiviral agent. In order to further an understanding of the invention, a more detailed discussion is provided below regarding the identified biomarkers and methods of using them in diagnosis and treatment of infections.

A. Biomarkers

Biomarkers that can be used in the practice of the invention include polynucleotides comprising nucleotide sequences from genes or RNA transcripts of genes, including "viral response genes" that are differentially expressed in patients having a viral infection compared to control subjects (e.g., a person with a negative diagnosis, normal or healthy subject, or non-infected subject not having a viral infection), such as, but not limited to, IFI27, JUP, LAX1, OAS2, CUL1, ISG15, CHST12, IFIT1, SIGLEC1, ADA, MX1, RSAD2, IFI44L, GZMB, KCTD14, LY6E, IFI44, HESX1, OASL, OAS1, OAS3, EIF2AK2, DDX60, DNMT1, HERC5, IFIH1, SAMD9, IFI6, IFIT3, IFIT5, XAF1, ISG20, PARP12, IFIT2, DHX58, and STAT1; "bacterial response genes" that are differentially expressed in patients having a bacterial infection compared to control subjects (e.g., a person with a negative diagnosis, normal or healthy subject, or non-infected subject not having a bacterial infection), such as, but not limited to, HK3, TNIP1, GPAA1, CTSB, SLC12A9, ACPP, STAT5B, EMR1, FLII, PTAFR, NRD1, PLP2, DYSF, TWF2, SORT1, TSPO, TBXAS1, ACAA1, S100A12, PGD, LAPTM5, NINJ2, DOK3, SORL1, RAB31, IMPA2, LTA4H, TALDO1, TKT, PYGL, CETP, PROS1, RTN3, CAT, and CYBRD1; and "sepsis response genes" that are differentially expressed in patients having sepsis or an infection compared to control subjects (e.g., a person with a negative diagnosis, normal or healthy subject, or non-infected subject not having sepsis), such as, but not limited to, CEACAM1, ZDHHC19, C9orf95, GNA15, BATF, C3AR1, KIAA1370, TGFBI, MTCH1, RPGRIP1, and HLA-DPB1.

In one aspect, the invention includes a method of diagnosing an infection in a patient. The method comprises a) obtaining a biological sample from the patient; b) measuring the levels of expression in the biological sample of a set of viral response genes that show differential expression associated with a viral infection and a set of bacterial response genes that show differential expression associated with a bacterial infection; and c) analyzing the levels of expression of the viral response genes and the bacterial response genes in conjunction with respective reference value ranges.

When analyzing the levels of biomarkers in a biological sample, the reference value ranges can represent the levels of one or more biomarkers found in one or more samples of one or more subjects without an infection (e.g., healthy subject or non-infected subject). Alternatively, the reference values can represent the levels of one or more biomarkers found in one or more samples of one or more subjects with a viral infection or a bacterial infection. In certain embodiments, the levels of the biomarkers are compared to time-matched reference values ranges for non-infected or infected subjects.

In certain embodiments, the set of viral response genes and the set of bacterial response genes are selected from the group consisting of: a) a set of viral response genes comprising IF127, JUP, and LAX1 and a set of bacterial response genes comprising HK3, TNIP1, GPAA1, and CTSB; b) a set of viral response genes comprising OAS2 and CUL1 and a set of bacterial response genes comprising SLC12A9, ACPP, STAT5B; c) a set of viral response genes comprising ISG15 and CHST12 and a set of bacterial response genes comprising EMR1 and FLII; d) a set of viral response genes comprising IFIT1, SIGLEC1, and ADA and a set of bacterial response genes comprising PTAFR, NRD1, PLP2; e) a set of viral response genes comprising MX1 and a set of bacterial response genes comprising DYSF, TWF2; f) a set of viral response genes comprising RSAD2 and a set of bacterial response genes comprising SORT1 and TSPO; g) a set of viral response genes comprising IFI44L, GZMB, and KCTD14 and a set of bacterial response genes comprising TBXAS1, ACAA1, and S100A12; h) a set of viral response genes comprising LY6E and a set of bacterial response genes comprising PGD and LAPTM5; i) a set of viral response genes comprising IFI44, HESX1, and OASL and a set of bacterial response genes comprising NINJ2, DOK3, SORL1, and RAB31; and j) a set of viral response genes comprising OAS1 and a set of bacterial response genes comprising IMPA2 and LTA4H.

The biological sample obtained from the patient to be diagnosed is typically whole blood or blood cells (e.g., PBMCS), but can be any sample from bodily fluids, tissue or cells that contain the expressed biomarkers. A "control" sample, as used herein, refers to a biological sample, such as a bodily fluid, tissue, or cells that are not diseased. That is, a control sample is obtained from a normal or non-infected subject (e.g. an individual known to not have a viral infection, bacterial infection, sepsis, or inflammation). A biological sample can be obtained from a patient by conventional techniques. For example, blood can be obtained by venipuncture, and solid tissue samples can be obtained by surgical techniques according to methods well known in the art.

In certain embodiments, a panel of biomarkers is used for diagnosis of an infection. Biomarker panels of any size can be used in the practice of the invention. Biomarker panels for diagnosing an infection typically comprise at least 3 biomarkers and up to 30 biomarkers, including any number of biomarkers in between, such as 3, 4, 5, 6, 7, 8, 9, 10, 11, 12, 13, 14, 15, 16, 17, 18, 19, 20, 21, 22, 23, 24, 25, 26, 27, 28, 29, or 30 biomarkers. In certain embodiments, the invention includes a biomarker panel comprising at least 3, or at least 4, or at least 5, or at least 6, or at least 7, or at least 8, or at least 9, or at least 10, or at least 11 or more biomarkers. Although smaller biomarker panels are usually more economical, larger biomarker panels (i.e., greater than 30 biomarkers) have the advantage of providing more detailed information and can also be used in the practice of the invention.

In certain embodiments, the invention includes a panel of biomarkers for diagnosing an infection comprising one or more polynucleotides comprising a nucleotide sequence from a gene or an RNA transcript of a gene selected from the group consisting of IFI27, JUP, LAX1, HK3, TNIP1, GPAA1, and CTSB. In another embodiment, the panel of biomarkers further comprises one or more polynucleotides comprising a nucleotide sequence from a gene or an RNA transcript of a gene selected from the group consisting of CEACAM1, ZDHHC19, C9orf95, GNA15, BATF, C3AR1, KIAA1370, TGFBI, MTCH1, RPGRIP1, and HLA-DPB1.

In certain embodiments, biomarkers for distinguishing viral and bacterial infections, as described herein, are combined with additional biomarkers that are capable of distinguishing whether inflammation in a subject is caused by an infection or a noninfectious source of inflammation (e.g., traumatic injury, surgery, autoimmune disease, thrombosis, or systemic inflammatory response syndrome (SIRS)). A first diagnostic test is used to determine whether the acute inflammation is caused by an infectious or non-infectious source, and if the source of inflammation is an infection, a second diagnostic test is used to determine whether the infection is a viral infection or a bacterial infection that will benefit from treatment with either antiviral agents or antibiotics, respectively.

In one embodiment, the invention includes a method of diagnosing and treating a patient having inflammation, the method comprising: a) obtaining a biological sample from the patient; b) measuring levels of expression of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in the biological sample; and c) first analyzing the levels of expression of each biomarker in conjunction with respective reference value ranges for the biomarkers, wherein increased levels of expression of the CEACAM1, ZDHHC19, C9orf95, GNA15, BATF, and C3AR1 biomarkers and decreased levels of expression of the KIAA1370, TGFBI, MTCH1, RPGRIP1, and HLA-DPB1 biomarkers compared to the reference value ranges for the biomarkers for a non-infected control subject indicate that the patient has an infection, and absence of differential expression of the CEACAM1, ZDHHC19, C9orf95, GNA15, BATF, C3AR1, KIAA1370, TGFBI, MTCH1, RPGRIP1, and HLA-DPB1 biomarkers compared to the non-infected control subject indicates that the patient does not have an infection; d) second analyzing the levels of expression of the IFI27, JUP, LAX1, HK3, TNIP1, GPAA1, and CTSB biomarkers, if the patient is diagnosed as having an infection, wherein increased levels of expression of the IFI27, JUP, LAX1 biomarkers compared to reference value ranges for the biomarkers for a control subject indicate that the patient has a viral infection, and increased levels of expression of the HK3, TNIP1, GPAA1, CTSB biomarkers compared to the reference value ranges for the biomarkers for the control subject indicate that the patient has a bacterial infection; and e) administering an effective amount of an anti-viral agent to the patient if the patient is diagnosed with a viral infection, or administering an effective amount of an antibiotic to the patient if the patient is diagnosed with a bacterial infection.

In another embodiment, the method further comprises calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition.

In another embodiment, the method further comprises calculating a bacterial/viral metascore for the patient if the patient is diagnosed as having an infection, wherein a positive bacterial/viral metascore for the patient indicates that the patient has a viral infection and a negative bacterial/viral metascore for the patient indicates that the patient has a bacterial infection.

In another embodiment, the invention includes a method of treating a patient suspected of having an infection, the method comprising: a) receiving information regarding the diagnosis of the patient according to a method described herein; and b) administering a therapeutically effective amount of an anti-viral agent if the patient is diagnosed with a viral infection or administering an effective amount of an antibiotic if the patient is diagnosed with a bacterial infection.

In certain embodiments, a patient diagnosed with a viral infection by a method described herein is administered a therapeutically effective dose of an antiviral agent, such as a broad-spectrum antiviral agent, an antiviral vaccine, a neuraminidase inhibitor (e.g., zanamivir (Relenza) and oseltamivir (Tamiflu)), a nucleoside analogue (e.g., acyclovir, zidovudine (AZT), and lamivudine), an antisense antiviral agent (e.g., phosphorothioate antisense antiviral agents (e.g., Fomivirsen (Vitravene) for cytomegalovirus retinitis), morpholino antisense antiviral agents), an inhibitor of viral uncoating (e.g., Amantadine and rimantadine for influenza, Pleconaril for rhinoviruses), an inhibitor of viral entry (e.g., Fuzeon for HIV), an inhibitor of viral assembly (e.g., Rifampicin), or an antiviral agent that stimulates the immune system (e.g., interferons). Exemplary antiviral agents include Abacavir, Aciclovir, Acyclovir, Adefovir, Amantadine, Amprenavir, Ampligen, Arbidol, Atazanavir, Atripla (fixed dose drug), Balavir, Cidofovir, Combivir (fixed dose drug), Dolutegravir, Darunavir, Delavirdine, Didanosine, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine.

In certain embodiments, a patient diagnosed with a bacterial infection by a method described herein is administered a therapeutically effective dose of an antibiotic. Antibiotics may include broad spectrum, bactericidal, or bacteriostatic antibiotics. Exemplary antibiotics include aminoglycosides such as Amikacin, Amikin, Gentamicin, Garamycin, Kanamycin, Kantrex, Neomycin, Neo-Fradin, Netilmicin, Netromycin, Tobramycin, Nebcin, Paromomycin, Humatin, Streptomycin, Spectinomycin(Bs), and Trobicin; ansamycins such as Geldanamycin, Herbimycin, Rifaximin, and Xifaxan; carbacephems such as Loracarbef and Lorabid; carbapenems such as Ertapenem, Invanz, Doripenem, Doribax, Imipenem/Cilastatin, Primaxin, Meropenem, and Merrem; cephalosporins such as Cefadroxil, Duricef, Cefazolin, Ancef, Cefalotin or Cefalothin, Keflin, Cefalexin, Keflex, Cefaclor, Distaclor, Cefamandole, Mandol, Cefoxitin, Mefoxin, Cefprozil, Cefzil, Cefuroxime, Ceftin, Zinnat, Cefixime, Cefdinir, Cefditoren, Cefoperazone, Cefotaxime, Cefpodoxime, Ceftazidime, Ceftibuten, Ceftizoxime, Ceftriaxone, Cefepime, Maxipime, Ceftaroline fosamil, Teflaro, Ceftobiprole, and Zeftera; glycopeptides such as Teicoplanin, Targocid, Vancomycin, Vancocin, Telavancin, Vibativ, Dalbavancin, Dalvance, Oritavancin, and Orbactiv; lincosamides such as Clindamycin, Cleocin, Lincomycin, and Lincocin; lipopeptides such as Daptomycin and Cubicin; macrolides such as Azithromycin, Zithromax, Surnamed, Xithrone, Clarithromycin, Biaxin, Dirithromycin, Dynabac, Erythromycin, Erythocin, Erythroped, Roxithromycin, Troleandomycin, Tao, Telithromycin, Ketek, Spiramycin, and Rovamycine; monobactams such as Aztreonam and Azactam; nitrofurans such as Furazolidone, Furoxone, Nitrofurantoin, Macrodantin, and Macrobid; oxazolidinones such as Linezolid, Zyvox, VRSA, Posizolid, Radezolid, and Torezolid; penicillins such as Penicillin V, Veetids (Pen-Vee-K), Piperacillin, Pipracil, Penicillin G, Pfizerpen, Temocillin, Negaban, Ticarcillin, and Ticar; penicillin combinations such as Amoxicillin/clavulanate, Augmentin, Ampicillin/sulbactam, Unasyn, Piperacillin/tazobactam, Zosyn, Ticarcillin/clavulanate, and Timentin; polypeptides such as Bacitracin, Colistin, Coly-Mycin-S, and Polymyxin B; quinolones/fluoroquinolones such as Ciprofloxacin, Cipro, Ciproxin, Ciprobay, Enoxacin, Penetrex, Gatifloxacin, Tequin, Gemifloxacin, Factive, Levofloxacin, Levaquin, Lomefloxacin, Maxaquin, Moxifloxacin, Avelox, Nalidixic acid, NegGram, Norfloxacin, Noroxin, Ofloxacin, Floxin, Ocuflox Trovafloxacin, Trovan, Grepafloxacin, Raxar, Sparfloxacin, Zagam, Temafloxacin, and Omniflox; sulfonamides such as Amoxicillin, Novamox, Amoxil, Ampicillin, Principen, Azlocillin, Carbenicillin, Geocillin, Cloxacillin, Tegopen, Dicloxacillin, Dynapen, Flucloxacillin, Floxapen, Mezlocillin, Mezlin, Methicillin, Staphcillin, Nafcillin, Unipen, Oxacillin, Prostaphlin, Penicillin G, Pentids, Mafenide, Sulfamylon, Sulfacetamide, Sulamyd, Bleph-10, Sulfadiazine, Micro-Sulfon, Silver sulfadiazine, Silvadene, Sulfadimethoxine Di-Methox, Albon, Sulfamethizole, Thiosulfil Forte, Sulfamethoxazole, Gantanol, Sulfanilimide, Sulfasalazine, Azulfidine, Sulfisoxazole, Gantrisin, Trimethoprim-Sulfamethoxazole (Co-trimoxazole) (TMP-SMX), Bactrim, Septra, Sulfonamidochrysoidine, and Prontosil; tetracyclines such as Demeclocycline, Declomycin, Doxycycline, Vibramycin, Minocycline, Minocin, Oxytetracycline, Terramycin, Tetracycline and Sumycin, Achromycin V, and Steclin; drugs against mycobacteria such as Clofazimine, Lamprene, Dapsone, Avlosulfon, Capreomycin, Capastat, Cycloserine, Seromycin, Ethambutol, Myambutol, Ethionamide, Trecator, Isoniazid, I.N.H., Pyrazinamide, Aldinamide, Rifampicin, Rifadin, Rimactane, Rifabutin, Mycobutin, Rifapentine, Priftin, and Streptomycin; others antibiotics such as Arsphenamine, Salvarsan, Chloramphenicol, Chloromycetin, Fosfomycin, Monurol, Monuril, Fusidic acid, Fucidin, Metronidazole, Flagyl, Mupirocin, Bactroban, Platensimycin, Quinupristin/Dalfopristin, Synercid, Thiamphenicol, Tigecycline, Tigacyl, Tinidazole, Tindamax Fasigyn, Trimethoprim, Proloprim, and Trimpex.

B. Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites) that are indicative of the expression level of the biomarker. The methods for measuring biomarkers in a sample have many applications. For example, one or more biomarkers can be measured to aid in the diagnosis of an infection, to determine the appropriate treatment for a subject, to monitor responses in a subject to treatment, or to identify therapeutic compounds that modulate expression of the biomarkers in vivo or in vitro.

Detecting Biomarker Polynucleotides

In one embodiment, the expression levels of the biomarkers are determined by measuring polynucleotide levels of the biomarkers. The levels of transcripts of specific biomarker genes can be determined from the amount of mRNA, or polynucleotides derived therefrom, present in a biological sample. Polynucleotides can be detected and quantitated by a variety of methods including, but not limited to, microarray analysis, polymerase chain reaction (PCR), reverse transcriptase polymerase chain reaction (RT-PCR), Northern blot, serial analysis of gene expression (SAGE), RNA switches, and solid-state nanopore detection. See, e.g., Draghici *Data Analysis Tools for DNA Microarrays*, Chapman and Hall/CRC, 2003; Simon et al. *Design and Analysis of DNA Microarray Investigations*, Springer, 2004; *Real-Time PCR: Current Technology and Applications*, Logan, Edwards, and Saunders eds., Caister Academic Press, 2009; Bustin A-Z of *Quantitative PCR* (IUL Biotechnology, No. 5), International University Line, 2004; Velculescu et al. (1995) Science 270: 484-487; Matsumura et al. (2005) Cell. Microbiol. 7: 11-18; *Serial Analysis of Gene Expression (SAGE): Methods and Protocols (Methods in Molecular Biology)*, Humana Press, 2008; herein incorporated by reference in their entireties.

In one embodiment, microarrays are used to measure the levels of biomarkers. An advantage of microarray analysis is that the expression of each of the biomarkers can be measured simultaneously, and microarrays can be specifically designed to provide a diagnostic expression profile for a particular disease or condition (e.g., sepsis).

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (3rd Edition, 2001). Alternatively, the solid support or surface may be a glass, silicon, or plastic surface. In one embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel, or a porous wafer such as a TipChip (Axela, Ontario, Canada).

In one embodiment, the microarray comprises a support or surface with an ordered array of binding (e.g., hybridization) sites or "probes" each representing one of the biomarkers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Microarrays can be made in a number of ways, of which several are described below. However they are produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 0.1 cm$^2$ and 25 cm$^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 20 bases and 200 bases in length. PCR methods are well known in the art, and are described, for example, in Innis et al., eds., *PCR Protocols: A Guide To Methods And Applications*, Academic Press Inc., San Diego, Calif. (1990); herein incorporated by reference in its entirety. It will be apparent to one skilled in the art that controlled robotic systems are useful for isolating and amplifying nucleic acids.

An alternative, preferred means for generating polynucleotide probes is by synthesis of synthetic polynucleotides or oligonucleotides, e.g., using N-phosphonate or phosphoramidite chemistries (Froehler et al., Nucleic Acid Res. 14:5399-5407 (1986); McBride et al., Tetrahedron Lett. 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., Nature 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., Nat. Biotech. 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

The probes are attached to a solid support or surface, which may be made, e.g., from glass, plastic (e.g., polypropylene, nylon), polyacrylamide, nitrocellulose, gel, silicon, or other porous or nonporous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids. Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual*, 3rd Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 cm$^2$. The polynucleotide probes are attached to the support covalently at either the 3' or the 5' end of the polynucleotide.

Biomarker polynucleotides which may be measured by microarray analysis can be expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or a fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. No. 5,545,522, 5,891,636, or 5,716,785). Methods for preparing total and poly(A)$^+$ RNA are well known in the art, and are described generally, e.g., in Sambrook, et al., *Molecular Cloning: A Laboratory Manual* (3rd Edition, 2001). RNA can be extracted from a cell of interest using guanidinium thiocyanate lysis followed by CsCl centrifugation (Chirgwin et al., 1979, Biochemistry 18:5294-5299), a silica gel-based column (e.g., RNeasy (Qiagen, Valencia, Calif.) or StrataPrep (Stratagene, La Jolla, Calif.)), or using phenol and chloroform, as described in Ausubel et al., eds., 1989, *Current Protocols In Molecular Biology*, Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. RNA can be fragmented by methods known in the art, e.g., by incubation with $ZnCl_2$, to generate fragments of RNA.

In one embodiment, total RNA, mRNA, or nucleic acids derived therefrom, are isolated from a sample taken from a patient having an infection or inflammation. Biomarker polynucleotides that are poorly expressed in particular cells may be enriched using normalization techniques (Bonaldo et al., 1996, Genome Res. 6:791-806).

As described above, the biomarker polynucleotides can be detectably labeled at one or more nucleotides. Any method known in the art may be used to label the target polynucleotides. Preferably, this labeling incorporates the label uniformly along the length of the RNA, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Chemiluminescent labels that can be used include, but are not limited to, luminol. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

In one embodiment, biomarker polynucleotide molecules from a patient sample are labeled differentially from the corresponding polynucleotide molecules of a reference sample. The reference can comprise polynucleotide molecules from a normal biological sample (i.e., control sample, e.g., blood or PBMCs from a subject not having an infection or inflammation) or from a reference biological sample, (e.g., blood or PBMCs from a subject having a viral infection or bacterial infection).

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization With Nucleic Acid Probes*, Elsevier Science Publishers B.V.; and Kricka, 1992, *Nonisotopic Dna Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously. Alternatively, the probes may be labeled with fluorophores and targets measured with quenchers, such that amplification is tracked by measuring decreasing signal intensity.

In certain embodiments, the invention includes a microarray comprising a plurality of probes for detection of gene expression of a set of viral response genes and a set of bacterial response genes and/or a set of sepsis response genes.

In one embodiment, the microarray comprises an oligonucleotide that hybridizes to an IFI27 polynucleotide, an oligonucleotide that hybridizes to a JUP polynucleotide, an oligonucleotide that hybridizes to a LAX1 polynucleotide, an oligonucleotide that hybridizes to a HK3 polynucleotide, an oligonucleotide that hybridizes to a TNIP1 polynucleotide, an oligonucleotide that hybridizes to a GPAA1 polynucleotide, and an oligonucleotide that hybridizes to a CTSB polynucleotide.

In another embodiment, the microarray further comprises an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB 1 polynucleotide.

Polynucleotides can also be analyzed by other methods including, but not limited to, northern blotting, nuclease protection assays, RNA fingerprinting, polymerase chain reaction, ligase chain reaction, Qbeta replicase, isothermal amplification method, strand displacement amplification, transcription based amplification systems, nuclease protection (Si nuclease or RNAse protection assays), SAGE as well as methods disclosed in International Publication Nos. WO 88/10315 and WO 89/06700, and International Applications Nos. PCT/US87/00880 and PCT/US89/01025; herein incorporated by reference in their entireties.

A standard Northern blot assay can be used to ascertain an RNA transcript size, identify alternatively spliced RNA transcripts, and the relative amounts of mRNA in a sample, in accordance with conventional Northern hybridization techniques known to those persons of ordinary skill in the art. In Northern blots, RNA samples are first separated by size by electrophoresis in an agarose gel under denaturing conditions. The RNA is then transferred to a membrane, cross-linked, and hybridized with a labeled probe. Nonisotopic or high specific activity radiolabeled probes can be used, including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Isotopes that can be used include, but are not limited to, $^{3}H$, $^{14}C$, $^{32}P$, $^{35}S$, $^{36}Cl$, $^{35}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing Si nuclease. The single-stranded, antisense probe must typically be completely homologous to target RNA to prevent cleavage of the probe:target hybrid by nuclease.

Serial Analysis Gene Expression (SAGE) can also be used to determine RNA abundances in a cell sample. See, e.g., Velculescu et al., 1995, Science 270:484-7; Carulli, et al., 1998, Journal of Cellular Biochemistry Supplements 30/31: 286-96; herein incorporated by reference in their entireties. SAGE analysis does not require a special device for detection, and is one of the preferable analytical methods for simultaneously detecting the expression of a large number of transcription products. First, poly A$^+$ RNA is extracted from cells. Next, the RNA is converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified from the nucleotide sequence of the clone and information on the sequence tags.

Quantitative reverse transcriptase PCR (qRT-PCR) can also be used to determine the expression profiles of biomarkers (see, e.g., U.S. Patent Application Publication No. 2005/0048542A1; herein incorporated by reference in its entirety). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 sequence detection system (Perkin-Elmer-Applied Biosystems, Foster City, Calif., USA), or Lightcycler (Roche Molecular Biochemicals, Mannheim, Germany). Alternatives include, but are not limited to, sample-to-answer point-of-need devices such as cobas Liat (Roche Molecular Diagnostics, Pleasanton, Calif., USA) or GeneXpert systems (Cepheid, Sunnyvale, Calif., USA). One of ordinary skill will appreciate that the invention is not limited to the listed devices, and that other devices can be used for TAQMAN-PCR. In a preferred embodiment, the 5' nuclease procedure is run on a real-time quantitative PCR device such as the ABI PRISM 7700 sequence detection system. The system consists of a thermocycler, laser, charge-coupled device (CCD), camera and computer. The system includes software for running the instrument and for analyzing the data. 5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct). Alternatives to standard thermal cycling include, but are not limited to, amplification by continuous thermal gradient, or isothermal amplification with endpoint detection and other known devices to those of ordinary skill. To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and beta-actin.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

An alternative is the detection of PCR products using digital counting methods. These include, but are not limited to, digital droplet PCR and solid-state nanopore detection of PCR products. In these methods the counts of the products of interests may be normalized to the counts of housekeeping genes. Other methods of PCR detection known to those of ordinary skill can be used, and the invention is not limited to the listed methods.

Analysis of Biomarker Data

Biomarker data may be analyzed by a variety of methods to identify biomarkers and determine the statistical significance of differences in observed levels of biomarkers between test and reference expression profiles in order to evaluate whether a patient has inflammation arising from a noninfectious source, such as traumatic injury, surgery, autoimmune disease, thrombosis, or systemic inflammatory response syndrome (SIRS) or an infection, and if the patient is diagnosed with an infection, to diagnose the type of infection, including determining whether a patient has a viral infection or a bacterial infection. In certain embodiments, patient data is analyzed by one or more methods including, but not limited to, multivariate linear discriminant analysis (LDA), receiver operating characteristic (ROC) analysis, principal component analysis (PCA), ensemble data mining methods, significance analysis of microarrays (SAM), cell specific significance analysis of microarrays (csSAM), spanning-tree progression analysis of density-normalized events (SPADE), and multi-dimensional protein identification technology (MUDPIT) analysis. (See, e.g., Hilbe (2009) Logistic Regression Models, Chapman & Hall/CRC Press; McLachlan (2004) Discriminant Analysis and Statistical Pattern Recognition. Wiley Interscience; Zweig et al. (1993) Clin. Chem. 39:561-577; Pepe (2003) The statistical evaluation of medical tests for classification and prediction, New York, N.Y.: Oxford; Sing et al. (2005) Bioinformatics 21:3940-3941; Tusher et al. (2001) Proc. Natl. Acad. Sci. U.S.A. 98:5116-5121; Oza (2006) Ensemble data mining, NASA Ames Research Center, Moffett Field, Calif., USA; English et al. (2009) J. Biomed. Inform. 42(2):287-295; Zhang (2007) Bioinformatics 8: 230; Shen-Orr et al. (2010) Journal of Immunology 184: 144-130; Qiu et al. (2011) Nat. Biotechnol. 29(10):886-891; Ru et al. (2006) J. Chromatogr. A. 1111(2):166-174, Jolliffe Principal Component Analysis (Springer Series in Statistics, $2^{nd}$ edition, Springer, N.Y., 2002), Koren et al. (2004) IEEE Trans Vis Comput Graph 10:459-470; herein incorporated by reference in their entireties.)

C. Kits

In yet another aspect, the invention provides kits for diagnosing an infection in a subject, wherein the kits can be used to detect the biomarkers of the present invention. For example, the kits can be used to detect any one or more of the biomarkers described herein, which are differentially expressed in samples of a patient having a viral or bacterial infection and healthy or non-infected subjects. The kit may include one or more agents for measuring the levels of expression of a set of viral response genes and a set of bacterial response genes, a container for holding a biological sample isolated from a human subject suspected of having an infection; and printed instructions for reacting agents with the biological sample or a portion of the biological sample for measuring the levels of expression of a set of viral response genes and a set of bacterial response genes in the biological sample. The agents may be packaged in separate containers. The kit may further comprise one or more control reference samples and reagents for performing an immunoassay, PCR, or microarray analysis.

In one embodiment, the kit comprises agents for measuring the levels of IFI27, JUP, LAX1, HK3, TNIP1, GPAA1, and CTSB biomarkers for distinguishing viral infections from bacterial infections.

In another embodiment, the kit further comprises agents for measuring the levels of CEACAM1, ZDHHC19, C9orf95, GNA15, BATF, C3AR1, KIAA1370, TGFBI, MTCH1, RPGRIP1, and HLA-DPB1 biomarkers for distinguishing whether inflammation is caused by an infectious or non-infectious source.

In certain embodiments, the kit further comprises a microarray for analysis of a plurality of biomarker polynucleotides. In one embodiment, the microarray comprises an oligonucleotide that hybridizes to an IFI27 polynucleotide, an oligonucleotide that hybridizes to a JUP polynucleotide, an oligonucleotide that hybridizes to a LAX1 polynucleotide, an oligonucleotide that hybridizes to a HK3 polynucleotide, an oligonucleotide that hybridizes to a TNIP1 polynucleotide, an oligonucleotide that hybridizes to a GPAA1 polynucleotide, and an oligonucleotide that hybridizes to a CTSB polynucleotide In another embodiment, the kit further comprises a microarray comprising an oligonucleotide that hybridizes to a CEACAM1 polynucleotide, an oligonucleotide that hybridizes to a ZDHHC19 polynucleotide, an oligonucleotide that hybridizes to a C9orf95 polynucleotide, an oligonucleotide that hybridizes to a GNA15 polynucleotide, an oligonucleotide that hybridizes to a BATF polynucleotide, an oligonucleotide that hybridizes to a C3AR1 polynucleotide, an oligonucleotide that hybridizes to a KIAA1370 polynucleotide, an oligonucleotide that hybridizes to a TGFBI polynucleotide, an oligonucleotide that hybridizes to a MTCH1 polynucleotide, an oligonucleotide that hybridizes to a RPGRIP1 polynucleotide, and an oligonucleotide that hybridizes to a HLA-DPB1 polynucleotide.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of diagnosing infections.

The kits of the invention have a number of applications. For example, the kits can be used to determine if a subject has an infection or some other inflammatory condition arising from a noninfectious source, such as traumatic injury, surgery, autoimmune disease, thrombosis, or systemic inflammatory response syndrome (SIRS). If a patient is diagnosed with an infection, the kits can be used to further determine the type of infection (i.e., viral or bacterial infection). In another example, the kits can be used to determine if a patient having acute inflammation should be treated, for example, with broad spectrum antibiotics or antiviral agents. In another example, kits can be used to monitor the effectiveness of treatment of a patient having an infection. In a further example, the kits can be used to identify compounds that modulate expression of one or more of the biomarkers in in vitro or in vivo animal models to determine the effects of treatment.

D. Diagnostic System and Computerized Methods for Diagnosis of an Infection

In a further aspect, the invention includes a computer implemented method for diagnosing a patient suspected of having an infection. The computer performs steps comprising: receiving inputted patient data comprising values for the levels of expression of either or both of a set of viral response genes and a set of bacterial response genes in a biological sample from the patient; analyzing the levels of expression of the set of genes; calculating a bacterial/viral metascore for the patient based on the levels of expression of the set of genes, wherein the value of the bacterial/viral metascore indicates whether the patient has a viral infection or a bacterial infection; and displaying information regarding the diagnosis of the patient.

In certain embodiments, the inputted patient data comprises values for the levels of expression of a set of viral response genes and a set of bacterial response genes selected from the group consisting of: a) a set of viral response genes comprising IFI27, JUP, and LAX1 and a set of bacterial response genes comprising HK3, TNIP1, GPAA1, and CTSB; b) a set of viral response genes comprising OAS2 and CUL1 and a set of bacterial response genes comprising SLC12A9, ACPP, STAT5B; c) a set of viral response genes comprising ISG15 and CHST12 and a set of bacterial response genes comprising EMR1 and FLII; d) a set of viral response genes comprising IFIT1, SIGLEC1, and ADA and a set of bacterial response genes comprising PTAFR, NRD1, PLP2; e) a set of viral response genes comprising MX1 and a set of bacterial response genes comprising DYSF, TWF2; f) a set of viral response genes comprising RSAD2 and a set of bacterial response genes comprising SORT1 and TSPO; g) a set of viral response genes comprising IFI44L, GZMB, and KCTD14 and a set of bacterial response genes comprising TBXAS1, ACAA1, and S100A12; h) a set of viral response genes comprising LY6E and a set of bacterial response genes comprising PGD and LAPTM5; i) a set of viral response genes comprising IFI44, HESX1, and OASL and a set of bacterial response genes comprising NINJ2, DOK3, SORL1, and RAB31; j) a set of viral response genes comprising OAS1 and a set of bacterial response genes comprising IMPA2 and LTA4H.

In another embodiment, the invention includes a computer implemented method for diagnosing a patient suspected of having an infection, the computer performing steps comprising: a) receiving inputted patient data comprising values for the levels in a biological sample from the patient of IFI27, JUP, LAX1, HK3, TNIP1, GPAA1, and CTSB biomarkers; b) analyzing the level of each of the biomarkers and comparing with respective reference value ranges for the biomarkers; c) calculating a bacterial/viral metascore for the patient based on the levels of expression of the biomarkers, wherein a positive bacterial/viral metascore for the patient indicates that the patient has a viral infection and a negative bacterial/viral metascore for the patient indicates that the patient has a bacterial infection; and d) displaying information regarding the diagnosis of the patient.

In certain embodiments, the inputted patient data further comprises values for the levels of expression of a set of sepsis response genes comprising CEACAM1, ZDHHC19, C9orf95, GNA15, BATF, C3AR1, KIAA1370, TGFBI, MTCH1, RPGRIP1, and HLA-DPB1, wherein the computer implemented method further comprises calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition.

In another embodiment, the invention includes a computer implemented method for diagnosing a patient having inflammation, the computer performing steps comprising: a) receiving inputted patient data comprising values for the levels of IFI27, JUP, LAX1, HK3, TNIP1, GPAA1, CTSB, CEACAM1, ZDHHC19, C9orf95, GNA15, BATF, C3AR1, KIAA1370, TGFBI, MTCH1, RPGRIP1, and HLA-DPB1 biomarkers in a biological sample from the patient; b) analyzing the levels of each of the biomarkers and comparing with respective reference value ranges for the biomarkers; c) calculating a sepsis metascore for the patient, wherein a sepsis metascore that is higher than the reference value ranges for a non-infected control subject indicates that the patient has an infection, and a sepsis metascore that is within the reference value ranges for a non-infected control subject indicates that the patient has a non-infectious inflammatory condition; d) calculating a bacterial/viral metascore for the patient if the sepsis score indicates that the patient has an infection, wherein a positive bacterial/viral metascore for the patient indicates that the patient has a viral infection and a negative bacterial/viral metascore for the patient indicates that the patient has a bacterial infection; and displaying information regarding the diagnosis of the patient.

In a further aspect, the invention includes a diagnostic system for performing the computer implemented method, as described. A diagnostic system includes a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for determining the diagnosis of the patient. For example, the storage component includes instructions for calculating a bacterial/viral metascore and/or sepsis metascore, as described herein (see Example 1). In addition, the storage component may further comprise instructions for performing multivariate linear discriminant analysis (LDA), receiver operating characteristic (ROC) analysis, principal component analysis (PCA), ensemble data mining methods, cell specific significance analysis of microarrays (csSAM), or multi-dimensional protein identification technology (MUDPIT) analysis. The computer processor is coupled to the storage component and configured to execute the instructions stored in the storage component in order to receive patient data and analyze patient data according to one or more algorithms. The display component displays information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may actually comprise a collection of processors which may or may not operate in parallel.

In one aspect, computer is a server communicating with one or more client computers. Each client computer may be configured similarly to the server, with a processor, storage component and instructions. Each client computer may be a personal computer, intended for use by a person, having all the internal components normally found in a personal computer such as a central processing unit (CPU), display (for example, a monitor displaying information processed by the processor), CD-ROM, hard-drive, user input device (for example, a mouse, keyboard, touch-screen or microphone), speakers, modem and/or network interface device (telephone, cable or otherwise) and all of the components used for connecting these elements to one another and permitting them to communicate (directly or indirectly) with one another. Moreover, computers in accordance with the systems and methods described herein may comprise any device capable of processing instructions and transmitting data to and from humans and other computers including network computers lacking local storage capability.

Although the client computers and may comprise a full-sized personal computer, many aspects of the system and method are particularly advantageous when used in connection with mobile devices capable of wireles sly exchanging data with a server over a network such as the Internet. For example, client computer may be a wireless-enabled PDA such as a Blackberry phone, Apple iPhone, Android, or other Internet-capable cellular phone. In such regard, the user may input information using a small keyboard, a keypad, a touch screen, or any other means of user input. The computer may have an antenna for receiving a wireless signal.

The server and client computers are capable of direct and indirect communication, such as over a network. Although only a few computers can be used, it should be appreciated that a typical system can include a large number of connected computers, with each different computer being at a different node of the network. The network, and intervening nodes, may comprise various combinations of devices and communication protocols including the Internet, World Wide Web, intranets, virtual private networks, wide area networks, local networks, cell phone networks, private networks using communication protocols proprietary to one or more companies, Ethernet, WiFi and HTTP. Such communication may be facilitated by any device capable of transmitting data to and from other computers, such as modems (e.g., dial-up or cable), networks and wireless interfaces. The server may be a web server.

Although certain advantages are obtained when information is transmitted or received as noted above, other aspects of the system and method are not limited to any particular manner of transmission of information. For example, in some aspects, information may be sent via a medium such as a disk, tape, flash drive, DVD, or CD-ROM. In other aspects, the information may be transmitted in a non-electronic format and manually entered into the system. Yet further, although some functions are indicated as taking place on a server and others on a client, various aspects of the system and method may be implemented by a single computer having a single processor.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Robust Classification of Bacterial and Viral Infections Via Integrated Host Gene Expression Diagnostics Introduction Here, we sought to improve the diagnostic power of the Sepsis MetaScore (SMS) by adding the ability to discriminate bacterial from viral infections. Thus, in order to derive a new biomarker for discriminating infection types, we applied our multi-cohort analysis framework to clinical microarray cohorts that compared the host response to bacterial and viral infections. We further developed a new method to co-normalize gene expression data among multiple cohorts, allowing direct comparison of a diagnostic score among multiple cohorts. Finally, we combined the Sepsis MetaScore and the new bacterial/viral diagnostic into an integrated antibiotic decision model (IADM) that can determine whether a patient with acute inflammation from any source has an underlying bacterial infection.

Results

Derivation of the 7-Gene Bacterial/Viral Metascore

Figures 5A, 5B:
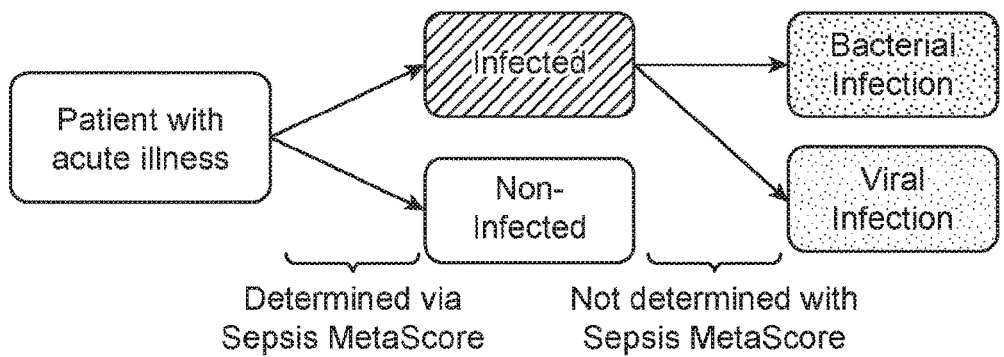
FIGS. 5A and 5B show that the Sepsis MetaScore (SMS) alone cannot determine pathogen type. Diagram in (FIG. 5A) indicates how a decision model could be built.
Figure 6:
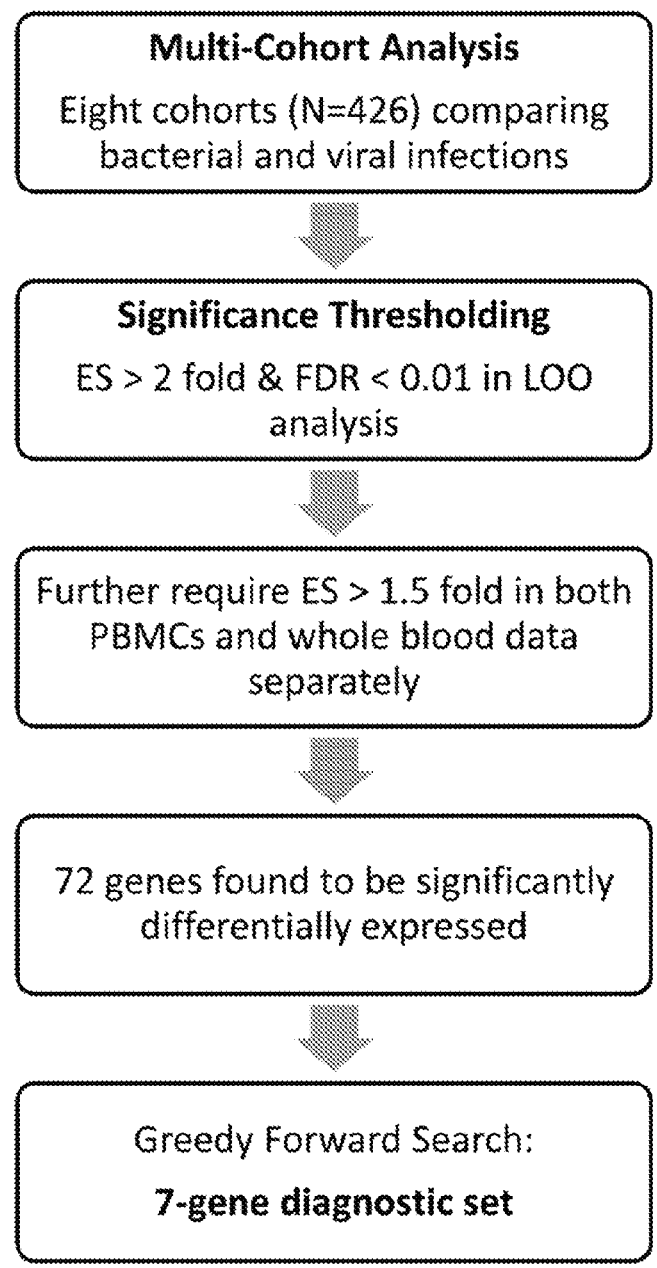
FIG. 6 shows a schematic of the workflow for the multi-cohort analysis and discovery of the bacterial-viral metasignature.
Figure 7:
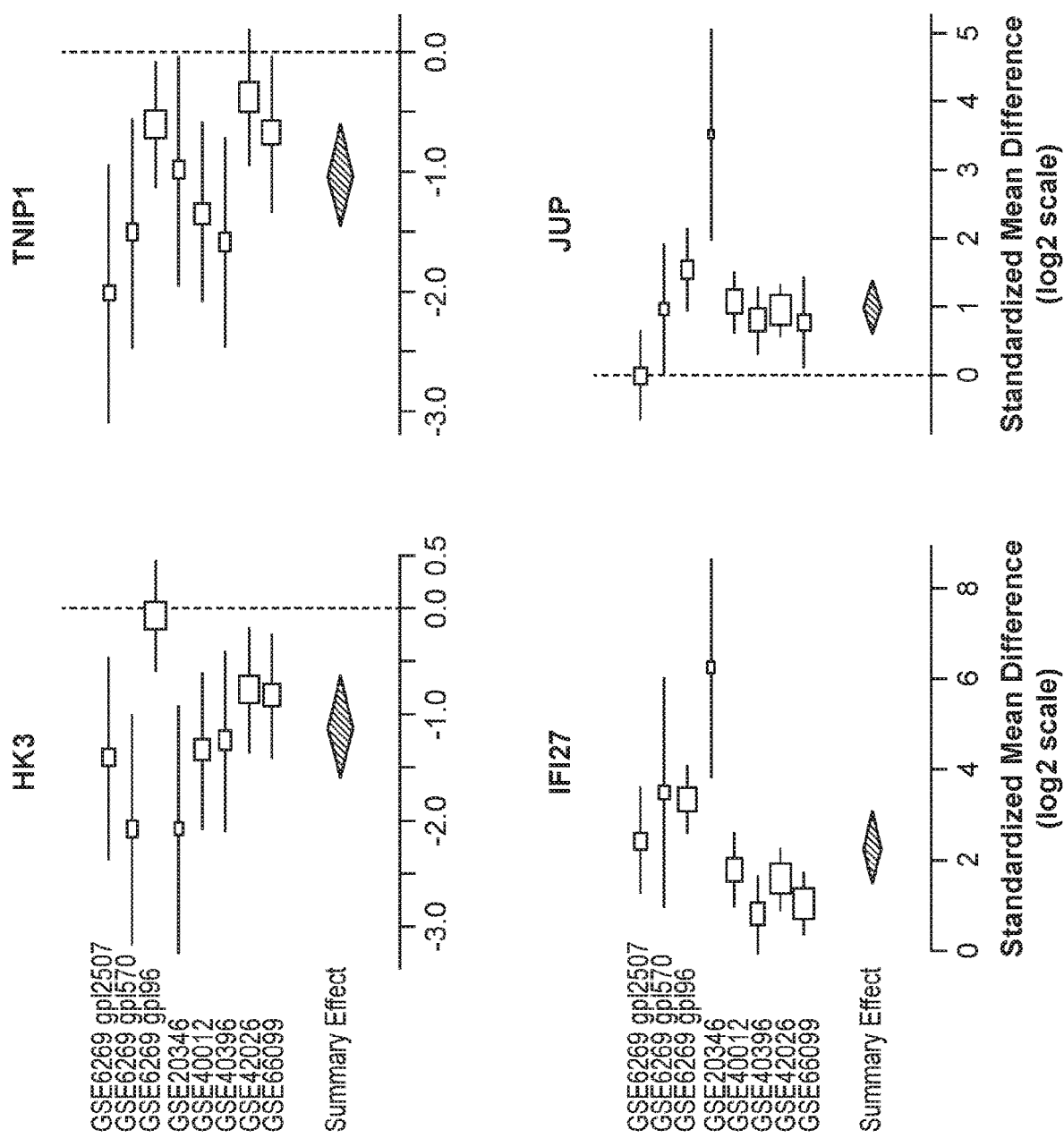
FIG. 7 shows Forest plots of the genes in the bacterial/viral metascore across the discovery datasets. The x axes represent standardized mean difference between bacterial and viral infection samples, computed as Hedges' g, in log2 scale. The size of the black rectangles is inversely proportional to the standard error of mean in the study. Whiskers represent the 95% confidence interval. The light gray diamonds represent overall, combined mean difference for a given gene. Width of the diamonds represents the 95% confidence interval of overall combined mean difference.
Figure 7:
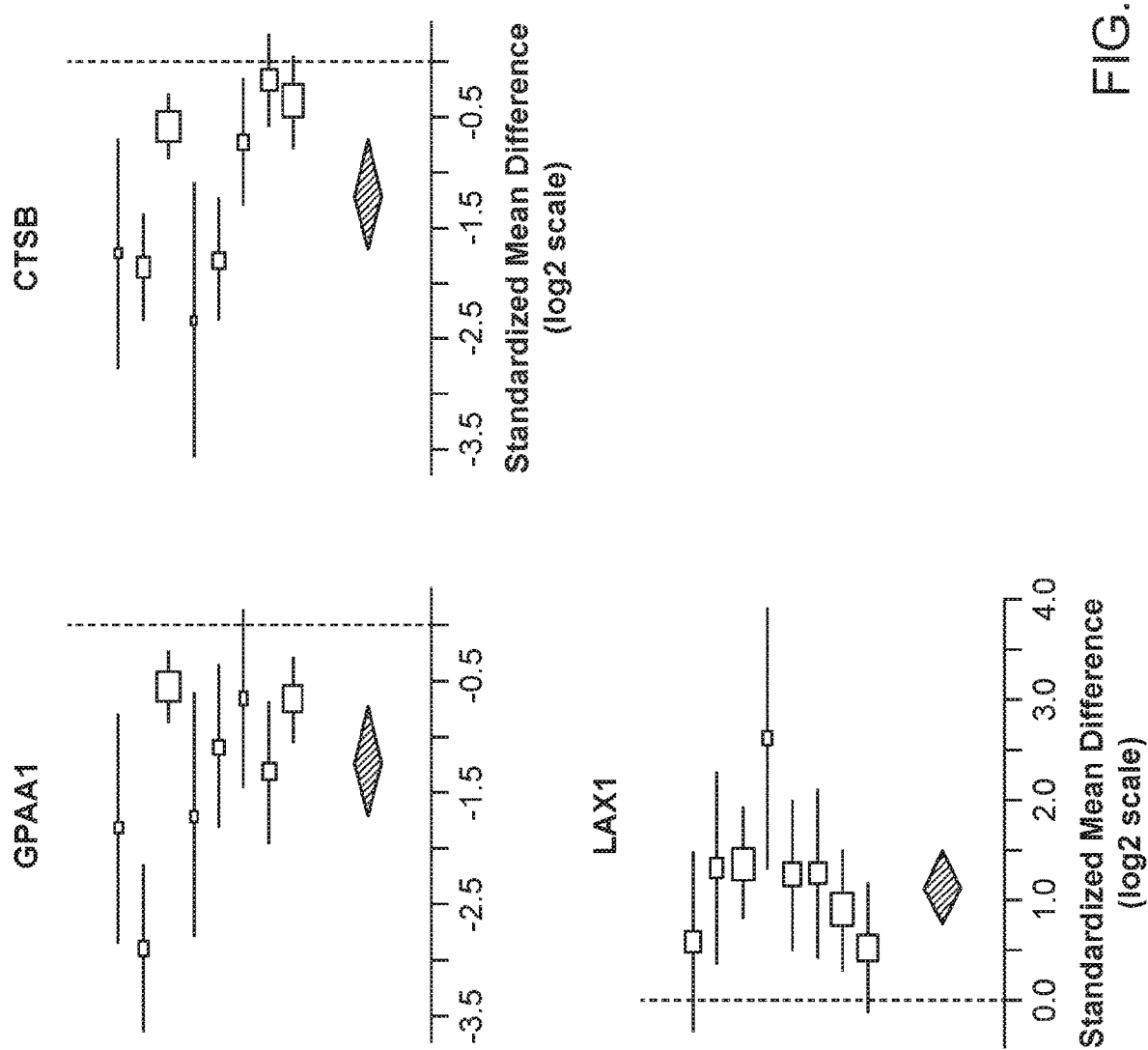
Figure 8:
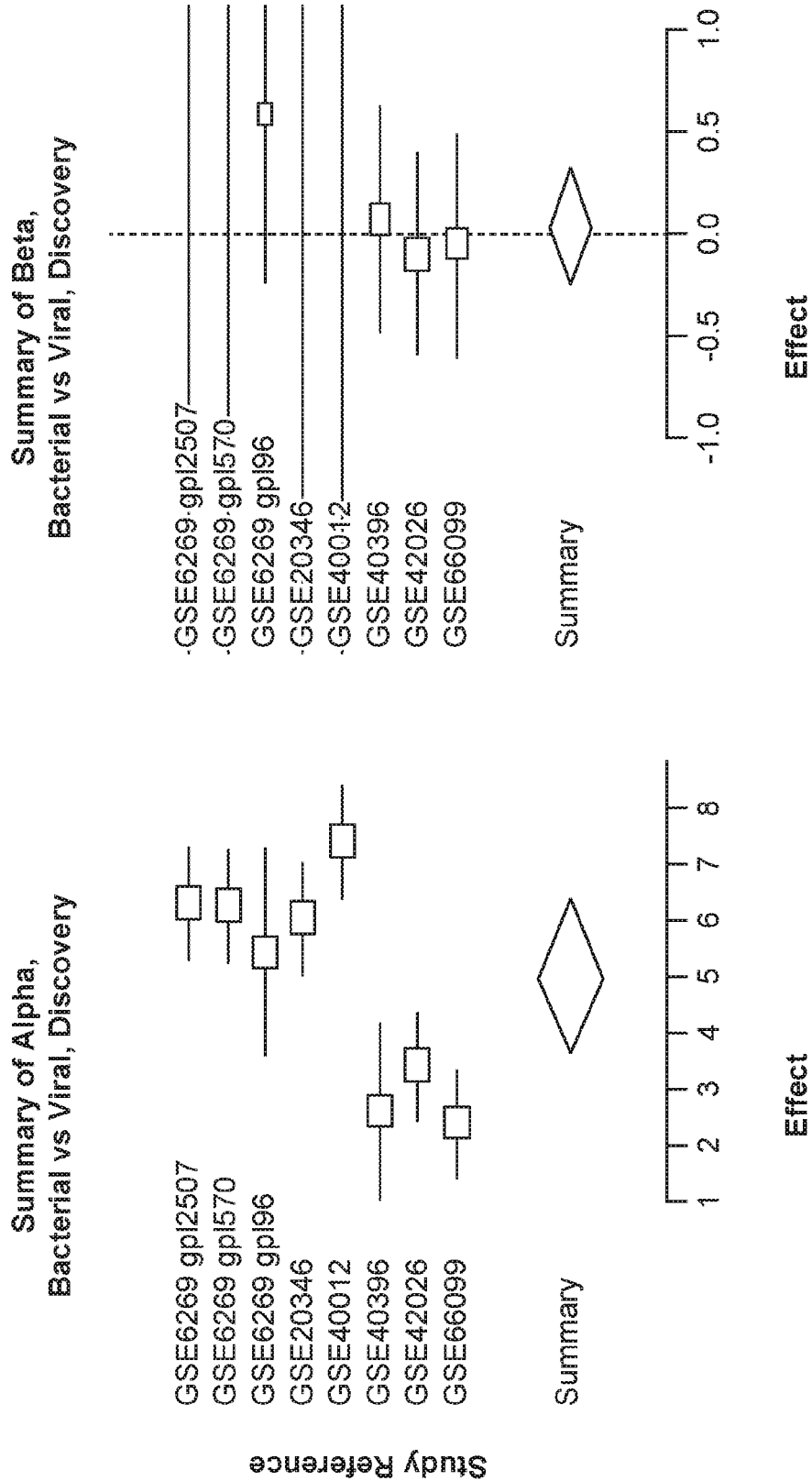
FIG. 8 shows Forest plots of the random-effects meta-analysis of the summary ROC parameters alpha and beta for the discovery datasets. Alpha roughly controls the distance from the line of identity (higher alpha=higher AUC) and beta controls the skew of the actual ROC curve (beta=0 means no skew).

Our previously published 11-gene SMS cannot reliably distinguish between bacterial and viral infections, showing mostly non-significant differences in score distribution between patients with bacterial and viral infections (FIGS. 5A and 5B). Having previously shown that there is a conserved host gene response to viral infections[15], we hypothesized that a classifier for bacterial vs. viral infections would allow for an improved diagnostic model. We thus performed a systematic search for gene expression microarray cohorts that studied patients with viral and/or bacterial infections. We identified 8 cohorts[11,18-26] (both whole blood and PBMCs) that included N>5 patients with both viral and bacterial infections (Table 1A). The 8 cohorts are composed of 426 patient samples (142 viral and 284 bacterial infections), including children and adults, medical and surgical patients, and with multiple sites of infection. We performed multi-cohort analysis on the 8 cohorts as previously described (FIG. 6)[7,15,16,27]. We set significance thresholds of an effect size >2-fold and an FDR <1% in leave-one-dataset-out round-robin analysis. However, in order to make sure that neither tissue type was biasing results, we further selected only those genes that also had an effect size >1.5 fold in separate analyses of both PBMCs and whole blood cohorts. This process resulted in 72 significantly differentially expressed genes (Supplemental Table 1). A greedy forward search was then used to find a gene set optimized for diagnosis, resulting in 7 genes (higher in viral infections: IFI27, JUP, LAX1, higher in bacterial infections: HK3, TNIP1, GPAA1, CTSB; FIG. 7). As expected, a 'bacterial/viral metascore' based on these 7 genes robustly distinguished viral from bacterial infections in all 8 of the discovery cohorts (summary ROC AUC=0.97, 95% CI=0.89-0.99, FIG. 1A, FIG. 8).

Figure 1B:
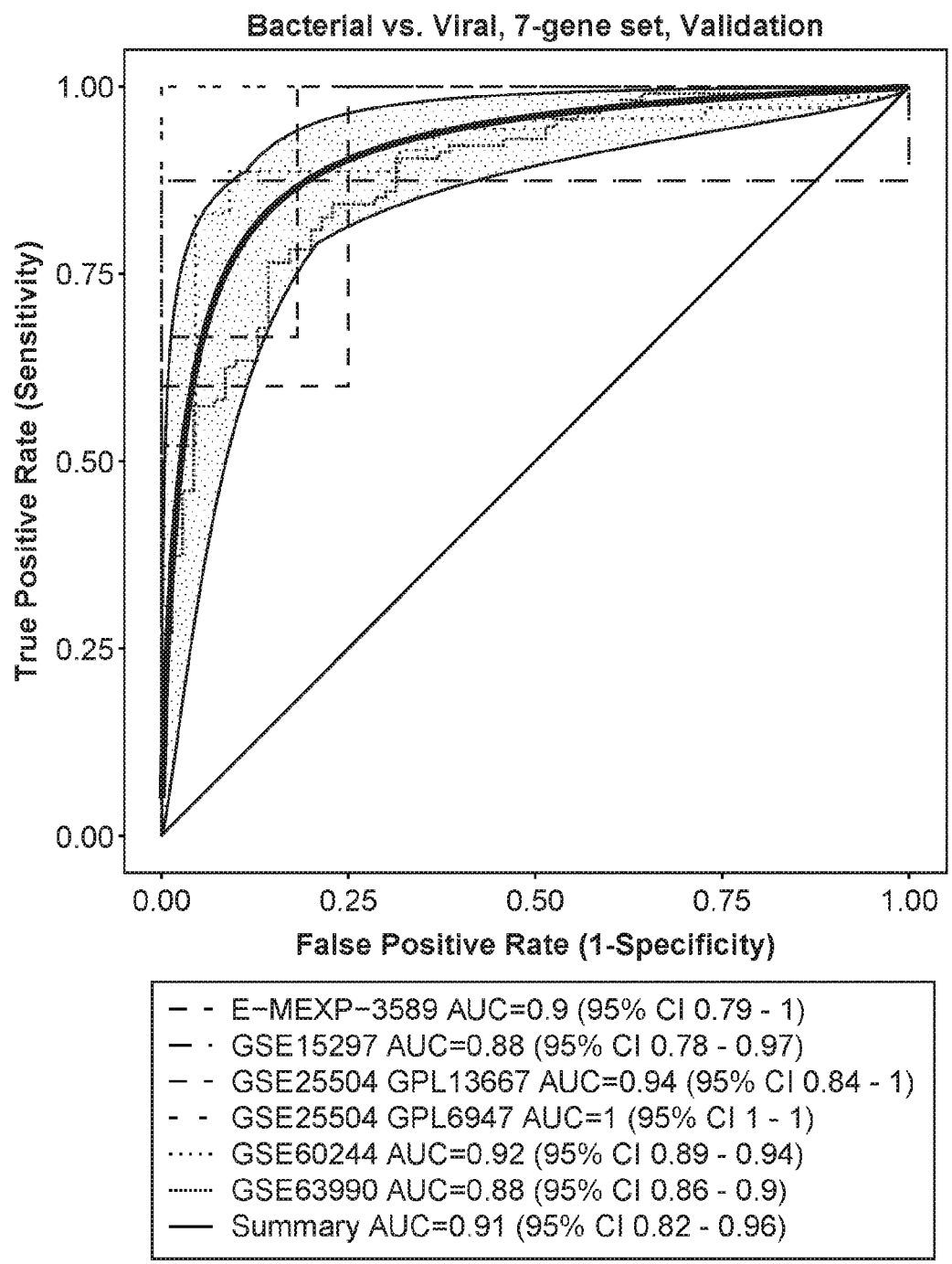
Figure 9:
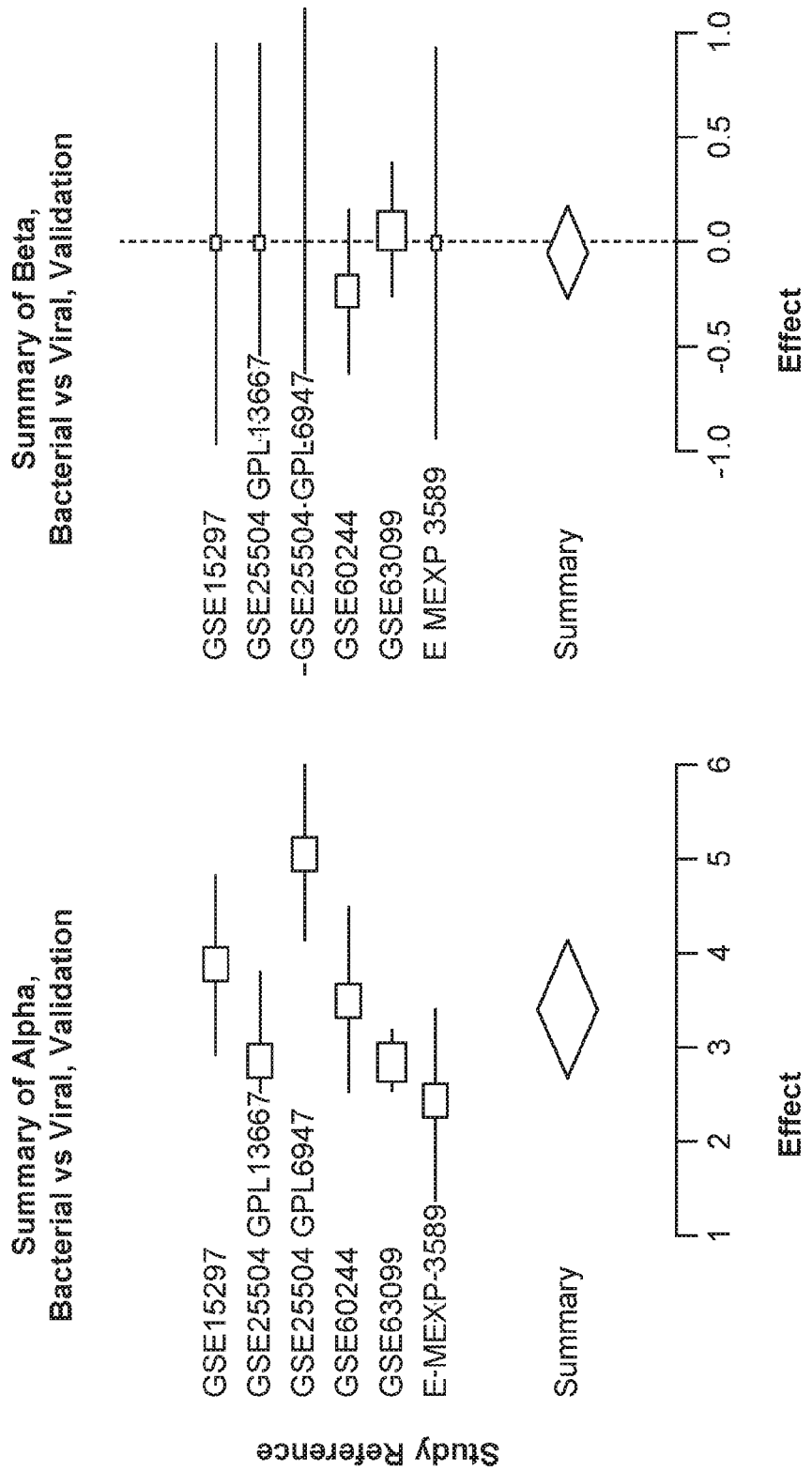
FIG. 9 shows Forest plots of the random-effects meta-analysis of the summary ROC parameters alpha and beta for the validation datasets. Alpha roughly controls the distance from the line of identity (higher alpha=higher AUC) and beta controls the skew of the actual ROC curve (beta=0 means no skew).

We next tested the 7-gene set in the 6 remaining independent clinical cohorts[13,14,28,30] that directly compared bacterial and viral infections (total 341 samples, 138 bacterial and 203 viral), and found a summary ROC AUC of 0.91 (95% C0.82-0.96) (Table 1B, FIG. 1B, FIG. 9). As a test of signature generalizability, we also tested whether cells stimulated in vitro with LPS or influenza virus could be separated with the bacterial/viral metascore (GSE53166[31], N=75, AUC=0.99) FIG. 10).

Global Validation Via COCONUT Co-Normalization

Figure 2:
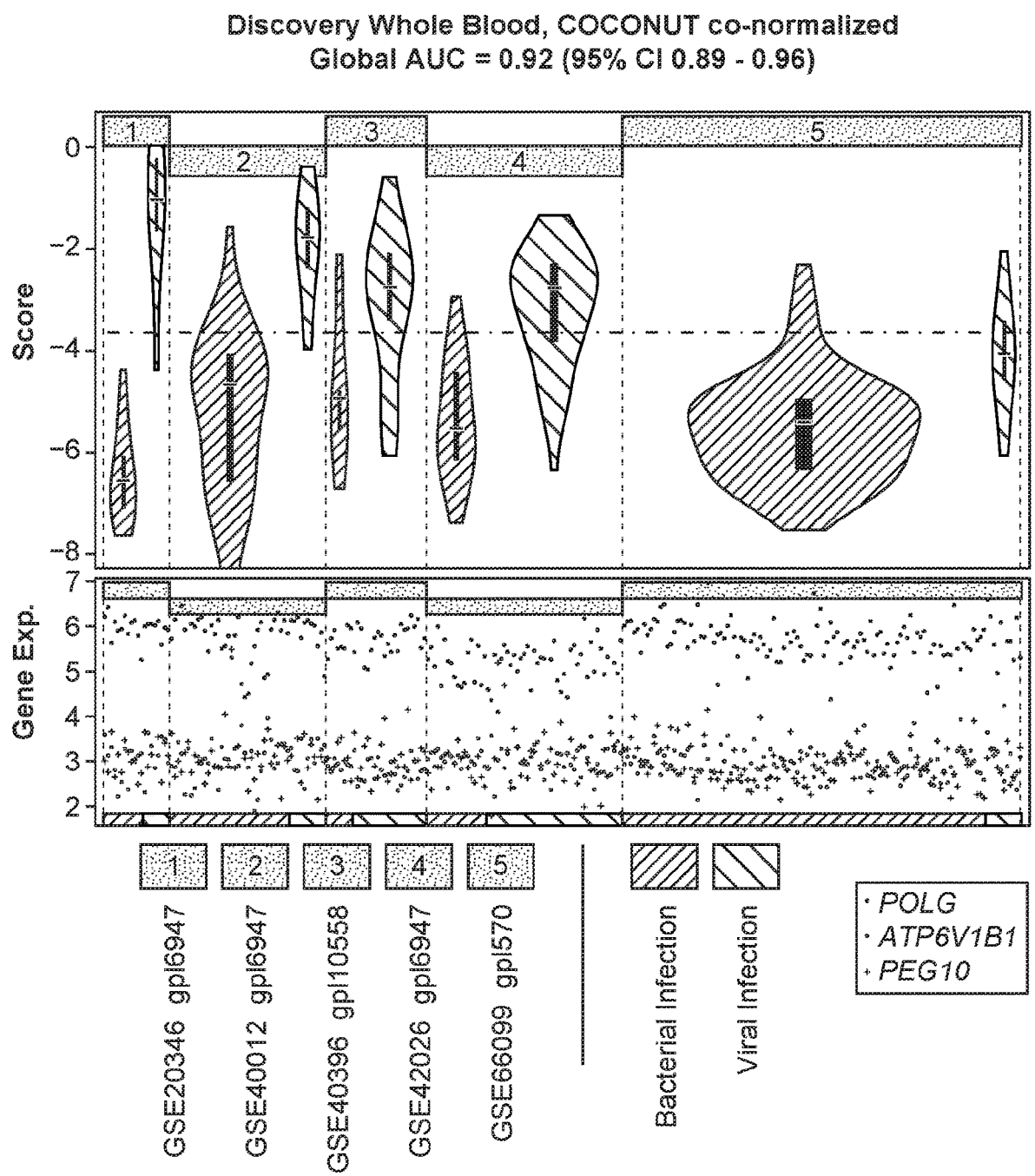
FIG. 2 shows bacterial/viral scores for COCONUT co-normalized whole blood discovery datasets. PBMCs datasets are left out of FIG. 2 because PBMC datasets are expected to have different gene levels than whole blood. The global AUC across all whole blood discovery datasets is 0.92. Score distribution by dataset (dark gray =bacterial, light gray=viral), individual gene levels, and housekeeping genes (greyscale) are shown. The dotted line shows a possible global threshold. The width of each violin corresponds to the distribution of scores within the given dataset. The vertical bar within each violin spans the $25^{th}$-$75^{th}$ percentile, and the middle white dash shows the mean score. Housekeeping genes (POLG, ATP6V1B1, and PEG10) show expected invariance across datasets post-COCONUT-normalization.
Figure 11:
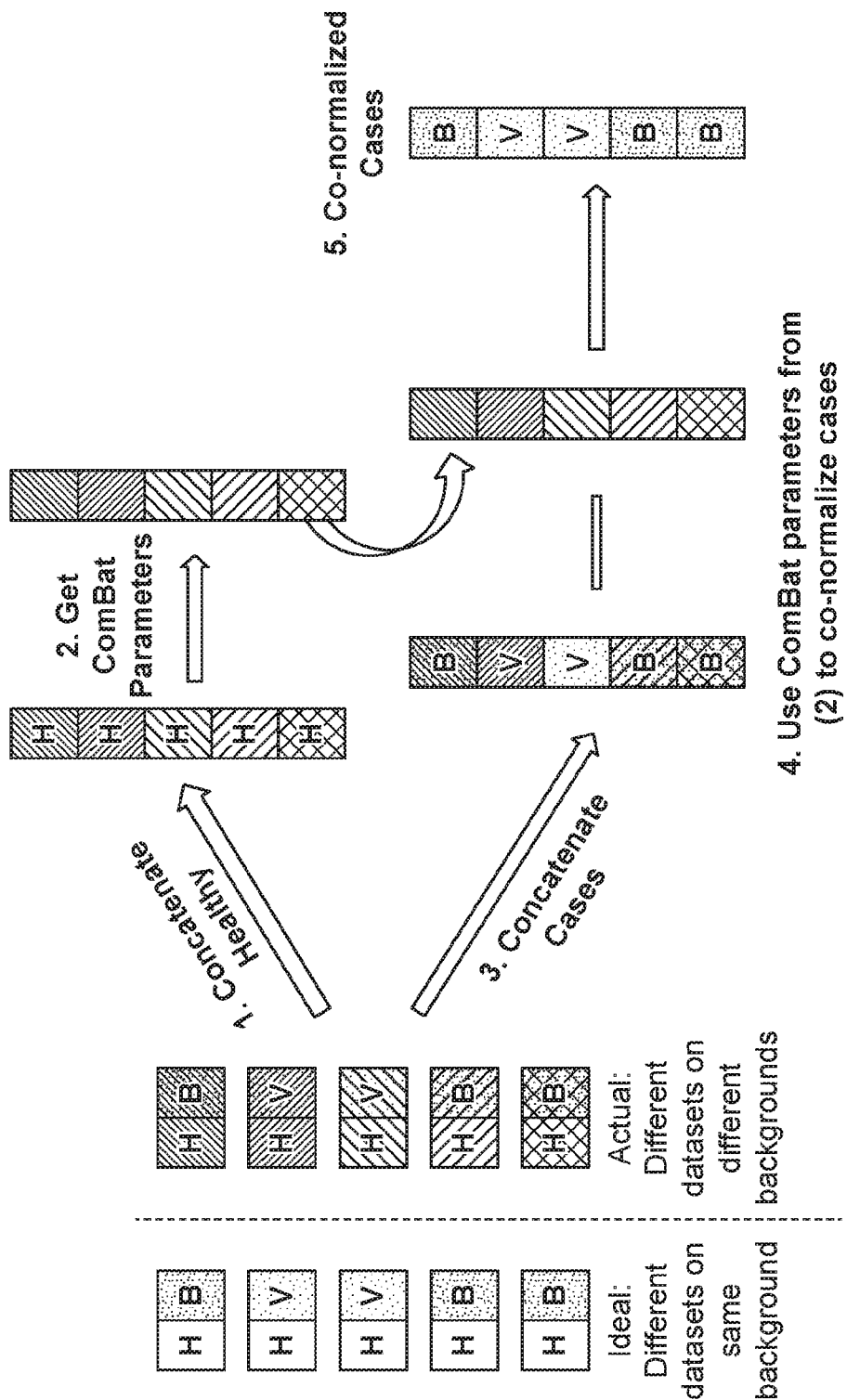
FIG. 11 shows a schematic of COCONUT co-normalization. Light gray indicates healthy ('H'), medium gray means viral ('V') and dark gray means bacterial ('B'). Different crosshatchings are meant to indicate different batch effects. See Methods for formal mathematical details.
Figure 12A:
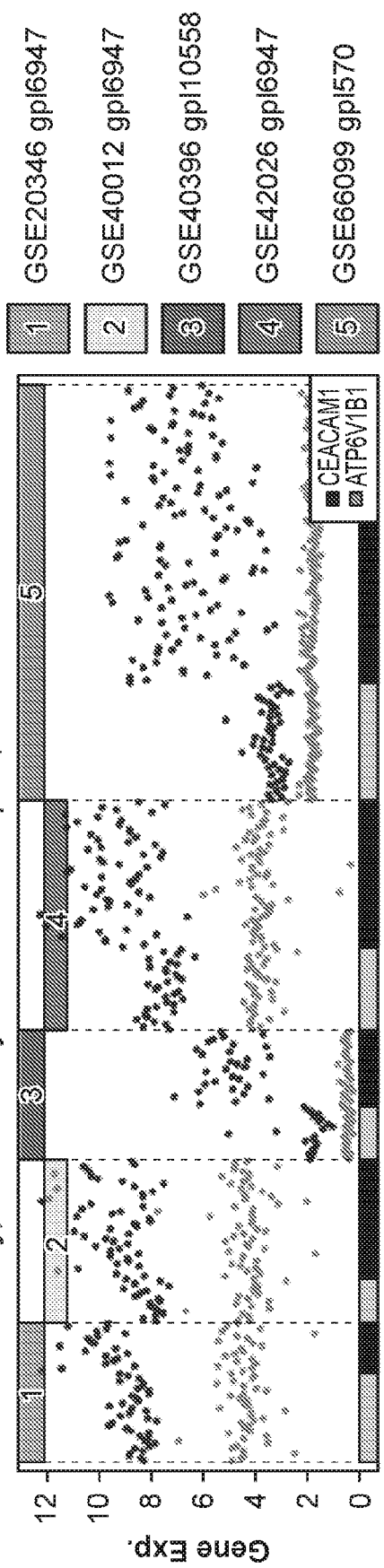
FIGS. 12A and 12B show data of whole blood discovery datasets. PBMCs datasets are left out of FIGS. 12A and 12B because PBMC datasets are expected to have different gene levels than whole blood.
Figure 12B:
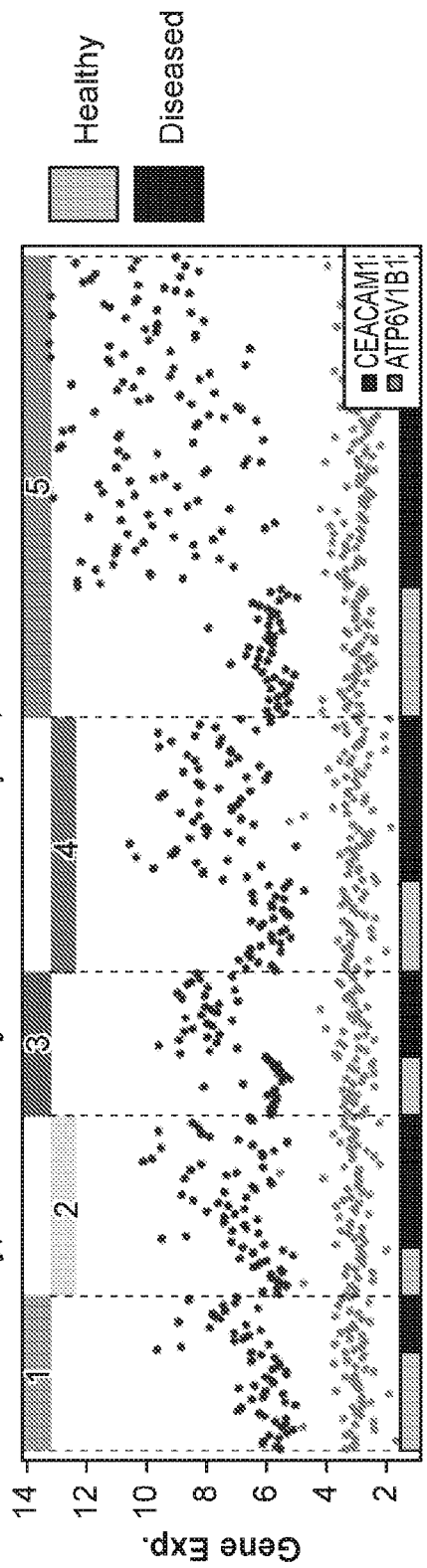
Figure 13:
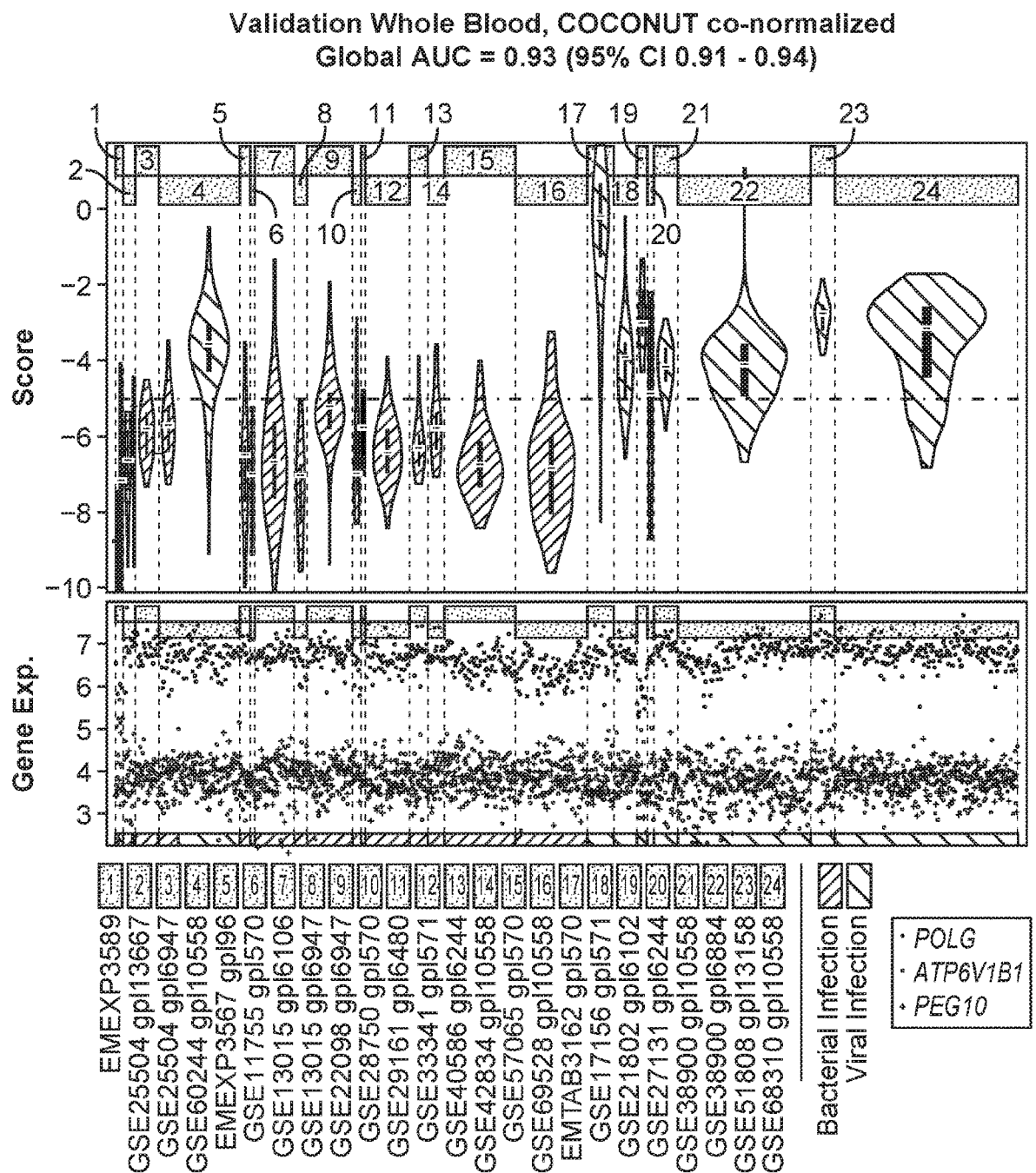
FIG. 13 shows the bacterial/viral score in global ROC of COCONUT co-normalization of whole blood validation datasets. The global AUC across all whole blood validation datasets is 0.93. The score distribution by dataset (dark gray violins=bacterial, light gray violins=viral) and housekeeping genes (greyscale) are shown. The width of each violin corresponds to the distribution of scores within the given dataset. The vertical bar within each violin spans the $25^{th}$-$75^{th}$ percentile, and the middle white dash shows the mean score. The dotted line shows a possible global threshold. Housekeeping genes (POLG, ATP6V1B1, and PEG10) show expected invariance across datasets post-COCONUT-normalization.
Figure 14:
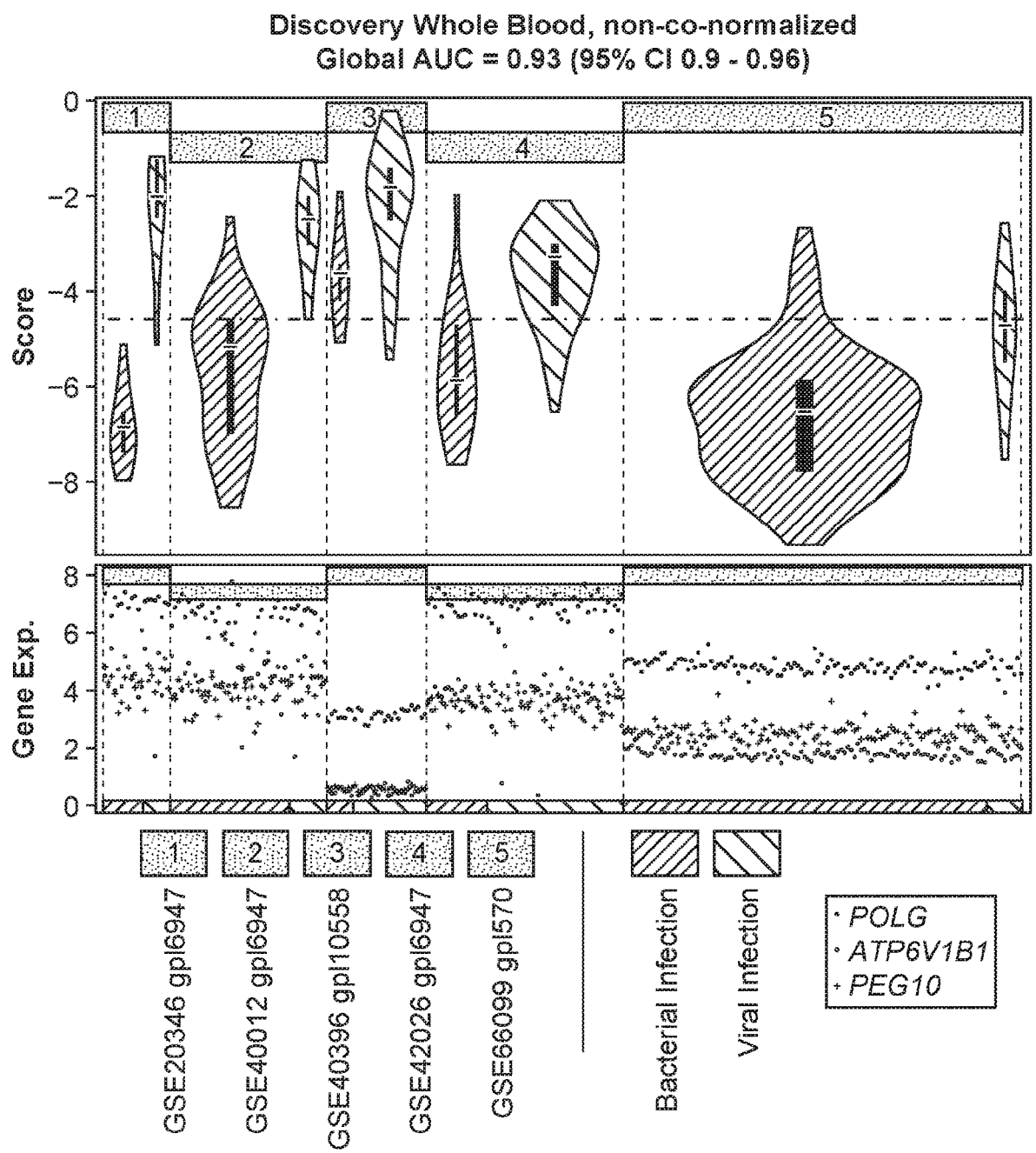
FIG. 14 shows the bacterial/viral score in global ROC of non-co-normalized whole blood discovery datasets. PBMCs datasets are left out of FIG. 14 because PBMC datasets are expected to have different gene levels than whole blood. The global AUC across all whole blood discovery datasets is 0.93. The score distribution by dataset (dark gray violins=bacterial, light gray violins=viral) and housekeeping genes (greyscale) are shown. The width of each violin corresponds to the distribution of scores within the given dataset. The vertical bar within each violin spans the $25^{th}$-$75^{th}$ percentile, and the middle white dash shows the mean score. Note the highly varying locations and scales of the housekeeping genes POLG, ATP6V1B1, and PEG10.
Figure 15:
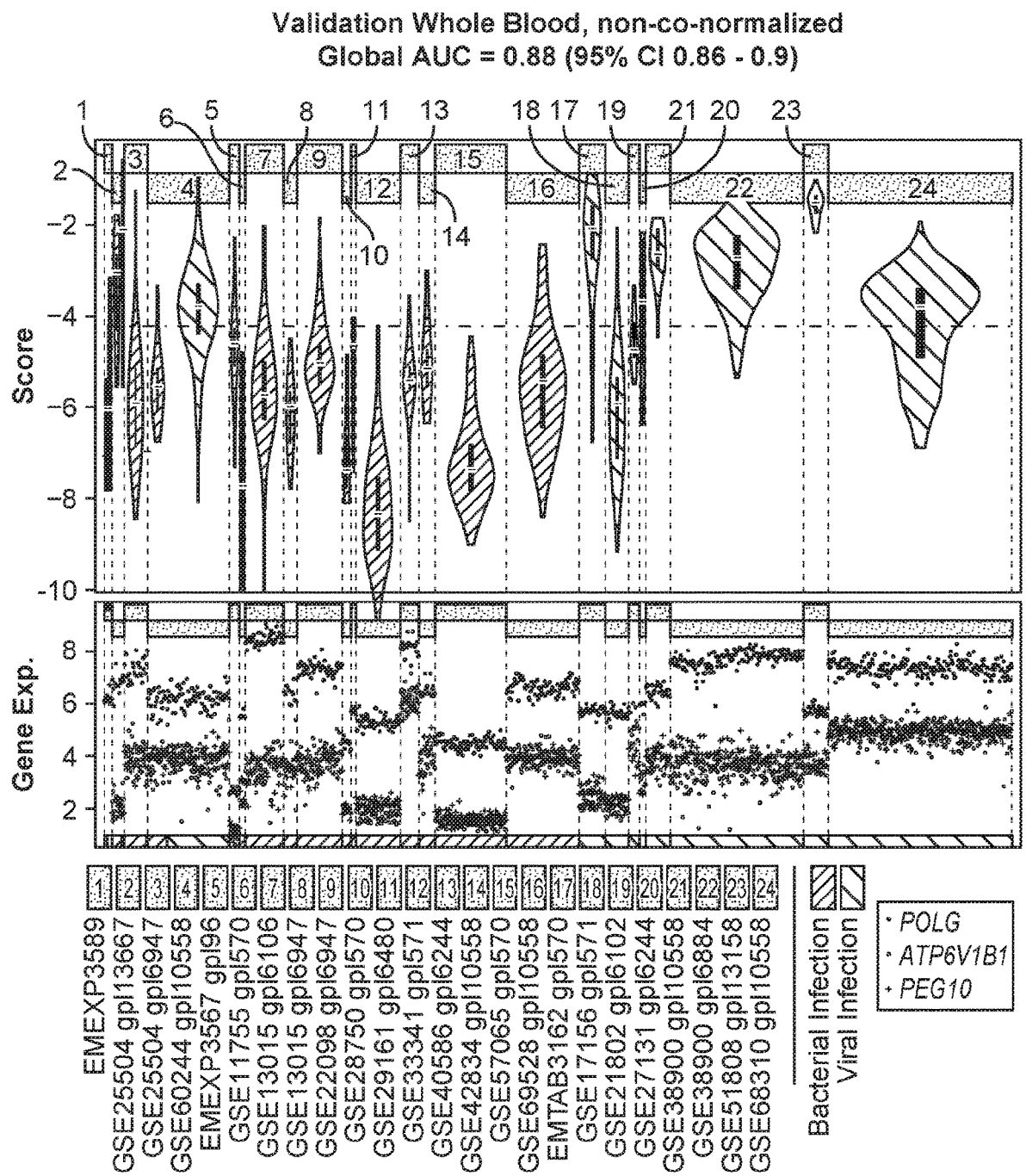
FIG. 15 shows the bacterial/viral score in global ROC of non-co-normalized whole blood validation datasets. PBMCs datasets are left out of FIG. 15 because PBMC datasets are expected to have different gene levels than whole blood. The score distribution by dataset (dark gray violins=bacterial, light gray violins=viral) and housekeeping genes (greyscale) are shown. The width of each violin corresponds to the distribution of scores within the given dataset. The vertical bar within each violin spans the $25^{th}$-$75^{th}$ percentile, and the middle white dash shows the mean score. Note the highly varying locations and scales of the housekeeping genes POLG, ATP6V1B1, and PEG10.
Figure 16:
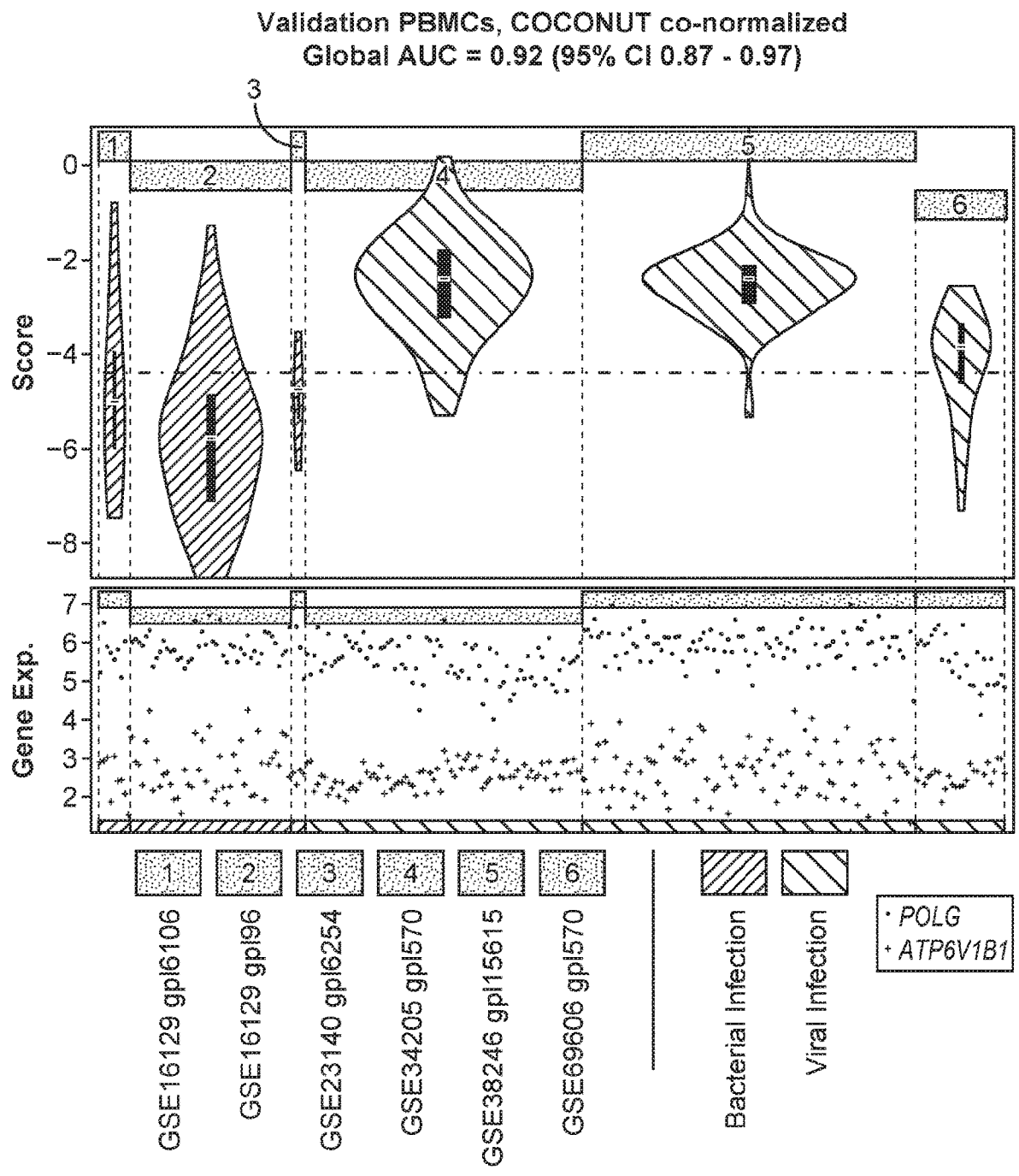
FIG. 16 shows the bacterial/viral score in global ROC of COCONUT co-normalization of PBMC validation datasets. PBMCs datasets are examined separately because PBMC datasets are expected to have different gene levels than whole blood. The global AUC across all PBMC validation datasets is 0.92. The score distribution by dataset (dark gray violins=bacterial, light gray violins=viral) and housekeeping genes (greyscale) are shown. The dotted line shows a possible global threshold. The width of each violin corresponds to the distribution of scores within the given dataset. The vertical bar within each violin spans the $25^{th}$-$75^{th}$ percentile, and the middle white dash shows the mean score. Housekeeping genes (POLG, ATP6V1B1) show expected invariance across datasets post-COCONUT-normalization.
Figure 17:
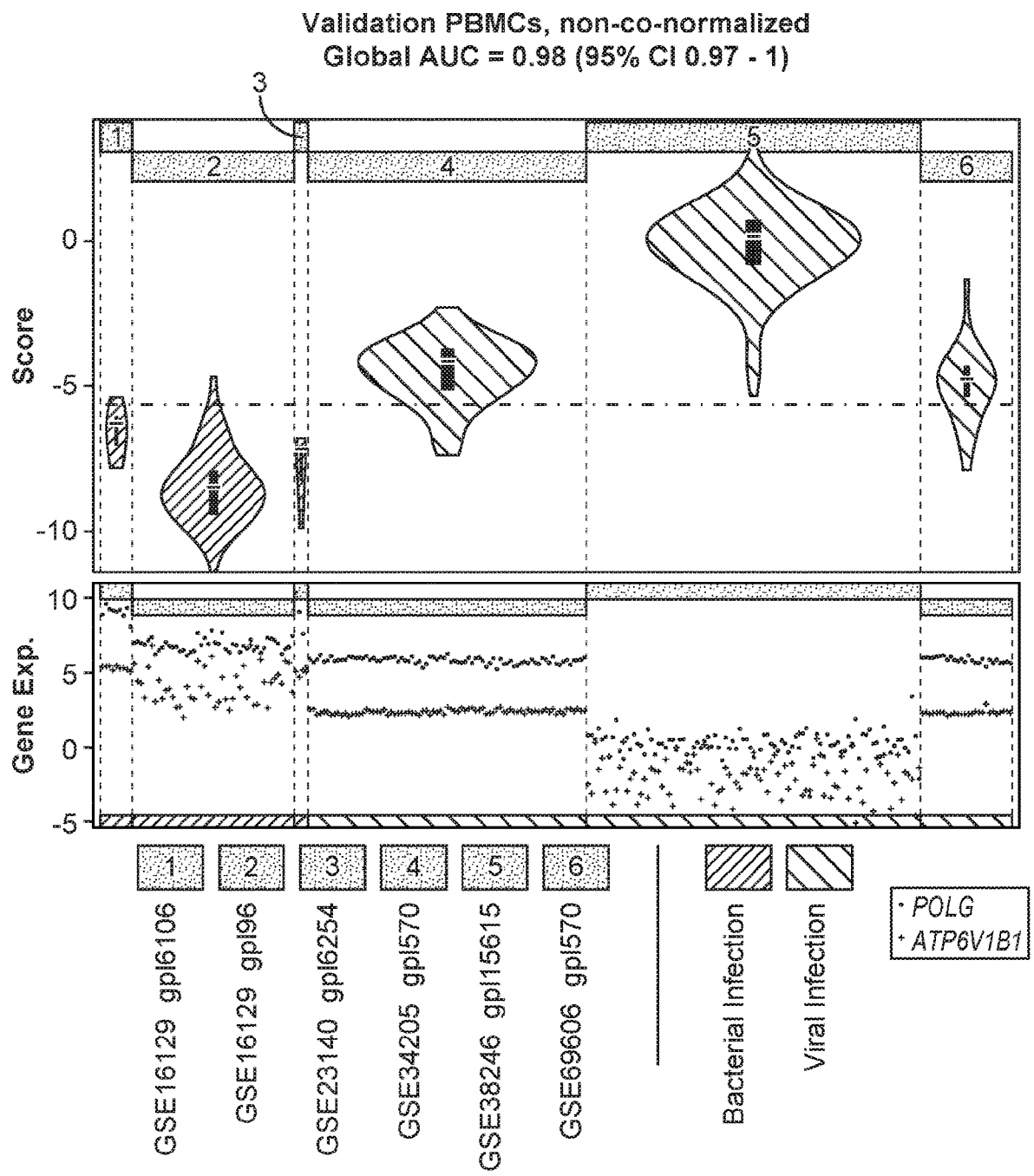
FIG. 17 shows the bacterial/viral score in global ROC of non-co-normalized PBMC validation datasets. PBMCs datasets are examined separately because PBMC datasets are expected to have different gene levels than whole blood. The score distribution by dataset (dark gray violins=bacterial, light gray violins=viral), individual gene levels, housekeeping genes (greyscale) are shown. The width of each violin corresponds to the distribution of scores within the given dataset. The vertical bar within each violin spans the 25th-75th percentile, and the middle white dash shows the mean score. Note the highly varying locations and scales of the housekeeping genes POLG and ATP6V1B1.

There are dozens of microarray cohorts in the public domain that studied either bacterial or viral infections, but not both, thus precluding a direct (within dataset) estimate of diagnostic power for separating bacterial and viral illness. In order to apply and compare a gene score across these cohorts, a new method was needed that could remove inter-dataset batch effects while remaining unbiased to the diagnosis of the diseased patients. Here we designed and implemented a new type of array normalization that uses the ComBat[32] empiric Bayes normalization methods on healthy controls to obtain bias-free corrections of disease samples (a method we call COmbat CO-Normalization Using conTrols, or 'COCONUT', Methods section below, and FIG. 11). Importantly, housekeeping genes are invariant across both diseases and cohorts after COCONUT co-normalization, while each gene still retains the same distribution between diseases and controls within each dataset (FIGS. 12A and 12B). Since the method assumes that all healthy samples are derived from the same distribution, we split the whole blood and PBMC samples, since different immune cell types have significantly different baseline gene expression distributions. Using COCONUT co-normalization, we were able to show that the bacterial/viral metascore has a global AUC of 0.92 (95% CI 0.89-0.96) in the discovery cohorts (FIG. 2, pre-normalized data in FIG. 14). We then applied this method to test the bacterial/viral metascore in all public-domain microarray cohorts that matched inclusion criteria and used whole blood (including the 4 direct validation cohorts that included control patients plus 20 cohorts that measured either bacterial or viral infections but not both[33-49], N=143+897=1,040), and showed an overall ROC AUC=0.93 (95% CI 0.91-0.94) across these data (Table 2, FIG. 13, pre-normalized data in FIG. 15). Particularly remarkable is the wide clinical variety of the data, which include a wide range of types of infections (Gram positive, Gram negative, atypical bacterial, common respiratory viruses, and dengue) and severities (mild infections to septic shock). We were thus able to establish a single cutoff across all cohorts (shown as horizontal dotted line). Finally, we separately performed the same procedure on the available PBMC validation cohorts (6 cohorts[50-54], N=259, global AUC=0.92 (95% CI 0.87-0.97, FIG. 16, pre-normalized data in FIG. 17). Remarkably, all three global ROC AUCs using COCONUT co-normalization (discovery whole blood=0.92, validation whole blood=0.93, validation PBMCs=0.92) roughly matched the summary AUC of the direct validation cohorts (0.91), giving high confidence in this level of diagnostic power.

Figure 18:
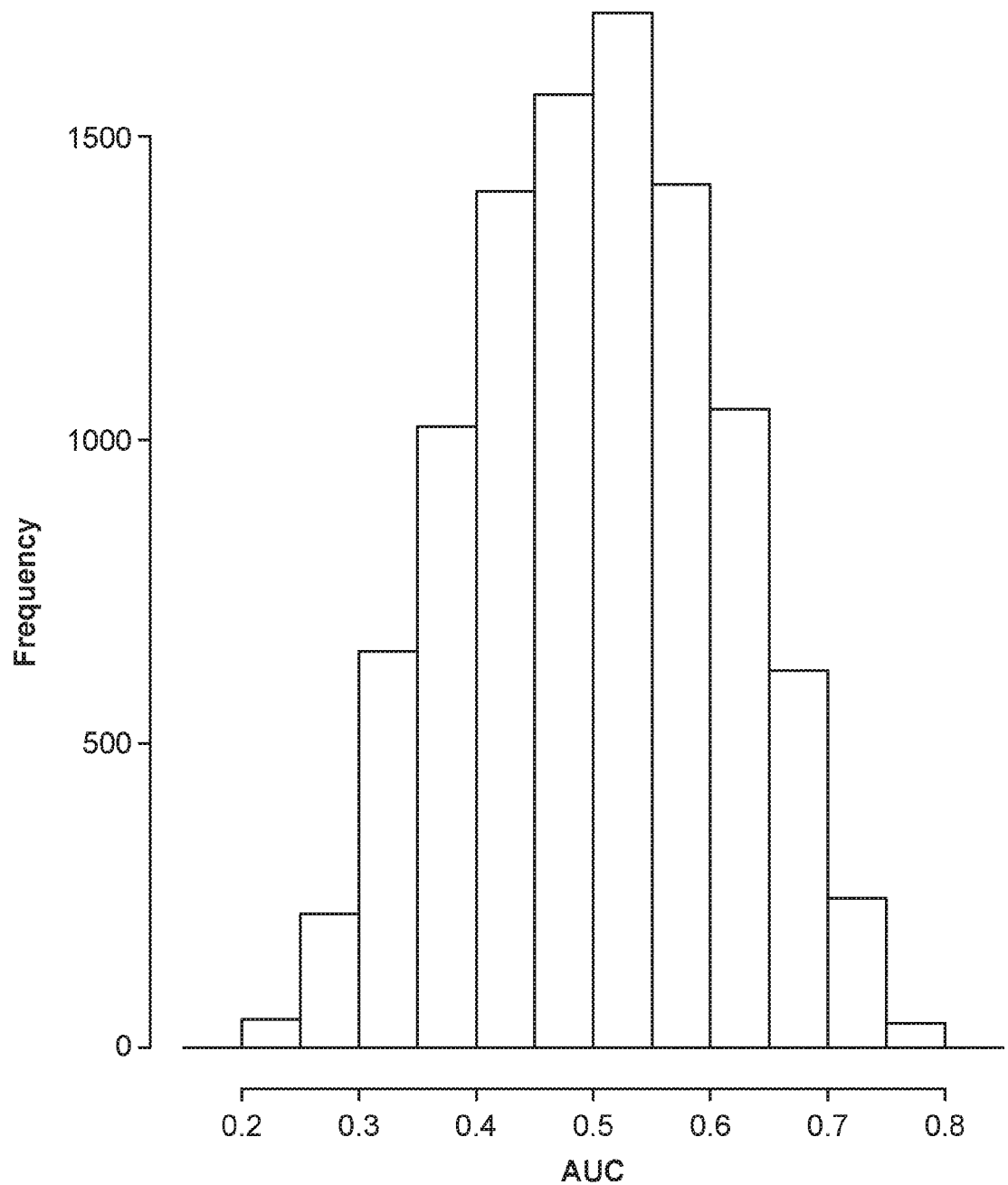
FIG. 18 shows the distribution of mean AUCs across all discovery datasets for 10,000 randomly chosen 2-gene pairs.

Supplemental Table 4 shows bacterial/viral metascores for all combinations of two (2) genes selected from the 71 gene set obtained by iterating the greedy forward algorithm in discovery datasets. All the 2-gene combinations from the 71 gene set show an obtained mean AUC greater than or equal to 0.80 (>0.80). In comparison, FIG. 18 shows the distribution of mean AUCs in discovery datasets for ten thousand (10,000) randomly chosen 2-gene pairs, showing that an AUC of greater than or equal to 0.80 is not attainable by chance alone. As illustrated in FIG. 18, the randomly chosen 2-gene pairs result in a normal distribution of mean AUCs bounded by greater than 0.2 (>0.20) and less than 0.80 (<0.80). The 2-gene combinations provided in Supplemental Table 4 with an AUC of equal or greater than 0.80 (≥0.80) have a clinically useful determination of whether an infection is viral or bacterial.

Integrated Antibiotic Decision Model

Figure 3A:
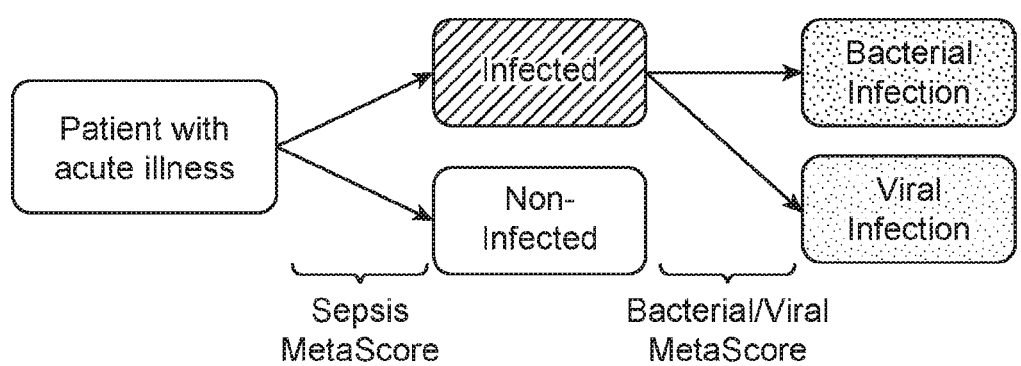
Figure 3B:
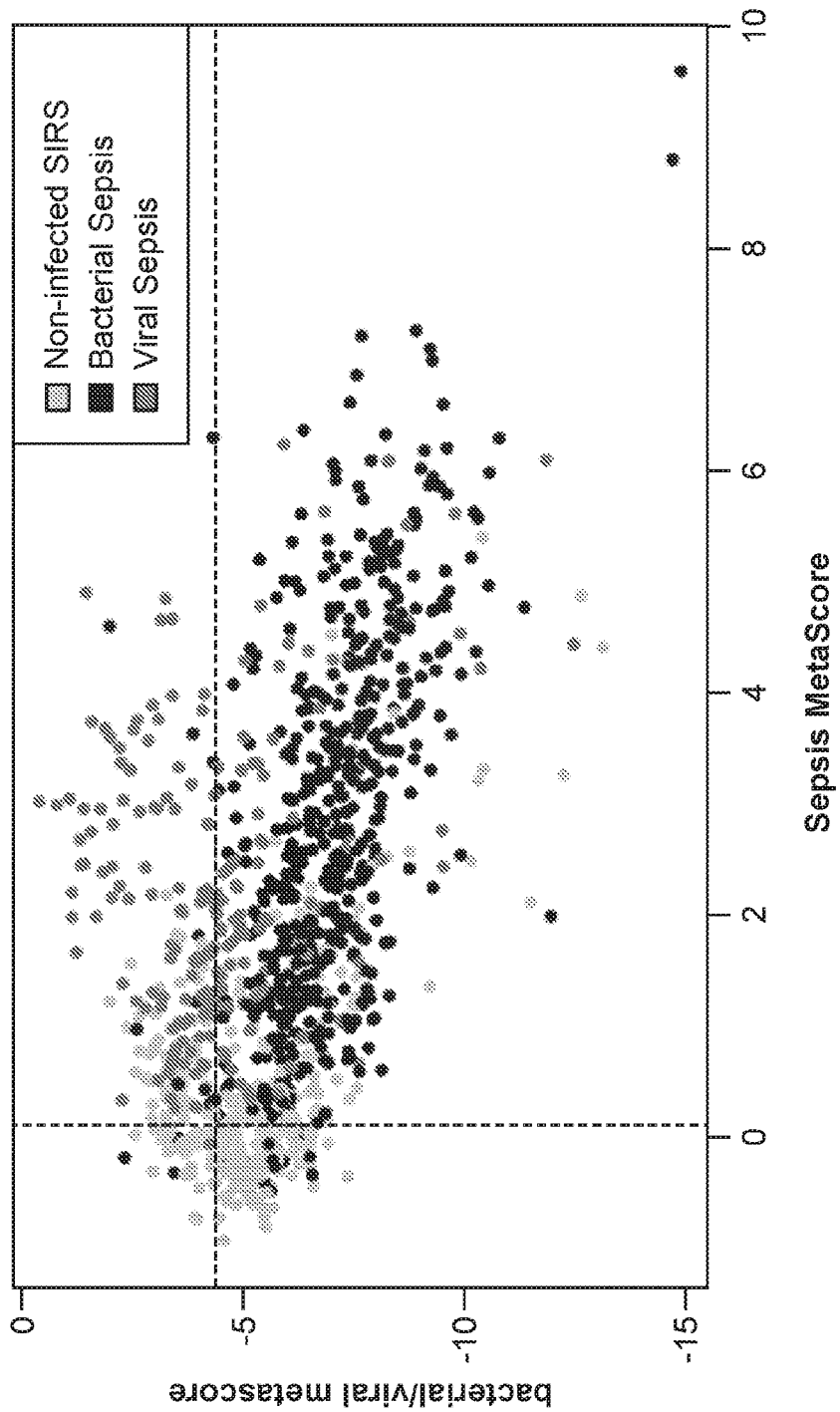
Figure 4B:
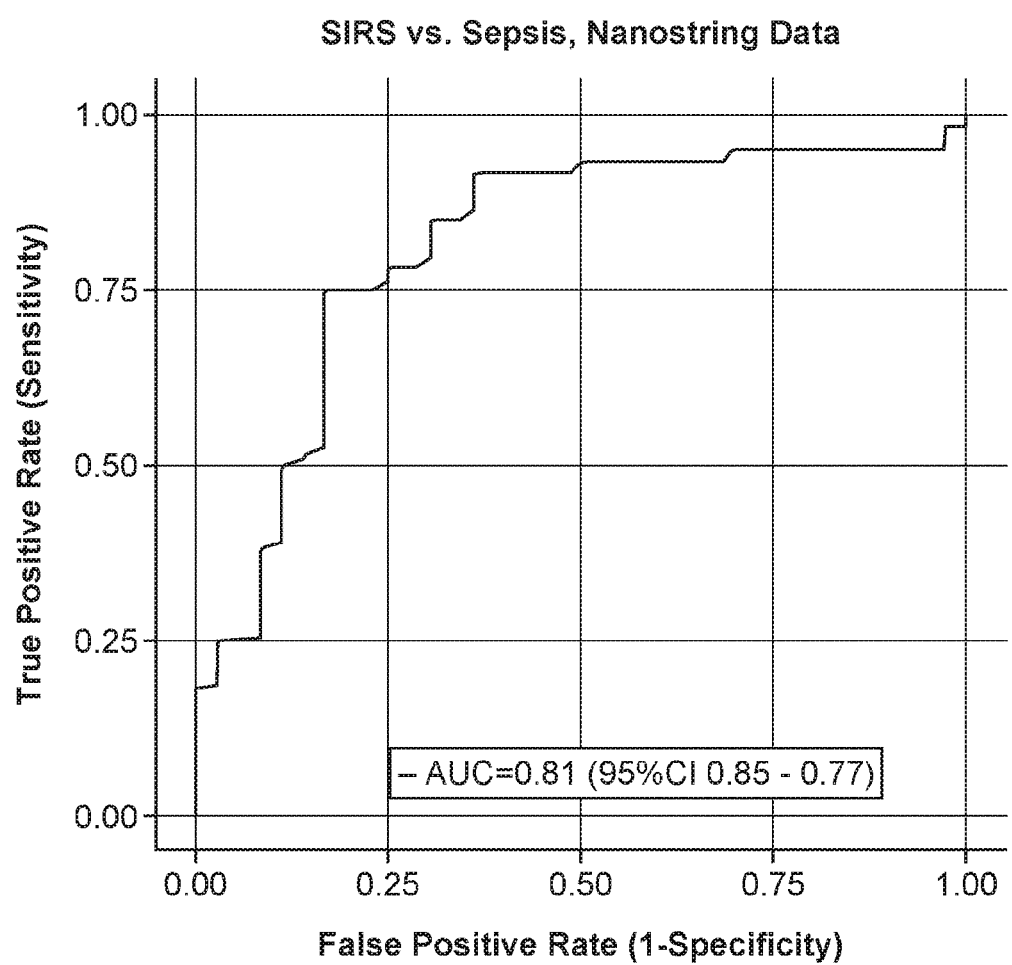
Figure 4C:
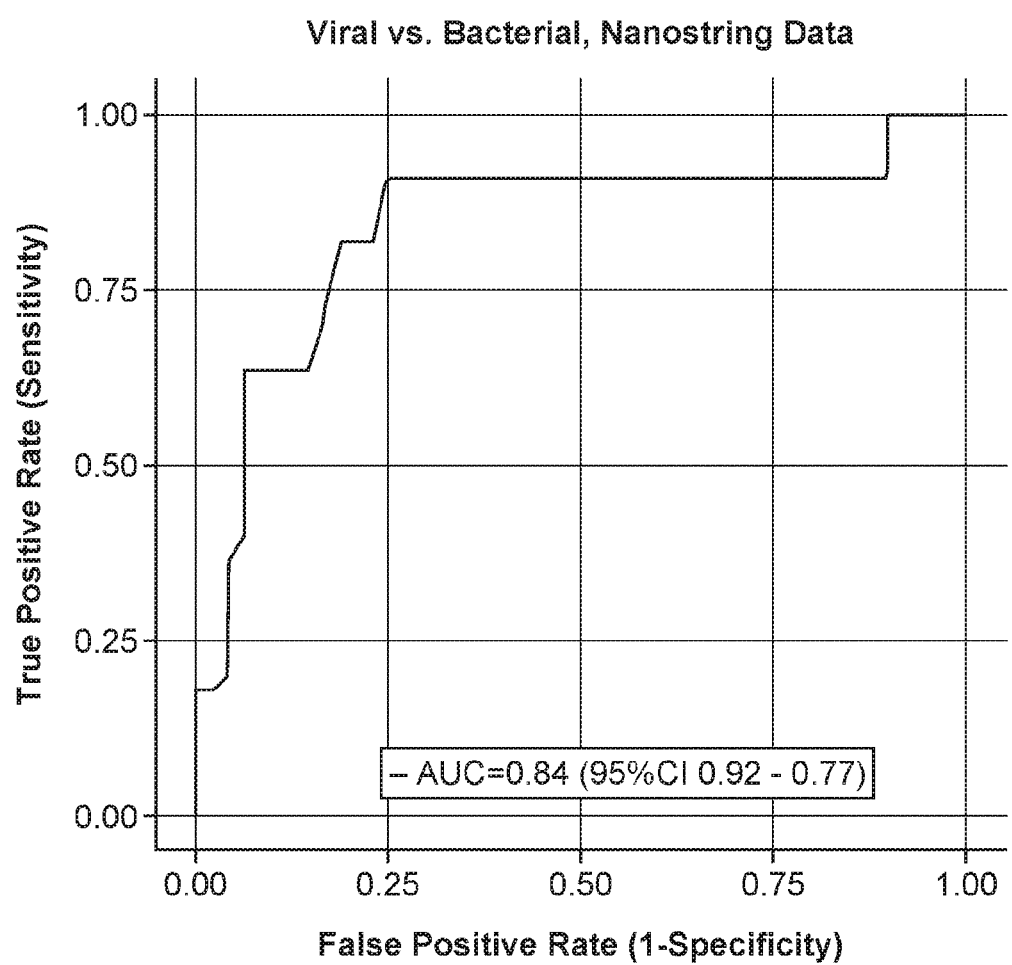
Figure 4D:
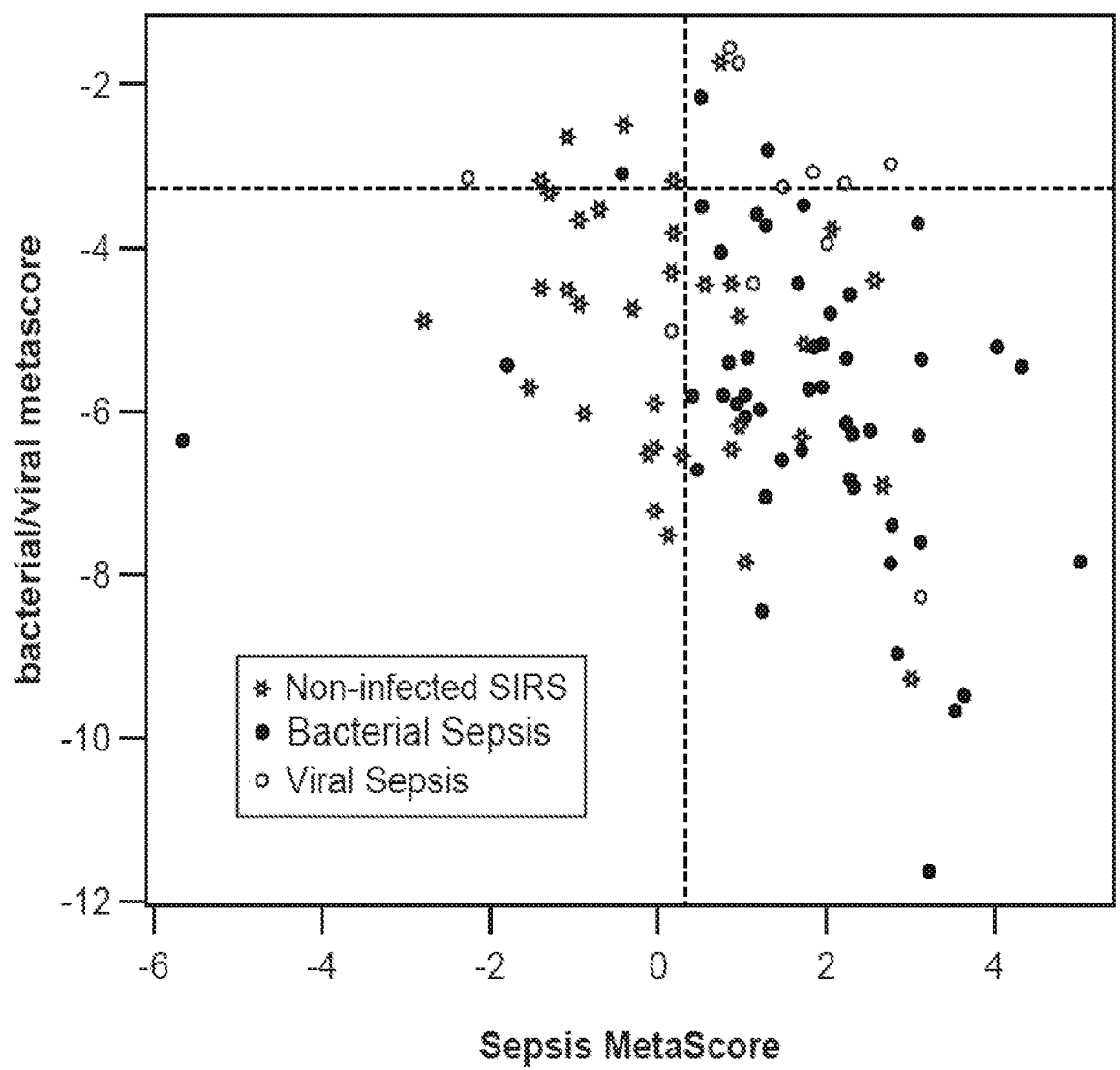
Figure 19A:
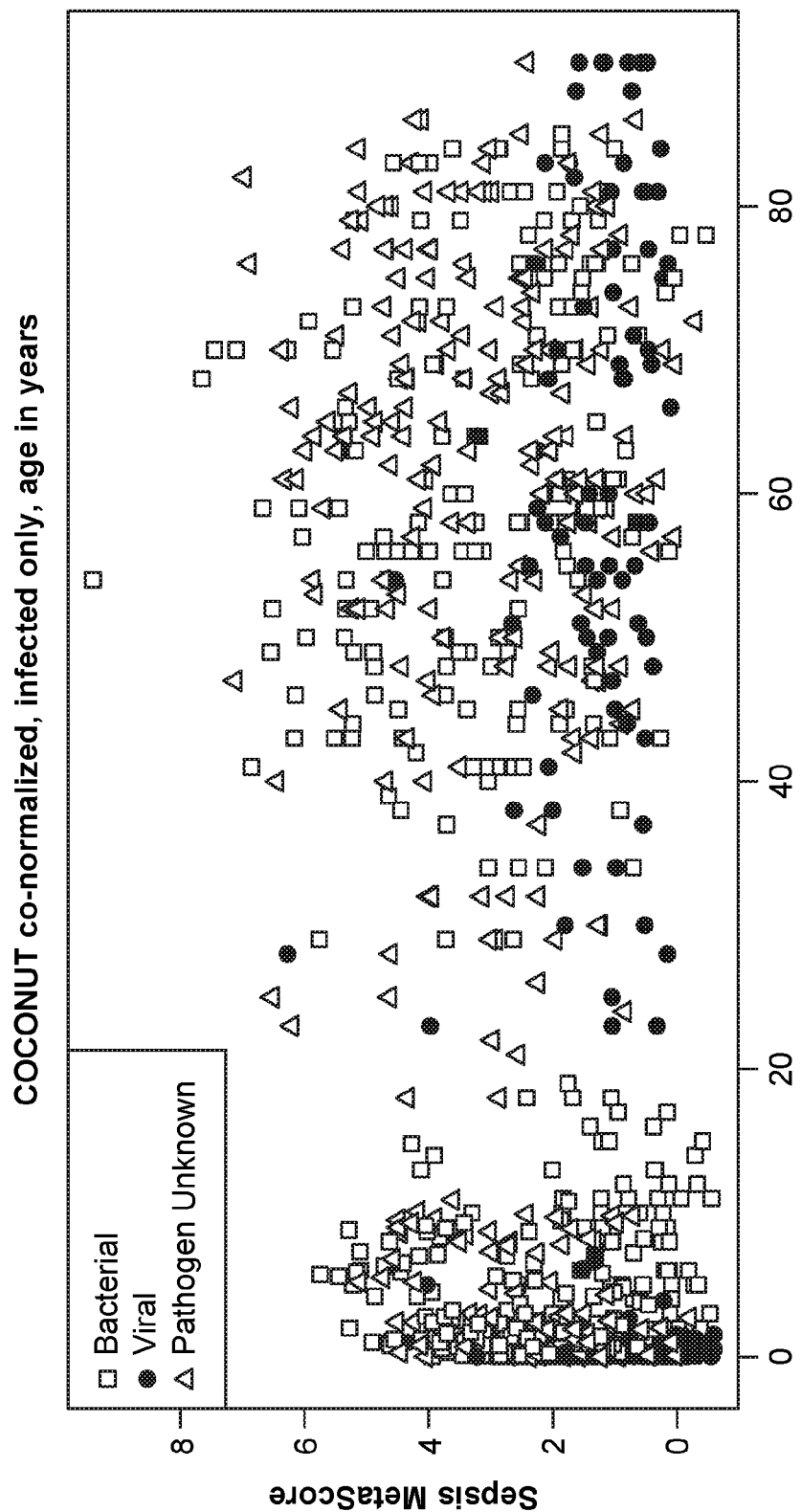
FIGS. 19A-19D show the effects of age on the Sepsis MetaScore in COCONUT co-normalized data.
Figure 19B:
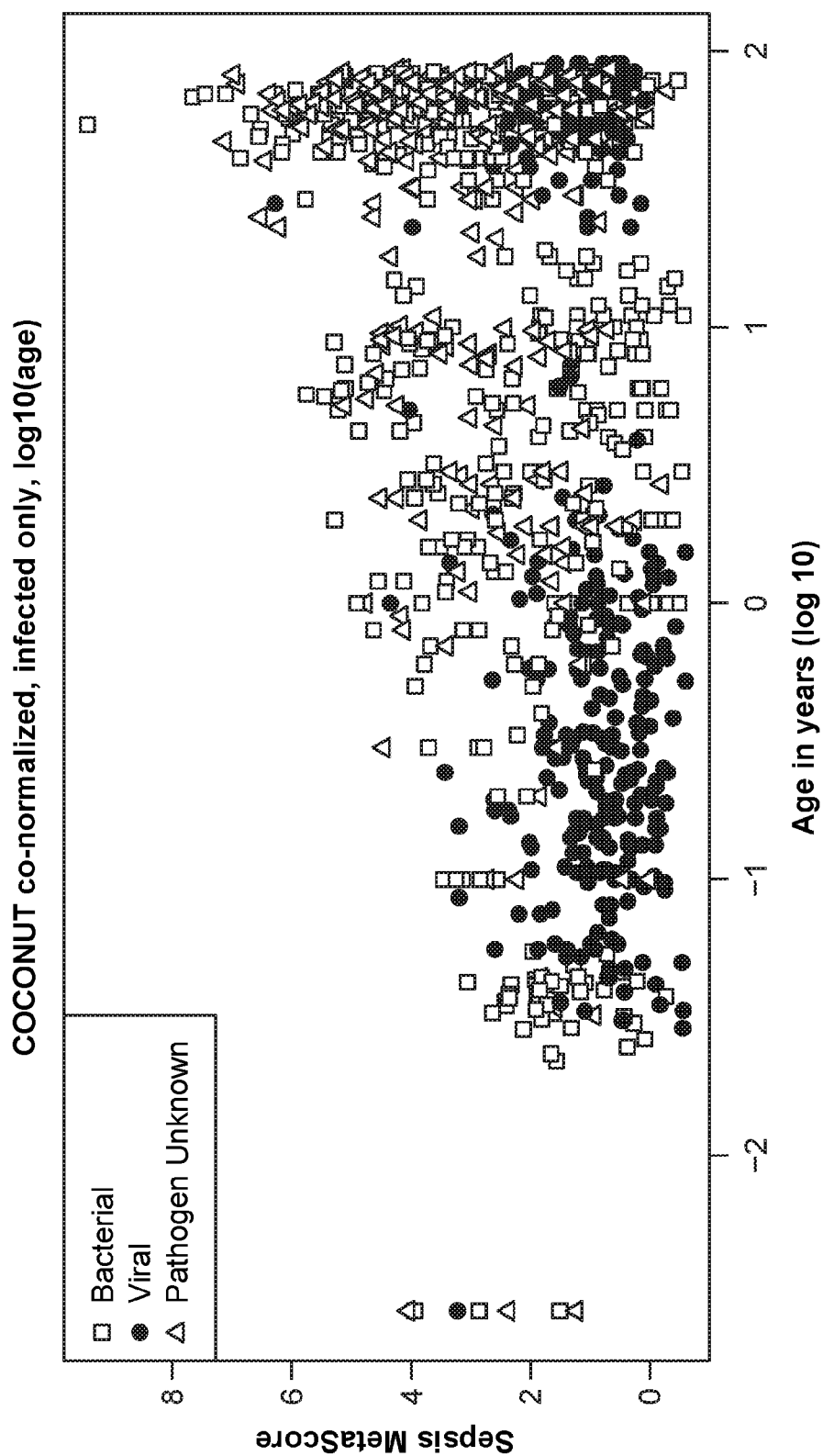
Figure 19C:
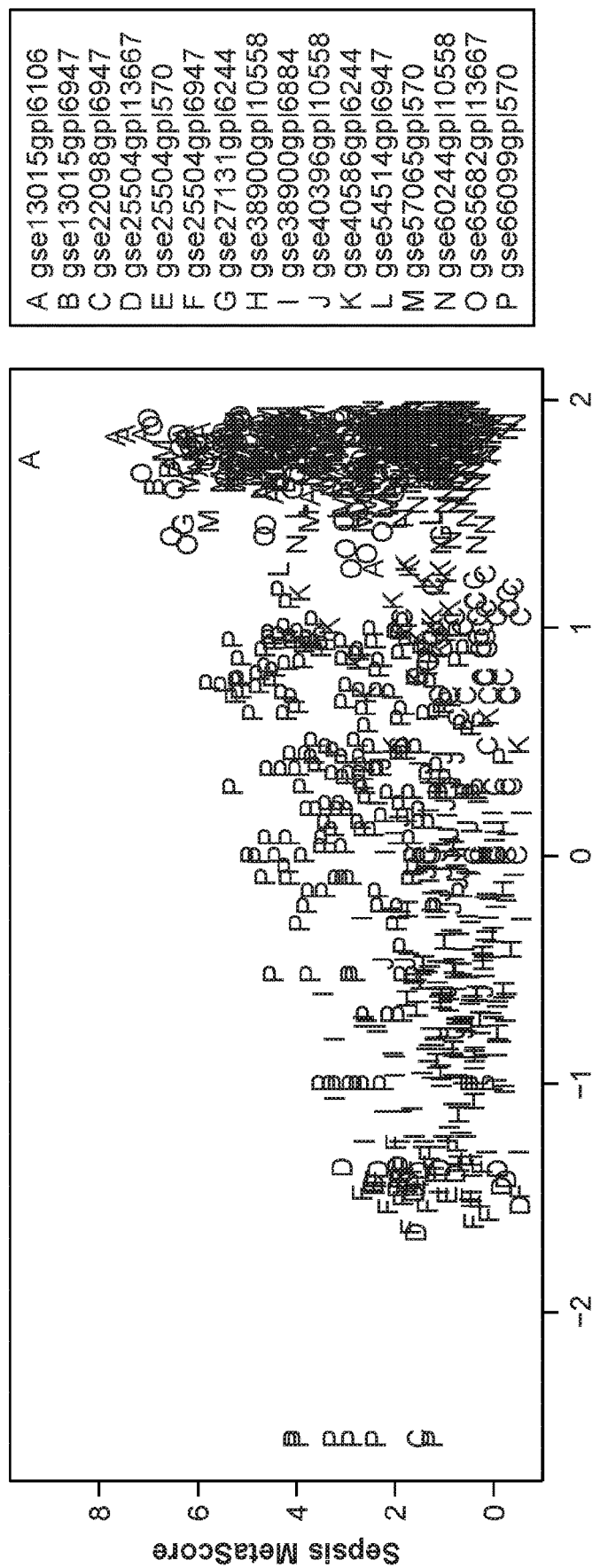
Figure 19D:
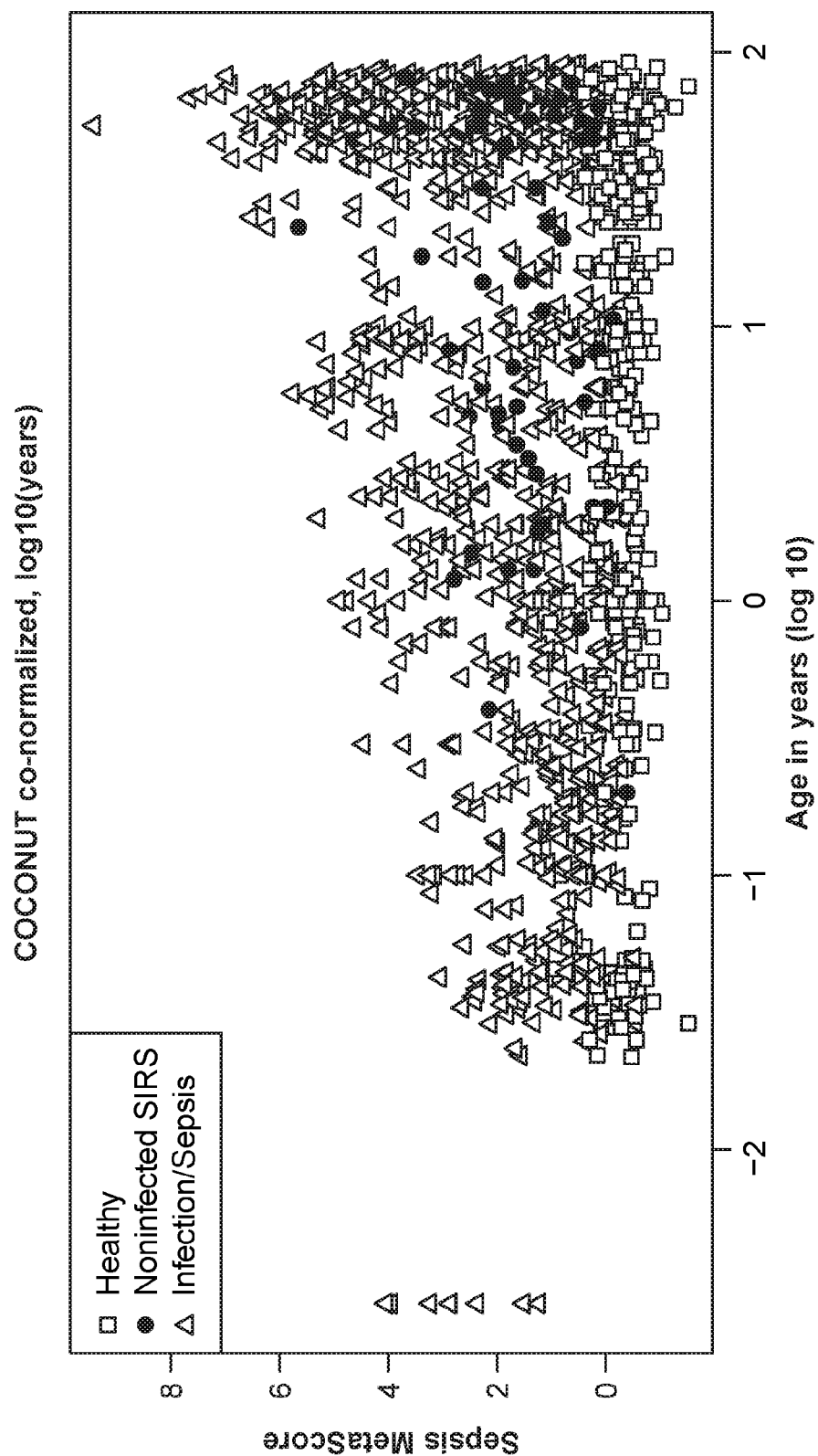
Figure 20A:
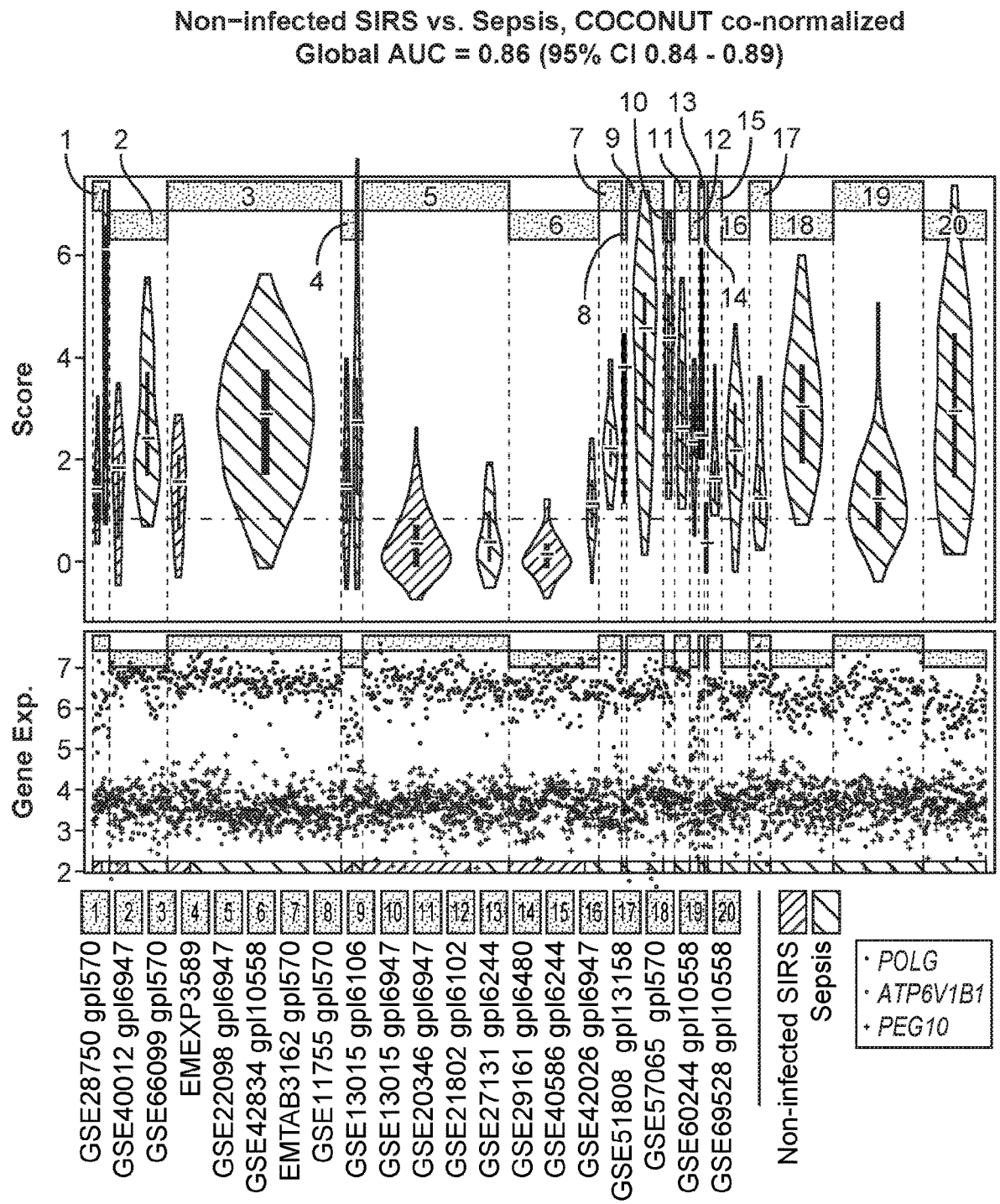
FIGS. 20A and 20B show the Sepsis MetaScore across all whole blood data (both discovery and validation) before (FIG. 20B) and after COCONUT co-normalization (FIG. 20A). The global AUC is 0.86 (95% CI 0.84-0.89) after COCONUT co-normalization. The score distribution by dataset (light gray violins=non-infected inflammation, dark gray violins=infections/sepsis) and housekeeping genes (greyscale) are shown. The dotted line shows a possible global threshold. The width of each violin corresponds to the distribution of scores within the given dataset. The vertical bar within each violin spans the 25th-75th percentile, and the middle white dash shows the mean score. Note the invariance of the housekeeping genes POLG, ATP6V1B1, and PEG10 across datasets in FIG. 20A post-COCONUT-normalization, with highly varying locations and scales of the housekeeping genes prior to normalization in FIG. 20B.
Figure 20B:
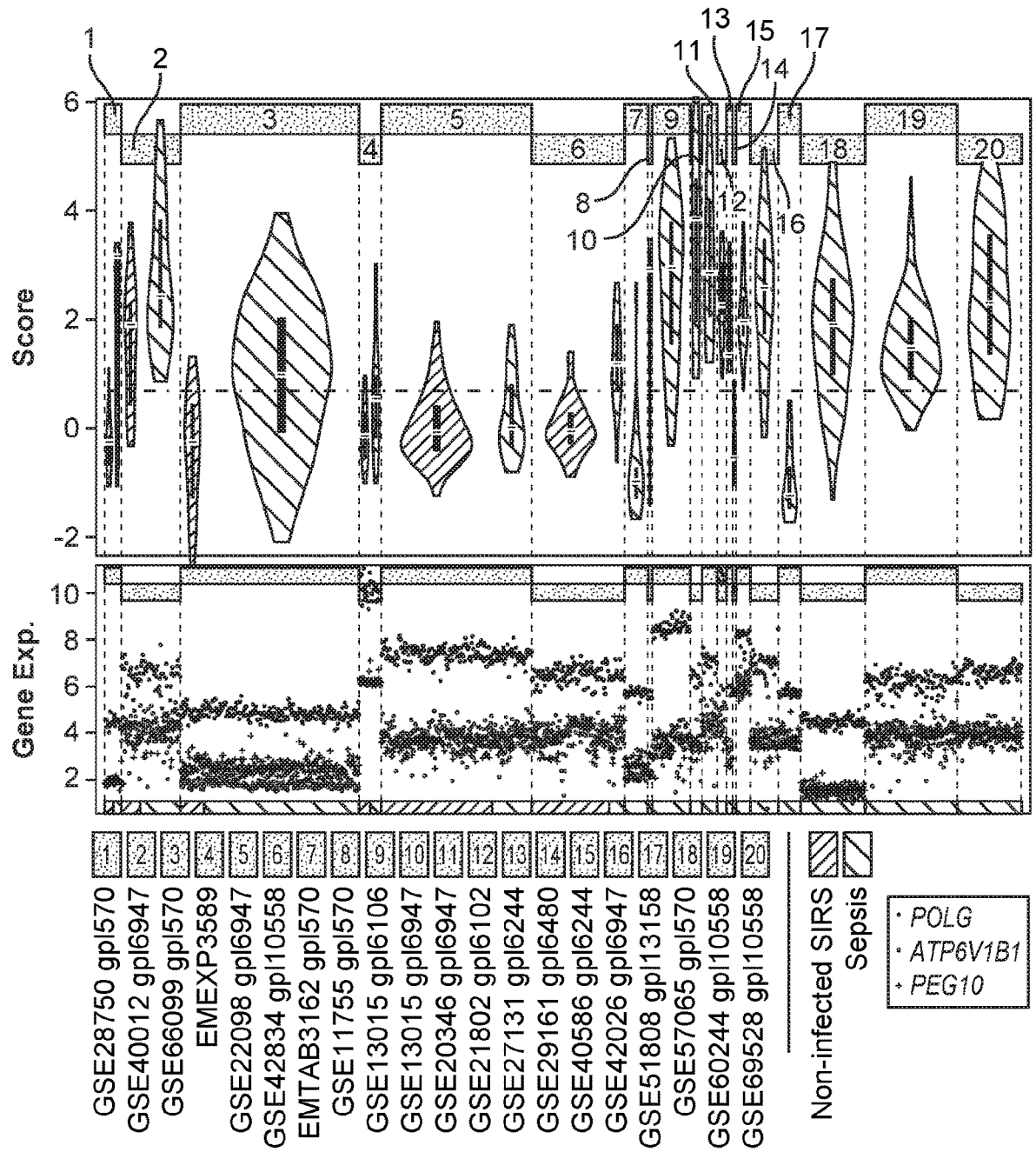
Figure 21A:
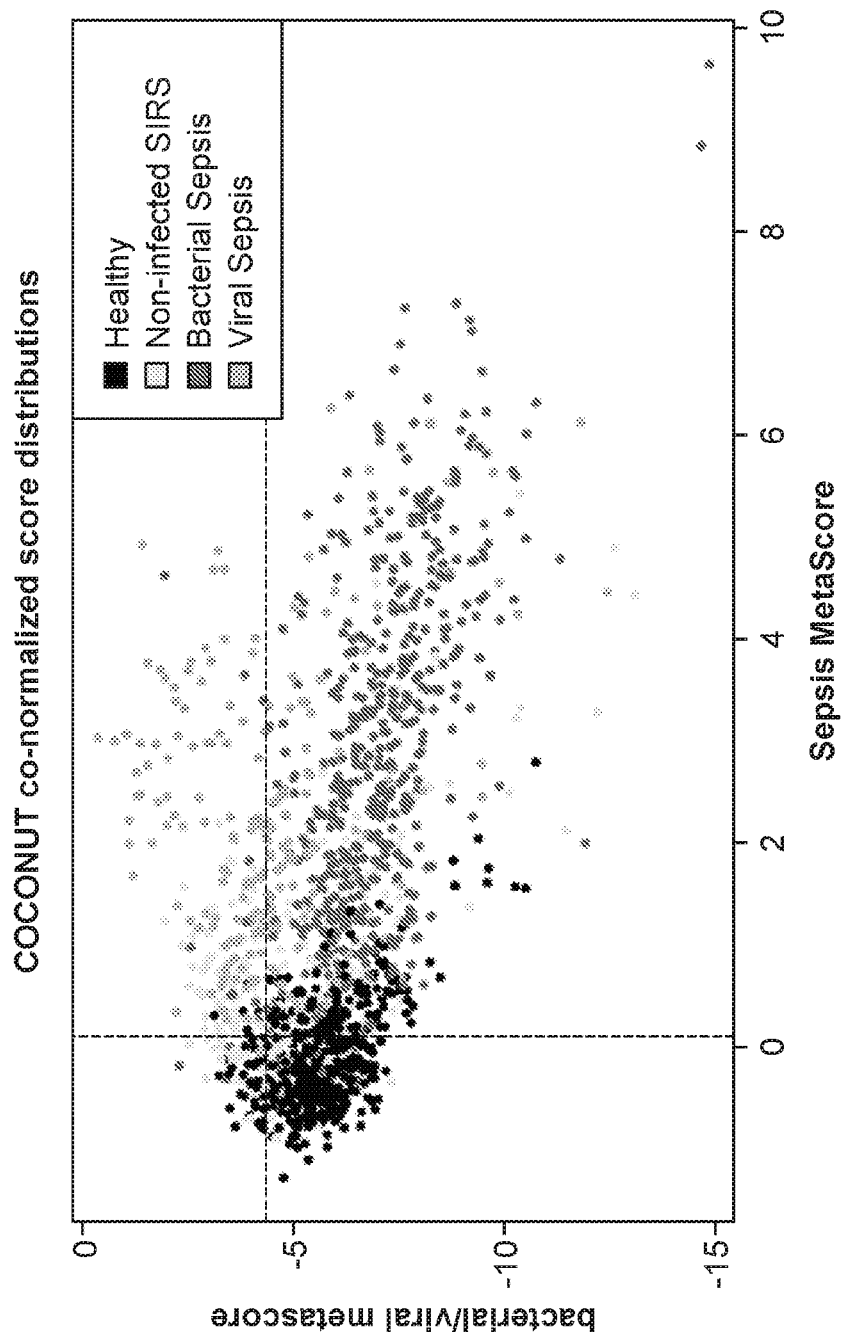
Figure 22:
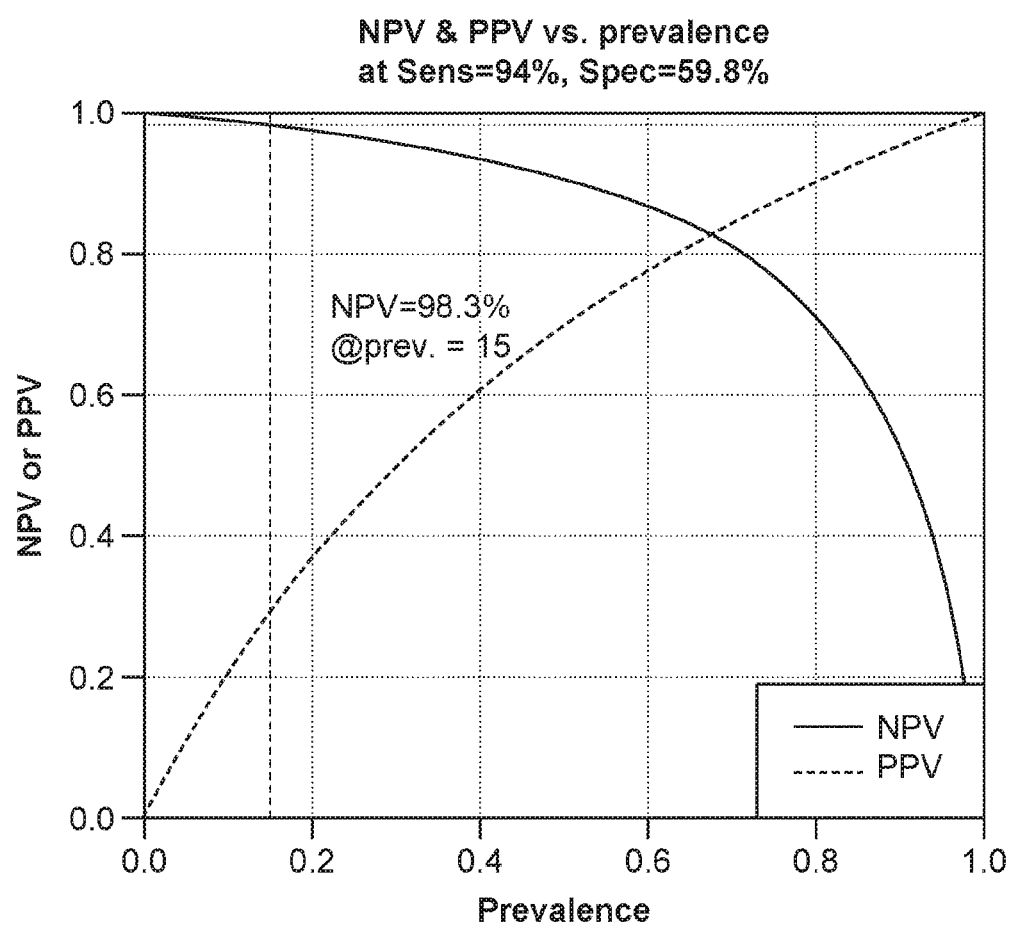
FIG. 22 shows NPV and PPV versus prevalence for a diagnostic test with 94.0% sensitivity and 59.8% specificity. Red lines show an NPV of 98.3% at a prevalence of 15%, as a rough estimate for real case-rates of infection.
Figure 23A:
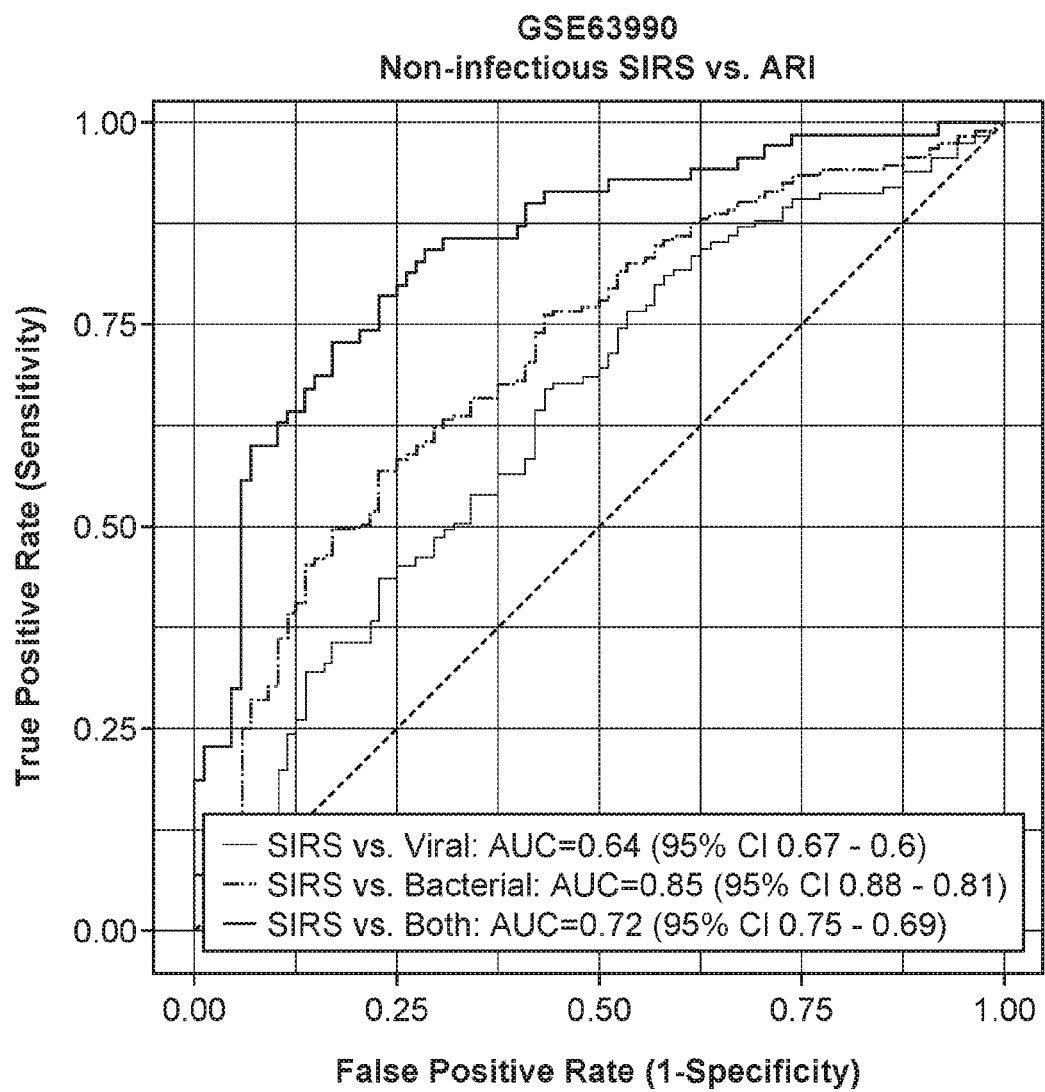
Figure 23B:
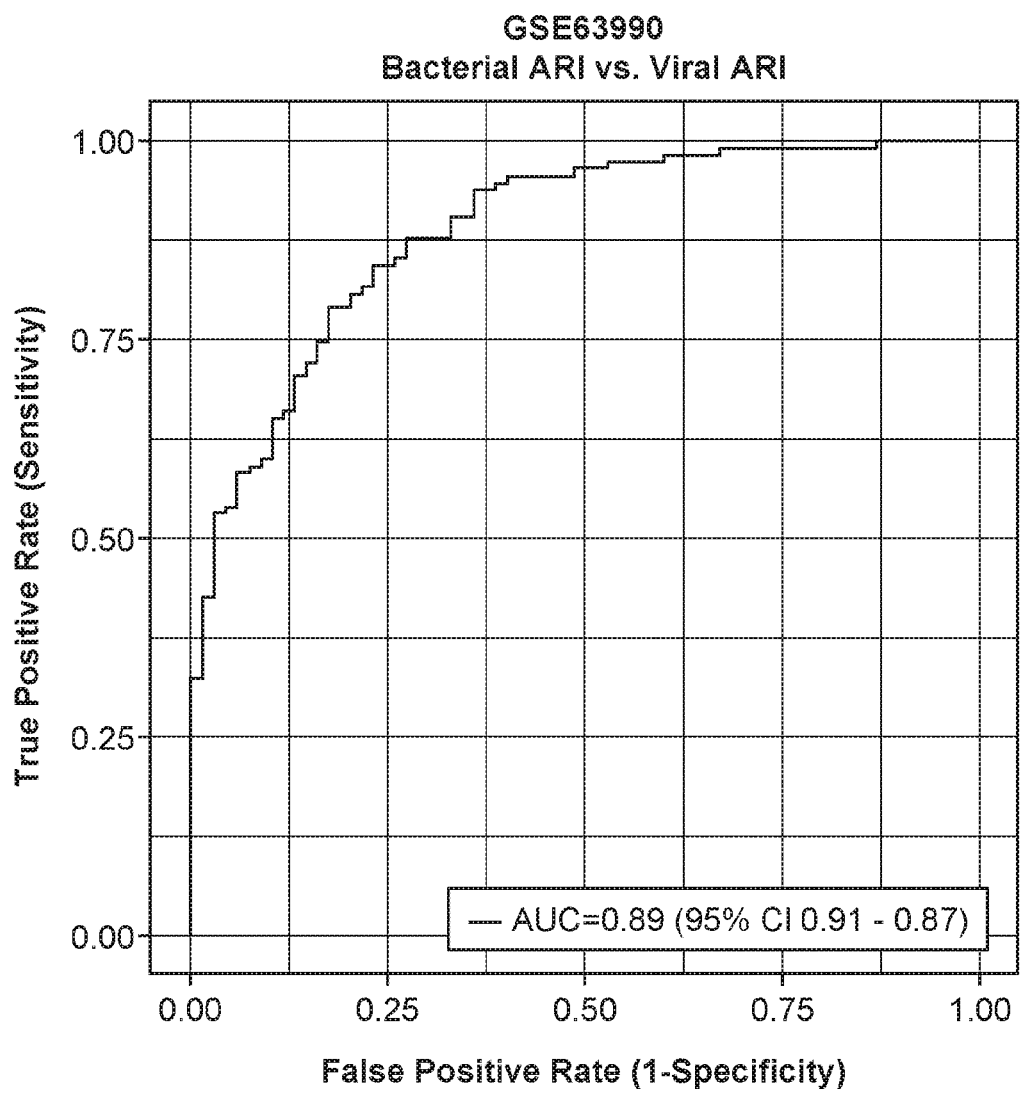
Figure 23C:
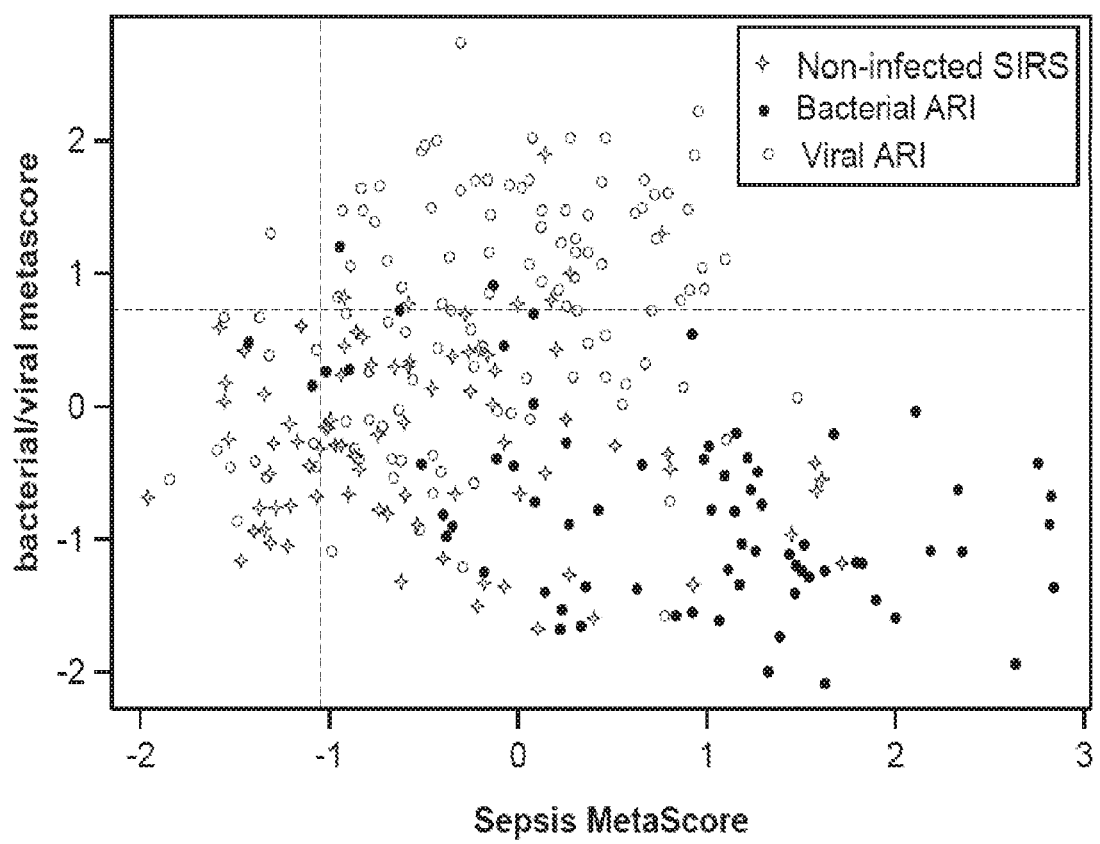

A key clinical need is diagnosing whether a patient with signs and symptoms of inflammation has an underlying bacterial infection, as rapid and judicial administration of antibiotics is key to improving patient outcomes. Neither the SMS nor the bacterial/viral metascore alone can robustly distinguish between all three classes of (1) non-infected inflammation, (2) bacterial illness and (3) viral illness. Thus, to increase clinical relevance, we tested an "integrated antibiotics decision model" (IADM), whereby we first apply our previously-described SMS[7] to test for the presence of an infection, and then the samples that test positive for infection are tested with the bacterial/viral metascore (FIG. 3A). As above, the only way to establish test characteristics for the IADM simultaneously across cohorts is to use COCONUT co-normalization. However, we found that the SMS in COCONUT co-normalized data is strongly influenced by age, which could be due either to differences between healthy patients or infected patients, or both (FIGS. 19A and 19B). We thus excluded cohorts focused on infants (children<1 year old) from the IADM, resulting in a total of 20 cohorts (N=1,057). The resulting global AUC for the SMS across the available data was 0.86 (95% CI 0.84-0.89) (Supplemental Table 2, FIGS. 20A and 20B). We set global thresholds for a SMS sensitivity for infection of 95% and a bacterial/viral metascore sensitivity for bacterial infection of 95%. This yielded an overall sensitivity and specificity for bacterial infections of 94.0% and 59.8%, respectively, and for viral infections 53.0% and 90.6%, respectively (FIGS. 3A-3C). These were largely unchanged if healthy patients were included in the non-infected class (FIGS. 21A and 21B). The overall positive and negative likelihood ratios for bacterial infection in the IADM are thus 2.34 (LR+) and 0.10 (LR−); a recent meta-analysis of procalcitonin showed a negative LR of 0.29 (95% CI 0.22-0.38)[55]. We plotted NPV and PPV vs. prevalence for these test characteristics; the NPV and PPV for bacterial infection at a prevalence of 15% are 98.3% and 29.2% (FIG. 22).

There was only one dataset (GSE63990[14]) which included non-infected SIRS patients and patients with both bacterial and viral illness but did not include healthy controls, precluding its addition to the global calculations. We thus tested the IADM with locally derived test thresholds. We found an overall bacterial infection sensitivity and specificity of 94.3% and 52.2%, respectively (FIGS. 21A and 21B).

NanoString Validation

Finally, we used targeted NanoString nCounter[56] gene expression assays to validate these results in independent whole blood samples from children with sepsis from the Genomics of Pediatric SIRS and Septic Shock Investigators (GPSSSI) cohort (total N=96, with 36 SIRS, 49 bacterial sepsis, and 11 viral sepsis patients, FIGS. 4A-4E). The GPSSSI cohort was also utilized by dataset GSE66099, but the children profiled here were never profiled via microarray and so are not part of the discovery datasets. In the NanoString validation cohort, the SMS AUC was 0.81 (AUC 0.80 in GSE66099). Similarly, the bacterial/viral metascore AUC was 0.84 (AUC 0.83 in GSE66099). The microarray AUCs are thus preserved when tested with a targeted gene expression assay in new patients. Applying the same IADM, the sensitivity and specificity for bacterial infections were 89.7% and 70.0%, and for viral infections were 54.5% and 96.5%, respectively.

Discussion

Better diagnostics for acute infections are needed in both the inpatient and outpatient setting. In low-acuity outpatient settings, a simple diagnostic that can discriminate bacterial from viral infections may be enough to assist in appropriate antibiotic usage. In higher-acuity settings, causes of non-infectious inflammation become more important to rule out, and so a decision model for antibiotic prescriptions must include a non-infected (non-healthy) case. Thus, a reliable diagnostic needs to distinguish all three cases (non-infected inflammation, bacterial infection, and viral infection). Here, using 426 samples from 8 cohorts, we derived a set of just 7 genes that can accurately discriminate bacterial from viral infections across a very broad range of clinical conditions in independent cohorts (total 30 cohorts composed of 1,299 patients). We further demonstrate that by coupling our prior Sepsis MetaScore (to distinguish presence or absence of infection) with this new bacterial/viral metascore (to determine infection type) into a single integrated antibiotics decision model, we can determine with high accuracy which patients would benefit from antibiotics. Finally, we confirmed the diagnostic power of both the 7-gene set and the IADM in independent samples using a targeted NanoString assay, showing that the signatures retain diagnostic power when not relying on microarrays.

The IADM has a low negative likelihood ratio (0.10) and high estimated NPV, meaning it would be potentially effective as a rule-out test. Notably, a meta-analysis of procalcitonin that included 3,244 patients from 30 studies resulted in an overall estimated negative likelihood ratio of 0.29 (95% CI 0.22-0.38)[55]. Thus, the IADM negative likelihood ratio is significantly lower than the estimate for procalcitonin. Moreover, these test characteristics assume no knowledge of the patient and so are only estimates of the real-world clinical utility of such a test. History and physical, vital signs, and laboratory values would all assist in a diagnosis as well. Even given these caveats, a recent economic decision model of screening ICU patients for hospital-acquired infections suggested that a test such as the IADM that can accurately diagnose bacterial and viral infections could be cost-effective[57]. Ultimately, only interventional trials will be able to establish cost-effectiveness and clinical utility of a new diagnostic.

We validated our diagnostic in pediatric sepsis patients from the GPSSSI cohort using a NanoString assay. NanoString is highly accurate and is a useful tool for measuring the expression levels of multiple genes at once; however, it is also likely too slow for clinical application (4-6 hours per assay). Thus, although the assay confirms that our gene set is robust in targeted measurements, further work will be needed to improve the turnaround time. There are multiple possibilities for an eventual commercial product based on rapid multiplexed qPCR. However, this technical hurdle is something that all gene expression infection diagnostics must overcome in order to gain clinical relevance.

Several groups have published models for diagnosing infections based on host gene expression; none have yet made it into clinical practice. Most prior classifiers were either not tested in multiple independent cohorts, had too many genes to allow rapid profiling necessary for useful diagnosis, or both. For instance, Suarez et al. created a 10-gene K-nearest-neighbor classifier, but did not test it outside their published dataset (GSE60244)[13]. Tsalik et al. created a 122-probe (120 gene) classifier based on multiple regression models, but in testing it in external GEO cohorts, they retrained their regression coefficients in each new dataset[14]. Such model re-training leads to a strong upward bias to these validation numbers (assuming that a final model would not be locally re-trained), or suggests that each new clinical site would have to gather a large prospective cohort to train the model prior to implementation. Other groups have made gene expression classifiers for sepsis, but did not include models for discriminating viral infections[7,9,10]. Our new IADM is robust across a wide range of disease types and severities, but has a relatively lower sensitivity for viral infections. Non-gene expression biomarkers have also been used for infection diagnosis. Procalcitonin has been studied extensively in the setting of sepsis diagnosis, but cannot distinguish between non-infected individuals and those with viral infections[58]. Protein-panel assays have been shown to discriminate bacterial from viral infections, but cannot discriminate patients with non-infectious inflammation[59,60]. Thus all of these classifiers have certain strengths and weaknesses that will become more apparent with further prospective testing and direct comparison.

Although our goal in this study was to identify new biomarkers and not necessarily new biology, it is still important for a biomarker set to have biologic plausibility. Of the seven genes in the bacterial/viral metascore, six have previously been linked to infections or leukocyte activation. Both IFI27 and JUP were shown in single-cohort genome-wide expression studies to be induced in response to viral infection[52,61], while TNIP1 and CTSB have been shown to be important in modulating the NF-kB and necrotic responses to bacterial infection[62,63]. Finally, LAX1 (upregulated in viral infections) is involved in activation of T-cells and B-cells[64], while HK3 is instrumental in the neutrophil differentiation pathway[65]. Thus the role of these transcripts as biomarkers for infection type is novel but not unprecedented.

Here we relied on a new method, COCONUT, to directly compare our model across an enormous pool of one-class cohorts that would otherwise be unusable for benchmarking a new diagnostic. COCONUT assumes that all controls come from the same distribution; that is, the genes in each group of controls are reset to have the same mean and variance, with batch parameters learned empirically from gene groups. This method corrects for microarray and batch processing differences between cohorts, and so allows for the creation of a global ROC curve with a single threshold. This is a more 'real-world' measure of diagnostic power than simply reporting multiple validation ROC curves, as no single cutoff could attain the same test characteristics in the different cohorts[16]. The most important takeaways from the COCONUT-co-normalized data are that both the bacterial/viral metascore and the IADM retain diagnostic power across a very broad range of infection types and severities, with overall AUCs that are similar to the summary AUCs from head-to-head comparisons within cohorts.

Overall, we have leveraged our proven multi-cohort analysis pipeline to derive a highly robust model for improving infection diagnosis. Using a new method, we were able to validate this in dozens of independent microarray cohorts. We have also validated using a targeted NanoString assay in pediatric sepsis patients. While the IADM still needs to undergo optimization for rapid turnaround as well as a prospective interventional trial, it seems clear that molecular profiling of the host genome will become part of the clinical toolkit in the future.

One of skill in the art will understand that alternative methods to the bacterial/viral metascore can be used to develop a classifier capable of distinguishing between bacterial and viral infections. Any method of machine learning known in the art can be used to develop the classifier. The method of developing a classifier can include ensemble algorithms that are made of a multitude of algorithms such as logistic regression, support vector machines, and decision trees such as random forests and gradient boosted decision trees. The classification can be developed using neural networks, which include a large number of nodes arranged in layers, where the output from a node in the first layer is used as the input for a node in the next layer. Alternatively, the classification can be developed using a support vector machine model, which is a representation of the examples as points in space, mapped so that the examples of the separate categories are divided by a clear gap that is as wide as possible. New examples are then mapped into the same space and predicted to belong to a category based on which side of the gap the new examples fall on. One of skill in the art will understand that any number of machine learning algorithms can be used to develop a classification capable of distinguishing between a bacterial and viral infection.

Methods

Systematic Search and Multi-Cohort Analysis

We performed a systematic search in NIH GEO and EBI ArrayExpress for public human microarray genome-wide expression studies using the search terms: bact[wildcard], vir[wildcard], infection, sepsis, SIRS, ICU, nosocomial, fever, pneumonia. Abstracts were screened to remove all studies that were either (1) non-clinical, (2) performed using tissues other than whole blood or PBMCs, or (3) compared patients that were not matched for clinical time.

All microarray data were re-normalized from raw data (when available) using standardized methods. Affymetrix arrays were renormalized using gcRMA (on arrays with perfect-match probes) or RMA. Illumina, Agilent, GE, and other commercial arrays were renormalized via normal-exponential background correction followed by quantile normalization. Custom arrays were not renormalized. Data were log2 transformed, and a fixed-effect model was used to summarize probes to genes within each study. Within each study, cohorts assayed with different microarray types were treated as independent.

We performed multi-cohort meta-analysis as previously described[7,15,16,27]. Briefly, genes were summarized using Hedges' g, and the DerSimonian-Laird random-effects model was used for meta-analysis, followed by Benjamini-Hochberg multiple hypothesis correction[66]. Patients with bacterial infections were compared to patients with viral infections within studies, such that a positive effect size indicates a gene was more highly expressed in virus-infected patients, and a negative effect size indicates a gene was more highly expressed in bacteria-infected patients.

In order to find a set of genes highly conserved in differential expression between bacterial and viral infections, we selected all cohorts which directly compared patients with bacterial and viral infections. Patients with documented co-infections (i.e. both bacterial and viral) were removed. Cohorts were required to have>5 patients in each group to be included in meta-analysis. Both PBMCs and whole blood cohorts were included. Significant genes were those which had an effect size>2-fold and an FDR<1% in a leave-one-dataset-out round-robin analysis. However, in order to ensure that both tissue types were represented in the final gene set, we also performed separate meta-analyses of the PBMCs and whole blood cohorts, and removed all genes which had an effect size<1.5-fold in either tissue type separately. The remaining genes were considered significant.

Derivation of 7-Gene Set

To find a set of highly diagnostic genes, the significant genes from the meta-analysis were run through a greedy forward search as previously described. Briefly, this algorithm starts with zero genes and in each cycle adds one gene that best improves the AUC for diagnosis in the discovery cohorts, until a new gene cannot improve the discovery AUCs more than some threshold. The resulting genes are used to calculate a single 'bacterial/viral metascore', calculated as the geometric mean of the 'viral' response genes minus the geometric mean of the 'bacterial' response genes, times the ratio of the number of genes in each set. The resulting continuous score can then be tested for diagnostic power using ROC curves.

Derivation of Additional Gene Sets

In order to identify additional diagnostic gene sets, we implemented a recursive greedy forward search whereby, at the algorithm's conclusion, the resulting diagnostic gene set was removed from the possible set of significant genes, and the algorithm was run again. The first gene set was taken for further validation, but the other gene sets were noted to perform similarly in the discovery cohorts (Supplementary Table 3).

Direct Validation of 7-Gene Set

The resulting gene set was first validated in the remaining public gene expression cohorts which directly compared bacterial to viral infections but were too small to use for the meta-analysis. Two cohorts (GSE60244[13] and GSE63990[14]) were made public after our meta-analysis was completed, and so were used for validation. To show generalizability, we also examined one large in vitro dataset comparing LPS to influenza exposure in monocyte-derived dendritic cells, but this was not included in the summary AUC as it is not expected to come from the same distribution as the clinical studies.

Summary ROC Curves

For both discovery and validation cohorts, summary ROC curves were constructed according to the method of Kester and Buntinx[67], and previously described[16]. Briefly, linear-exponential models are made of each ROC curve, and the parameters of these individual curves are summarized using a random-effects model to estimate the overall summary ROC curve parameters. The alpha parameter controls AUC (in particular, distance of the line from the line of identity) and the beta parameter controls skewness of the ROC curve. Summary AUC confidence intervals are estimated from the standard error of the alpha and beta in meta-analysis.

COCONUT Co-Normalization

There are dozens of public microarray cohorts that profiled patients with either bacterial or viral infections, but not both. It would be advantageous to be able to compare a gene score across these cohorts, but has not previously been possible because each different microarray has widely different background measurements for each gene, and among studies using the same types of microarrays there are large batch effects. In order to make use of these data, we needed co-normalize these cohorts in such a way that (1) no bias is introduced that could influence final classification (i.e., the normalization protocol should be blind to diagnosis); (2) there should be no change to the distribution of a gene within a study, and (3) a gene should show the same distributions between studies after normalization. A method with these characteristics would allow our gene score to be calculated and compared across multiple studies, and thus allow us to broadly test its generalizability.

Figure 10:
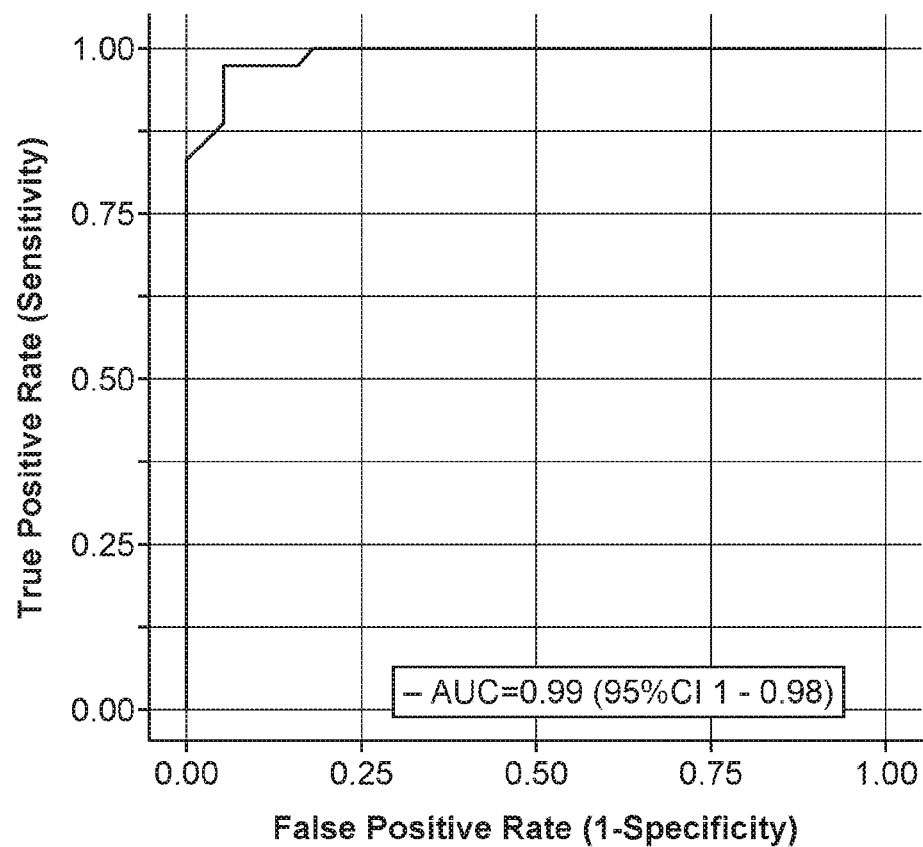
FIG. 10 shows the bacterial/viral metascore ROC in GSE53166, monocyte-derived dendritic cells stimulated in vitro with LPS or influenza virus, total N=75 (39 LPS, 36 influenza virus).

The ComBat empiric Bayes normalization method[32] is popular for cross-platform normalization, but crucially falls short of our desired criteria because it assumes an equal distribution across disease states. We thus developed a modified version of the ComBat method which co-normalizes control samples from different cohorts to allow for direct comparison of diseased samples from those same cohorts. We call this method COmbat CO—Normalization Using conTrols, or 'COCONUT'. COCONUT makes one strong assumption, which is that it forces control/healthy patients from different cohorts to represent the same distribution. Briefly, all cohorts are split into the healthy and diseased components. The healthy components undergo ComBat co-normalization without covariates. The ComBat estimated parameters $\hat{\alpha}$, $\hat{\beta}$, $\hat{\sigma}$, $\delta^*$, and $\gamma^*$ are obtained for each dataset for the healthy component, and then applied onto the diseased component (FIG. 10). This forces the diseased components of all cohorts to be from the same background distribution, but retains their relative distance from the healthy component (T-statistics within datasets are only different post-COCONUT due to floating-point math). Importantly, it also does not require any a priori knowledge of disease classification (i.e., bacterial or viral infection), thus meeting our prespecified criteria. This method does have the notable requirement that healthy/control patients are required to be present in a dataset in order for it to be pooled with other available data. Also, since healthy/control patients are set to be in the same distribution, it should only be used where such an assumption is reasonable (i.e., within the same tissue type, among the same species, etc.).

The ComBat Model and the COCONUT Method

As described by Johnson et al., the ComBat model corrects for location and scale of each gene by first solving an ordinary least squares model for gene expression, and then shrinking the resulting parameters using an empiric Bayes estimator, solved iteratively[32]. Formally, each gene expression level $Y_{ijg}$ (for gene g for sample j in batch i) is assumed to be composed of overall gene expression $\alpha_g$, design matrix of sample conditions X with regression coefficients $\beta_g$, additive and multiplicative batch effects $\gamma_{ig}$ and $\delta_{ig}$, and an error term $\varepsilon_{ijg}$:

$$Y_{ijg} = \alpha_g + X\beta_g + \gamma_{ig}\delta_{ig}\varepsilon_{ijg}$$

Estimating parameters using ordinary least squares regression standardizes $Y_{ijg}$ to a new term $Z_{ijg}$ (where $\hat{\sigma}_g$ is the standard deviation of $\varepsilon_{ijg}$):

$$Z_{ijg} = \frac{Y_{ijg} - \hat{\alpha}_g - X\hat{\beta}_g}{\hat{\sigma}_g}$$

The standardized data are now distributed according to:

$$Z_{ijg} 18 \, N(\gamma_{ij}, \delta_{ij}^2) \text{ where } \gamma_{ij} \sim N(Y_i, \tau_i^2) \text{ and } \delta_{ij}^2 \sim \text{inverse gamma}(\lambda_i, \theta_i)$$

The inverse gamma is assumed as a standard uninformative prior. The remaining hyperparameters are estimated empirically, with the derivation and solution found in the original reference[32]. The estimated batch effects $\gamma_{ig}^*$ and $\delta_{ij}^{2*}$ can then be used to adjust the standardized data to an empiric-Bayes batch-adjusted final output $Y_{ijg}^*$:

$$Y_{ijg}^* = \frac{\hat{\sigma}_g}{\delta_{ig}^*}(Z_{ijg} - \gamma_{ig}^*) + \hat{\alpha}_g - X\hat{\beta}_g$$

In our modified version of this method (COCONUT), all of the above is performed according to the original method without modification. However, it is applied to only the healthy/control patients in each dataset (i.e. Y is a matrix of only healthy patient samples). The estimated parameters $\hat{\alpha}$, $\hat{\beta}$, $\hat{\sigma}$, $\delta^*$, and $\gamma^*$ are all taken and applied directly to a matrix D that consists only of diseased patient sample (which must be ordered in the same manner as Y):

$$E_{ikg} = \frac{D_{ikg} - \hat{\alpha}_g - X\hat{\beta}_g}{\hat{\sigma}_g}$$

$$D_{ikg}^* = \frac{\hat{\sigma}_g}{\delta_{ig}^*}(E_{ikg} - \gamma_{ig}^*) + \hat{\alpha}_g - X\hat{\beta}_g$$

We can thus obtain a batch-corrected version of diseased samples $D^*$, which corrects for the differences between healthy controls, but does not change each submatrix $D_i$ with respect to each $Y_i$.

Global ROCs

We used COCONUT co-normalization to test (1) all discovery cohorts and (2) all validation cohorts, even those containing only bacterial or only viral illness. We did this separately for the PBMCs and whole blood data, for reasons described above. After co-normalization, the distributions for the individual cohorts were plotted together to allow for direct comparison. For each plot, we show (1) the distribution of scores for each dataset, (2) the normalized gene expression levels for each gene within the diagnostic test, and (3) housekeeping genes which are expected to show no difference between classes based on meta-analysis. The healthy patients have been removed from these plots. However, to show that the distributions of genes between healthy and diseased patients within cohorts do not change after COCONUT co-normalization, we have also shown plots with both patient types with both target genes and housekeeping genes (FIG. 11). Genes with minimal effect size and minimal variance in meta-analysis were selected as housekeeping genes.

For each comparison, a single global ROC AUC was calculated, and a single threshold set to allow for an estimate of the real-world diagnostic performance of the tests. Thresholds for the cutoffs for bacterial versus viral infection were set to approximate a sensitivity for bacterial infection of 90%, since a bacterial infection false negative (i.e., the recommendation not to give antibiotics when antibiotics are needed) can be devastating.

Integrated Antibiotic Decision Model

The SMS can discriminate patients with severe acute infections from those with inflammation from other sources, however, it cannot distinguish between types of infection (FIGS. 5A and 5B). We thus tested an integrated antibiotics decision model (IADM) in which the 11-gene SMS is applied, followed by the 7-gene bacterial/viral metascore. This model thus identifies (1) whether a patient has an infection, and (2) if so, what type of infection is present (bacterial or viral). We were unable to identify enough validation cohorts with patients with non-infected inflammation that also included healthy controls, so in constructing the global ROCs both discovery and validation cohorts were used. Using the COCONUT co-normalization, global thresholds were set across all included cohorts, and these were applied to each individual dataset to test the ability of the IADM to correctly distinguish patients with non-infectious inflammation, bacterial infection, and viral infection. Healthy patients were not included as a diagnostic class as they were used in the co-normalization procedure. The IADM was also applied separately to all cohorts that had no healthy controls, but that included both (1) non-infected SIRS patients and (2) patients with both bacterial and viral infections.

Since positive and negative predictive value (PPV and NPV) are dependent on prevalence, and the prevalence of the data used here does not match the prevalence of infections in a hospital setting, we calculated PPV and NPV curves based on the sensitivity and specificity for bacterial infections attained with the integrated antibiotics decision model. Formally, NPV=specificity×(1-prevalence)/((1-sensitivity)×prevalence+specificity×(1-prevalence)); PPV=sensitivity×prevalence/(sensitivity×prevalence+(1-specificity)×(1-prevalence)).

NanoString Validation

Finally, 96 samples from independent patients (i.e., those never profiled via microarray) from the Genomics of Pediatric SIRS and Septic Shock Investigators trials[18-22] were tested using a targeted NanoString[56] digital multiplex gene quantitation assay. The 18 genes were not re-normalized to any housekeeping genes. The SMS and bacterial/viral metascore genes were both assayed, and the diagnostic performance of the IADM was calculated.

All analyses were conducted in the R statistical computing language (version 3.1.1). Code to recreate the multi-cohort meta-analysis has been previously deposited and is available at khatrilab.stanford.edu/sepsis.

TABLE 1

Datasets used in the discovery and direct validation of the bacterial/viral metascore.

| Accession | Author | Tissue | Platform | Demographic | Bacteria | Virii | Number Bacterial | Number Viral |
|---|---|---|---|---|---|---|---|---|
| A. Discovery datasets ||||||||||
| GSE6269 | Ramilo | PBMC | GPL96 | Children admitted with infection | *E. coli*, *S. aureus*, *S. pneumo* | Influenza | 16 | 8 |
| | | | GPL570 | | *S. aureus*, *S. pneumo* | Influenza | 12 | 10 |
| | | | GPL2507 | | *S. aureus*, *S. pneumo* | Influenza | 73 | 18 |
| GSE20346 | Parnell | Whole Blood | GPL6947 | Adults with CAP | Unknown bacterial pneumonia | Influenza | 12 | 8 |
| GSE40012 | Parnell | Whole Blood | GPL6947 | Adults with CAP | Unknown bacterial pneumonia | Influenza | 36 | 11 |
| GSE40396 | Hu | Whole Blood | GPL10558 | Febrile children in emergency department | Multiple | Adenovirus, enterovirus, rhinovirus, HHV6 | 8 | 35 |
| GSE42026 | Herbeg | Whole Blood | GPL6947 | Children admitted with infection | *Streptococcus* and *Staphylococcus* spp. | Influenza, RSV | 18 | 41 |
| GSE66099 | Wong | Whole Blood | GPL570 | Septic children in PICU | Multiple | Influenza, HSV, CMV, BK, Adeno | 109 | 11 |
| B. Validation datasets ||||||||||
| GSE15297 | Popper | Whole Blood | GPL8328 | Febrile Children | Scarlet fever (*Streptococcus*) | Adenovirus | 5 | 8 |
| GSE25504 | Smith | Whole Blood | GPL13667 | Septic neonates | Multiple | Rhinovirus, CMV | 11 | 3 |
| | | | GPL6947 | | Multiple | CMV | 26 | 1 |
| GSE60244 | Suarez | Whole Blood | GPL10558 | Adults hospitalized with LRPI | Gram positive and atypical | Influenza, RSV, MPV | 22 | 71 |
| GSE63990 | Tsalik | Whole Blood | GPL571 | Adults with ARI | Multiple | Multiple | 70 | 115 |
| E-MEXP-3589 | Almansa | Whole Blood | GPL10332 | Adults w/COPD w/infection | Gram positive, Gram negative, atypical | Influenza, RSV, MPV | 4 | 5 |

CAP: community-acquired pneumonia.
PICU: pediatric intensive care unit.
RSV: respiratory syncytial virus.
CMV: cytomegalovirus.
MPV: metapneumovirus.

TABLE 2

Validation datasets that matched inclusion criteria and have a single known pathogen type (viral or bacterial).

| Accession | Author | Tissue | Platform | Demographic | Specific Pathogens | Number Bacterial | Number Viral |
|---|---|---|---|---|---|---|---|
| E-MEXP-3567 | Irwin | Whole Blood | GPL96 | Malawian children with bacterial meningitis or pneumonia | S. pneumoniae, N. meningitidis, or H. influenzae | 12 | 0 |
| GSE11755 | Emonts | Whole Blood | GPL570 | Children in PICU with meningococcal sepsis | N. meningitidis | 6 | 0 |
| GSE13015 | Pankla | Whole Blood | GPL6106 GPL6947 | Adults with bacterial sepsis | B. pseudomallei and others | 45 15 | 0 0 |
| GSE22098 | Berry | Whole Blood | GPL6947 | Children with Gram positive infections | Staphylococcus and Streptococcus | 52 | 0 |
| GSE28750 | Sutherland | Whole Blood | GPL570 | Adults with community-acquired bacterial sepsis | Multiple bacteria | 10 | 0 |
| GSE29161 | Thuny | Whole Blood | GPL6480 | Adults with native valve infected endocarditis | Staphylococcus and Streptococcus | 5 | 0 |
| GSE33341 | Ahn | Whole Blood | GPl571 | Adults with septic bloodstream infections | S. aureus or E. coli | 51 | 0 |
| GSE40586 | Lill | Whole Blood | GPL6244 | Bacterial meningitis | Multiple bacteria | 21 | 0 |
| GSE42834 | Bloom | Whole blood | GPL10558 | Bacterial Pneumonia | | 19 | 0 |
| GSE57065 | Cazalis | Whole Blood | GPL570 | Adults with bacterial septic shock | Multiple bacteria | 82 | 0 |
| GSE69528 | Conejero | Whole Blood | GPL10558 | Adults with bacterial sepsis | B. pseudomallei and others | 83 | 0 |
| E-MTAB-3162 | van de Weg | Whole Blood | GPL570 | Indonesian patients >14 years old with uncomplicated and severe dengue | Dengue | 0 | 30 |
| GSE17156 | Zaas | Whole blood | GPL571 | Volunteers with viral challenge peak symptoms | Influenza, RSV, rhinovirus | 0 | 27 |
| GSE21802 | Bermejo-Martin | Whole Blood | GPL6102 | Adults with septic influenza | Influenza (H1N1) | 0 | 12 |
| GSE27131 | Berdal | Whole Blood | GPL6244 | Adults with septic influenza with mechanical ventilation | Influenza (H1N1) | 0 | 7 |
| GSE38900 | Mejias | Whole blood | GPL10558 GPL6884 | Children with acute LRTI | RSV Influenza, RSV, rhinovirus | 0 0 | 28 153 |
| GSE51808 | Kwissa | Whole blood | GPL13158 | Children and adults with uncomplicated dengue and DHF | Dengue | 0 | 28 |
| GSE68310 | Zhai | Whole Blood | GPL10558 | Adults with acute respiratory infections | Mostly influenza and rhinovirus | 0 | 211 |
| GSE16129 | Ardura | PBMC | GPL6106 GPL96 | Children with invasive Staph infections | S. aureus | 9 46 | 0 0 |
| GSE23140 | Liu | PBMC | GPL6254 | Children with acute otitis media | S. pneumoniae | 4 | 0 |
| GSE34205 | Ioannidis | PBMC | GPL570 | Infants and children with acute respiratory infections | Influenza, RSV | 0 | 79 |
| GSE38246 | Popper | PBMC | GPL15615 | Nicaraguan children with uncomplicated dengue, DHF, and DSS | Dengue | 0 | 95 |
| GSE69606 | Brand | PBMC | GPL570 | Children with mild-to-severe RSV | RSV | 0 | 26 |

PICU: pediatric intensive care unit.
RSV: respiratory syncytial virus.
LRTI: lower respiratory tract infection.
DHF: Dengue hemorrhagic fever.
DSS: Dengue shock syndrome.

SUPPLEMENTAL TABLE 1

List of all genes found to be significant (q < 0.01, ES > 2 fold overall and ES > 1.5 fold in both PBMCs and whole blood separately) in multi-cohort analysis.

| | summary effect size | summary effect size std. err. | tau^2 | heterogeneity p value | Q | df | overall p value | overall FDR (q value) | mean discovery weighted AUC |
|---|---|---|---|---|---|---|---|---|---|
| OAS1 | 1.184 | 0.146 | 0.105 | 0.003 | 21.322 | 7 | 4.56E−16 | 5.43E−12 | 0.808 |
| IFIT1 | 1.422 | 0.203 | 0.192 | 0.007 | 19.389 | 7 | 2.47E−12 | 4.42E−09 | 0.826 |
| TSPO | −1.233 | 0.177 | 0.141 | 0.009 | 18.858 | 7 | 3.42E−12 | 5.79E−09 | 0.781 |
| SAMD9 | 1.063 | 0.155 | 0.072 | 0.121 | 11.416 | 7 | 7.30E−12 | 9.66E−09 | 0.752 |
| EMR1 | −1.074 | 0.158 | 0.054 | 0.206 | 9.705 | 7 | 9.39E−12 | 1.12E−08 | 0.768 |
| ISG15 | 1.625 | 0.242 | 0.278 | 0.008 | 19.227 | 7 | 1.79E−11 | 1.93E−08 | 0.829 |
| HERC5 | 1.361 | 0.207 | 0.178 | 0.032 | 15.336 | 7 | 4.58E−11 | 3.89E−08 | 0.794 |
| NINJ2 | −1.008 | 0.154 | 0.048 | 0.223 | 9.434 | 7 | 5.75E−11 | 4.67E−08 | 0.741 |
| DDX60 | 1.303 | 0.200 | 0.159 | 0.042 | 14.565 | 7 | 6.91E−11 | 5.25E−08 | 0.797 |
| HESX1 | 1.107 | 0.172 | 0.091 | 0.116 | 11.549 | 7 | 1.28E−10 | 8.69E−08 | 0.749 |
| IFI6 | 1.292 | 0.204 | 0.199 | 0.005 | 20.207 | 7 | 2.28E−10 | 1.33E−07 | 0.794 |
| MX1 | 1.600 | 0.253 | 0.328 | 0.003 | 21.525 | 7 | 2.63E−10 | 1.49E−07 | 0.826 |
| OASL | 1.192 | 0.189 | 0.195 | 0.001 | 25.432 | 7 | 2.73E−10 | 1.52E−07 | 0.788 |
| LAX1 | 1.114 | 0.178 | 0.103 | 0.097 | 12.125 | 7 | 3.59E−10 | 1.86E−07 | 0.769 |
| ACPP | −1.143 | 0.183 | 0.135 | 0.035 | 15.099 | 7 | 4.41E−10 | 2.19E−07 | 0.777 |
| TBXAS1 | −1.213 | 0.195 | 0.159 | 0.031 | 15.409 | 7 | 5.43E−10 | 2.55E−07 | 0.765 |
| IFIT5 | 1.076 | 0.174 | 0.126 | 0.027 | 15.825 | 7 | 6.47E−10 | 3.00E−07 | 0.760 |
| IFIT3 | 1.331 | 0.216 | 0.269 | 0.000 | 32.727 | 7 | 7.55E−10 | 3.42E−07 | 0.794 |
| KCTD14 | 1.163 | 0.190 | 0.161 | 0.011 | 18.106 | 7 | 8.80E−10 | 3.83E−07 | 0.739 |
| OAS2 | 1.379 | 0.230 | 0.346 | 0.000 | 56.480 | 7 | 1.99E−09 | 7.33E−07 | 0.830 |
| PGD | −1.121 | 0.189 | 0.130 | 0.062 | 13.439 | 7 | 2.95E−09 | 1.01E−06 | 0.752 |
| RTP4 | 1.084 | 0.189 | 0.132 | 0.059 | 13.565 | 7 | 9.15E−09 | 2.68E−06 | 0.741 |
| PARP12 | 1.189 | 0.208 | 0.193 | 0.021 | 16.436 | 7 | 1.12E−08 | 3.13E−06 | 0.769 |
| LY6E | 1.479 | 0.260 | 0.363 | 0.001 | 23.586 | 7 | 1.29E−08 | 3.48E−06 | 0.818 |
| S100A12 | −1.067 | 0.190 | 0.135 | 0.056 | 13.727 | 7 | 1.81E−08 | 4.58E−06 | 0.737 |
| ADA | 1.015 | 0.183 | 0.146 | 0.015 | 17.395 | 7 | 2.79E−08 | 6.47E−06 | 0.730 |
| IFI44L | 1.727 | 0.311 | 0.568 | 0.000 | 31.320 | 7 | 2.90E−08 | 6.63E−06 | 0.823 |
| SORT1 | −1.013 | 0.184 | 0.161 | 0.005 | 20.064 | 7 | 4.00E−08 | 8.89E−06 | 0.760 |
| IFI27 | 2.299 | 0.423 | 1.147 | 0.000 | 50.156 | 7 | 5.67E−08 | 1.16E−05 | 0.867 |
| RSAD2 | 1.573 | 0.292 | 0.528 | 0.000 | 35.451 | 7 | 7.48E−08 | 1.47E−05 | 0.825 |
| IFI44 | 1.519 | 0.283 | 0.493 | 0.000 | 37.895 | 7 | 8.24E−08 | 1.57E−05 | 0.816 |
| OAS3 | 1.285 | 0.240 | 0.344 | 0.000 | 33.835 | 7 | 9.09E−08 | 1.69E−05 | 0.808 |
| IFIH1 | 1.014 | 0.192 | 0.183 | 0.003 | 21.908 | 7 | 1.36E−07 | 2.42E−05 | 0.788 |
| TNIP1 | −1.023 | 0.194 | 0.152 | 0.040 | 14.735 | 7 | 1.42E−07 | 2.50E−05 | 0.749 |
| RAB31 | −1.167 | 0.225 | 0.284 | 0.000 | 31.645 | 7 | 2.27E−07 | 3.70E−05 | 0.753 |
| SIGLEC1 | 1.447 | 0.281 | 0.493 | 0.000 | 38.460 | 7 | 2.59E−07 | 4.13E−05 | 0.816 |
| SLC12A9 | −1.215 | 0.237 | 0.306 | 0.000 | 27.836 | 7 | 2.87E−07 | 4.43E−05 | 0.786 |
| JUP | 1.008 | 0.198 | 0.209 | 0.000 | 26.258 | 7 | 3.66E−07 | 5.40E−05 | 0.783 |
| STAT1 | 1.009 | 0.199 | 0.260 | 0.000 | 59.749 | 7 | 3.78E−07 | 5.51E−05 | 0.739 |
| CUL1 | 1.060 | 0.212 | 0.225 | 0.004 | 20.680 | 7 | 5.96E−07 | 7.91E−05 | 0.753 |
| PLP2 | −1.246 | 0.250 | 0.325 | 0.002 | 22.620 | 7 | 5.99E−07 | 7.92E−05 | 0.768 |
| IMPA2 | −1.428 | 0.290 | 0.485 | 0.000 | 29.554 | 7 | 8.28E−07 | 0.00010168 | 0.778 |
| DNMT1 | 1.071 | 0.217 | 0.222 | 0.012 | 18.048 | 7 | 8.34E−07 | 0.00010169 | 0.741 |
| IFIT2 | 1.103 | 0.226 | 0.273 | 0.001 | 23.533 | 7 | 1.01E−06 | 0.00011836 | 0.749 |
| GPAA1 | −1.275 | 0.265 | 0.432 | 0.000 | 43.119 | 7 | 1.50E−06 | 0.0001581 | 0.775 |
| CHST12 | 1.177 | 0.246 | 0.342 | 0.000 | 27.608 | 7 | 1.62E−06 | 0.00016794 | 0.772 |
| LTA4H | −1.585 | 0.332 | 0.666 | 0.000 | 36.759 | 7 | 1.76E−06 | 0.00017814 | 0.766 |
| RTN3 | −1.045 | 0.221 | 0.307 | 0.000 | 46.192 | 7 | 2.39E−06 | 0.00022179 | 0.757 |
| CETP | −1.132 | 0.242 | 0.333 | 0.000 | 29.766 | 7 | 2.86E−06 | 0.00025585 | 0.728 |
| ISG20 | 1.214 | 0.262 | 0.411 | 0.000 | 34.693 | 7 | 3.64E−06 | 0.00030743 | 0.758 |
| TALDO1 | −1.138 | 0.246 | 0.344 | 0.000 | 30.764 | 7 | 3.66E−06 | 0.00030848 | 0.737 |
| DHX58 | 1.197 | 0.259 | 0.370 | 0.001 | 24.871 | 7 | 3.94E−06 | 0.00032598 | 0.732 |
| EIF2AK2 | 1.347 | 0.293 | 0.554 | 0.000 | 47.713 | 7 | 4.28E−06 | 0.00034864 | 0.796 |
| HK3 | −1.109 | 0.242 | 0.304 | 0.002 | 22.157 | 7 | 4.53E−06 | 0.00036318 | 0.748 |
| ACAA1 | −1.077 | 0.235 | 0.309 | 0.000 | 28.834 | 7 | 4.61E−06 | 0.00036811 | 0.745 |
| XAF1 | 1.300 | 0.288 | 0.552 | 0.000 | 55.144 | 7 | 6.56E−06 | 0.0004871 | 0.782 |
| GZMB | 1.203 | 0.267 | 0.394 | 0.000 | 26.203 | 7 | 6.72E−06 | 0.00049528 | 0.770 |
| CAT | −1.034 | 0.230 | 0.322 | 0.000 | 43.416 | 7 | 6.86E−06 | 0.00050173 | 0.710 |
| DOK3 | −1.035 | 0.233 | 0.295 | 0.001 | 25.110 | 7 | 9.08E−06 | 0.00062004 | 0.709 |
| SORL1 | −1.213 | 0.273 | 0.487 | 0.000 | 56.464 | 7 | 9.12E−06 | 0.00062162 | 0.777 |
| PYGL | −1.157 | 0.261 | 0.375 | 0.001 | 25.452 | 7 | 9.46E−06 | 0.00064062 | 0.754 |
| DYSF | −1.127 | 0.256 | 0.359 | 0.001 | 24.813 | 7 | 1.09E−05 | 0.00071449 | 0.748 |
| TWF2 | −1.081 | 0.248 | 0.326 | 0.002 | 23.101 | 7 | 1.27E−05 | 0.00078837 | 0.736 |
| TKT | −1.155 | 0.266 | 0.434 | 0.000 | 40.903 | 7 | 1.40E−05 | 0.000852 | 0.728 |
| CTSB | −1.080 | 0.249 | 0.403 | 0.000 | 64.209 | 7 | 1.48E−05 | 0.00088313 | 0.695 |
| FLII | −1.159 | 0.271 | 0.461 | 0.000 | 46.721 | 7 | 1.95E−05 | 0.00110142 | 0.716 |
| PROS1 | −1.250 | 0.296 | 0.520 | 0.000 | 31.989 | 7 | 2.37E−05 | 0.00127457 | 0.708 |
| NRD1 | −1.103 | 0.261 | 0.400 | 0.000 | 31.123 | 7 | 2.40E−05 | 0.00128279 | 0.730 |
| STAT5B | −1.013 | 0.240 | 0.343 | 0.000 | 44.775 | 7 | 2.46E−05 | 0.0013136 | 0.736 |

SUPPLEMENTAL TABLE 1-continued

List of all genes found to be significant (q < 0.01, ES > 2 fold overall and ES > 1.5 fold in both PBMCs and whole blood separately) in multi-cohort analysis.

| | summary effect size | summary effect size std. err. | tau^2 | heterogeneity p value | Q | df | overall p value | overall FDR (q value) | mean discovery weighted AUC |
|---|---|---|---|---|---|---|---|---|---|
| CYBRD1 | −1.022 | 0.242 | 0.357 | 0.000 | 36.401 | 7 | 2.48E−05 | 0.00131834 | 0.715 |
| PTAFR | −1.083 | 0.257 | 0.403 | 0.000 | 39.437 | 7 | 2.55E−05 | 0.00134828 | 0.727 |
| LAPTM5 | −1.010 | 0.243 | 0.341 | 0.000 | 31.034 | 7 | 3.32E−05 | 0.00165747 | 0.718 |

SUPPLEMENTAL TABLE 2

Datasets with non-infected inflammatory conditions used to test the IADM. Other datasets are listed in Tables 1 & 2.

| Accession | Non-infected condition | Infected condition | Number Non-Infected | Number Infected |
|---|---|---|---|---|
| GSE28750 | Post-surgical adults | Adults with community-acquired bacterial sepsis | 11 | 10 |
| GSE40012 | Non-infected SIRS in adult ICU | Adults with CAP in ICU | 24 | 47 |
| GSE66099 | Non-infected SIRS in pediatric ICU | Pediatric sepsis, severe sepsis and septic shock | 30 | 120 |
| E-MEXP-3589 | Non-infected hospitalized patients with COPD | Hospitalized patients with COPD with respiratory infections | 14 | 9 |
| GSE22098 | Children and adults with SLE and Still's disease | Children with Gram positive infections | 141 | 52 |
| GSE42834 | Adults with sarcoidosis and lung cancer | Adults with bacterial pneumonia | 99 | 19 |

ICU: intensive care unit.
CAP: community-acquired pneumonia.
SLE: systemic lupus erythematosus.

SUPPLEMENTAL TABLE 3

Diagnostic gene sets identified by using a recursive greedy forward search algorithm.

| Order in recursive forward search | positive in viral infection | positive in bacterial infection | GSE6269 gpl2507 AUC | GSE6269 gpl570 AUC |
|---|---|---|---|---|
| 1 | IFI27, JUP, LAX1 | HK3, TNIP1, GPAA1, CTSB | 0.992 | 1 |
| 2 | OAS2, CUL1 | SLC12A9, ACPP, STAT5B | 0.977 | 0.967 |
| 3 | ISG15, CHST12 | EMR1, FLII | 0.945 | 0.933 |
| 4 | IFIT1, SIGLEC1, ADA | PTAFR, NRD1, PLP2 | 1 | 1 |
| 5 | MX1 | DYSF, TWF2 | 1 | 0.925 |
| 6 | RSAD2 | SORT1, TSPO | 0.961 | 0.942 |
| 7 | IFI44L, GZMB, KCTD14 | TBXAS1, ACAA1, S100A12 | 0.938 | 0.958 |
| 8 | LY6E | PGD, LAPTM5 | 0.984 | 0.967 |
| 9 | IFI44, HESX1, OASL | NINJ2, DOK3, SORL1, RAB31 | 0.961 | 0.967 |
| 10 | OAS1 | IMPA2, LTA4H | 0.992 | 0.958 |
| 11 | OAS3, EIF2AK2 | TALDO1 | 0.945 | 0.992 |
| 12 | DDX60, DNMT1 | TKT | 0.984 | 0.908 |
| 13 | HERC5, IFIH1, SAMD9 | PYGL, CETP, PROS1 | 0.961 | 0.925 |
| 14 | IFI6 | RTN3, CAT | 0.938 | 0.983 |
| 15 | IFIT3, IFIT5 | CYBRD1 | 0.938 | 0.925 |
| 16 | XAF1, ISG20, PARP12 | null | 0.867 | 0.925 |
| 17 | IFIT2, DHX58, STAT1 | null | 0.883 | 0.9 |

| Order in recursive forward search | GSE6296 gpl96 AUC | GSE20346 gpl6947 AUC | GSE40012 gpl6947 AUC | GSE40396 gpl10558 AUC | GSE42026 gpl6947 AUC | GSE66099 gpl570 AUC | mean discovery AUC |
|---|---|---|---|---|---|---|---|
| 1 | 0.976 | 1 | 1 | 0.879 | 0.938 | 0.844 | 0.954 |
| 2 | 0.935 | 1 | 0.977 | 0.896 | 0.858 | 0.817 | 0.928 |
| 3 | 0.938 | 1 | 0.949 | 0.9 | 0.858 | 0.796 | 0.915 |
| 4 | 0.944 | 1 | 0.975 | 0.907 | 0.858 | 0.764 | 0.931 |
| 5 | 0.916 | 1 | 0.977 | 0.961 | 0.848 | 0.706 | 0.917 |
| 6 | 0.947 | 1 | 0.952 | 0.879 | 0.9 | 0.736 | 0.915 |

SUPPLEMENTAL TABLE 3-continued

Diagnostic gene sets identified by using a recursive greedy forward search algorithm.

| | | | | | | | |
|---|---|---|---|---|---|---|---|
| 7 | 0.911 | 1 | 0.977 | 0.918 | 0.854 | 0.746 | 0.913 |
| 8 | 0.916 | 1 | 0.977 | 0.864 | 0.885 | 0.697 | 0.911 |
| 9 | 0.94 | 1 | 0.957 | 0.889 | 0.851 | 0.742 | 0.913 |
| 10 | 0.858 | 1 | 0.939 | 0.904 | 0.875 | 0.716 | 0.905 |
| 11 | 0.928 | 0.979 | 0.851 | 0.793 | 0.847 | 0.717 | 0.882 |
| 12 | 0.898 | 0.99 | 0.929 | 0.829 | 0.886 | 0.65 | 0.884 |
| 13 | 0.925 | 0.958 | 0.902 | 0.811 | 0.85 | 0.678 | 0.876 |
| 14 | 0.913 | 1 | 0.889 | 0.854 | 0.79 | 0.651 | 0.877 |
| 15 | 0.901 | 0.958 | 0.866 | 0.729 | 0.858 | 0.645 | 0.852 |
| 16 | 0.944 | 0.948 | 0.841 | 0.764 | 0.837 | 0.598 | 0.84 |
| 17 | 0.848 | 0.938 | 0.879 | 0.736 | 0.833 | 0.578 | 0.824 |

SUPPLEMENTAL TABLE 4

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| SIGLEC1 | SLC12A9 | 0.925 |
| IFI27 | HK3 | 0.921 |
| IFI27 | S100A12 | 0.919 |
| SIGLEC1 | IMPA2 | 0.916 |
| SIGLEC1 | TBXAS1 | 0.916 |
| IFI27 | DYSF | 0.915 |
| IFI27 | TNIP1 | 0.915 |
| SIGLEC1 | ACAA1 | 0.914 |
| SIGLEC1 | DYSF | 0.914 |
| IFI27 | TSPO | 0.913 |
| OAS2 | SLC12A9 | 0.913 |
| IFI27 | EMR1 | 0.912 |
| SIGLEC1 | HK3 | 0.912 |
| IFI27 | SLC12A9 | 0.911 |
| IFI27 | SORT1 | 0.911 |
| OAS3 | HK3 | 0.911 |
| SIGLEC1 | STAT5B | 0.911 |
| IFIT1 | HK3 | 0.91 |
| SIGLEC1 | EMR1 | 0.91 |
| IFI27 | PGD | 0.909 |
| CUL1 | IFI27 | 0.908 |
| IFI27 | JUP | 0.908 |
| IFI27 | ACAA1 | 0.908 |
| IFI27 | GPAA1 | 0.908 |
| IFI27 | NRD1 | 0.908 |
| IFI27 | STAT5B | 0.908 |
| IFIT1 | DYSF | 0.908 |
| OAS1 | HK3 | 0.908 |
| OAS1 | SLC12A9 | 0.908 |
| OAS2 | PTAFR | 0.908 |
| OAS3 | SLC12A9 | 0.908 |
| SIGLEC1 | FLII | 0.908 |
| SIGLEC1 | TSPO | 0.908 |
| CHST12 | IFI27 | 0.907 |
| DNMT1 | IFI27 | 0.907 |
| IFI27 | ACPP | 0.907 |
| IFI27 | CETP | 0.907 |
| IFIT1 | PTAFR | 0.907 |
| ISG15 | PTAFR | 0.907 |
| MX1 | DYSF | 0.907 |
| SIGLEC1 | DOK3 | 0.907 |
| IFI27 | LAX1 | 0.906 |
| IFI27 | DOK3 | 0.906 |
| IFI27 | PTAFR | 0.906 |
| IFI27 | RAB31 | 0.906 |
| IFI27 | SORL1 | 0.906 |
| IFIT1 | SLC12A9 | 0.906 |
| ISG15 | SORT1 | 0.906 |
| MX1 | EMR1 | 0.906 |
| MX1 | HK3 | 0.906 |
| MX1 | SLC12A9 | 0.906 |
| MX1 | SORL1 | 0.906 |
| OAS2 | DYSF | 0.906 |
| OAS2 | TSPO | 0.906 |
| RSAD2 | DYSF | 0.906 |
| IFI27 | NINJ2 | 0.905 |
| IFI27 | PROS1 | 0.905 |
| OAS1 | DYSF | 0.905 |
| OASL | DYSF | 0.905 |
| RSAD2 | SLC12A9 | 0.905 |
| SIGLEC1 | ACPP | 0.905 |
| IFI27 | FLII | 0.904 |
| IFI27 | LAPTM5 | 0.904 |
| IFIT1 | EMR1 | 0.904 |
| IFIT1 | SORL1 | 0.904 |
| MX1 | PTAFR | 0.904 |
| OAS2 | SORL1 | 0.904 |
| OAS3 | DYSF | 0.904 |
| OASL | HK3 | 0.904 |
| RSAD2 | HK3 | 0.904 |
| SIGLEC1 | SORT1 | 0.904 |
| CHST12 | GPAA1 | 0.903 |
| IFI27 | CTSB | 0.903 |
| IFI27 | IMPA2 | 0.903 |
| IFI27 | TBXAS1 | 0.903 |
| IFI27 | TWF2 | 0.903 |
| IFIT1 | SORT1 | 0.903 |
| OAS2 | ACAA1 | 0.903 |
| OAS2 | STAT5B | 0.903 |
| OAS3 | SORT1 | 0.903 |
| EIF2AK2 | HK3 | 0.902 |
| IFI27 | MX1 | 0.902 |
| IFI27 | OAS2 | 0.902 |
| IFI27 | LTA4H | 0.902 |
| IFI27 | PLP2 | 0.902 |
| IFIT1 | RAB31 | 0.902 |
| ISG15 | EMR1 | 0.902 |
| ISG15 | SLC12A9 | 0.902 |
| MX1 | TSPO | 0.902 |
| OAS2 | HK3 | 0.902 |
| OAS2 | PGD | 0.902 |
| RSAD2 | SORT1 | 0.902 |
| SIGLEC1 | PGD | 0.902 |
| SIGLEC1 | PLP2 | 0.902 |
| SIGLEC1 | PTAFR | 0.902 |
| ADA | IFI27 | 0.901 |
| EIF2AK2 | DYSF | 0.901 |
| JUP | PGD | 0.901 |
| LY6E | DYSF | 0.901 |
| LY6E | TNIP1 | 0.901 |
| MX1 | IMPA2 | 0.901 |
| OAS2 | RAB31 | 0.901 |
| IFI27 | ISG20 | 0.9 |
| IFI27 | OAS1 | 0.9 |
| IFI27 | RSAD2 | 0.9 |
| IFI27 | TALDO1 | 0.9 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| IFI44 | SLC12A9 | 0.9 |
| ISG15 | HK3 | 0.9 |
| LY6E | SLC12A9 | 0.9 |
| MX1 | DOK3 | 0.9 |
| MX1 | PGD | 0.9 |
| OAS3 | EMR1 | 0.9 |
| RSAD2 | SORL1 | 0.9 |
| SIGLEC1 | TWF2 | 0.9 |
| GZMB | IFI27 | 0.899 |
| IFI27 | IFI44 | 0.899 |
| IFI27 | CYBRD1 | 0.899 |
| IFI27 | RTN3 | 0.899 |
| ISG15 | DYSF | 0.899 |
| JUP | TSPO | 0.899 |
| LY6E | HK3 | 0.899 |
| LY6E | PGD | 0.899 |
| OAS1 | IMPA2 | 0.899 |
| OAS1 | TSPO | 0.899 |
| OAS2 | IMPA2 | 0.899 |
| RSAD2 | EMR1 | 0.899 |
| EIF2AK2 | SLC12A9 | 0.898 |
| IFIT1 | IFI27 | 0.898 |
| IS615 | IFI27 | 0.898 |
| SIGLEC1 | IFI27 | 0.898 |
| IFI27 | PYGL | 0.898 |
| IFI44 | HK3 | 0.898 |
| IFIT1 | DOK3 | 0.898 |
| IFIT1 | IMPA2 | 0.898 |
| JUP | IMPA2 | 0.898 |
| LY6E | TSPO | 0.898 |
| MX1 | ACPP | 0.898 |
| MX1 | SORT1 | 0.898 |
| MX1 | STAT5B | 0.898 |
| OAS2 | DOK3 | 0.898 |
| OAS2 | GPAA1 | 0.898 |
| OAS3 | SORL1 | 0.898 |
| OASL | PGD | 0.898 |
| OASL | PTAFR | 0.898 |
| SIGLEC1 | SORL1 | 0.898 |
| SIGLEC1 | TALDO1 | 0.898 |
| IFI27 | LY6E | 0.897 |
| IFI27 | OAS3 | 0.897 |
| ISG15 | TSPO | 0.897 |
| LY6E | EMR1 | 0.897 |
| LY6E | TBXAS1 | 0.897 |
| MX1 | RAB31 | 0.897 |
| OAS2 | ACPP | 0.897 |
| OAS2 | NRD1 | 0.897 |
| OAS2 | TNIP1 | 0.897 |
| OAS3 | TBXAS1 | 0.897 |
| OASL | SORT1 | 0.897 |
| OASL | TSPO | 0.897 |
| SIGLEC1 | LAPTM5 | 0.897 |
| EIF2AK2 | IFI27 | 0.896 |
| EIF2AK2 | SORT1 | 0.896 |
| EIF2AK2 | STAT5B | 0.896 |
| EIF2AK2 | TSPO | 0.896 |
| HESX1 | IFI27 | 0.896 |
| IFIT2 | IFI27 | 0.896 |
| KCTD14 | IFI27 | 0.896 |
| PARP12 | IFI27 | 0.896 |
| IFI27 | STAT1 | 0.896 |
| IFI6 | SORT1 | 0.896 |
| IFIT1 | ACPP | 0.896 |
| IFIT1 | TSPO | 0.896 |
| ISG15 | PGD | 0.896 |
| ISG15 | SORL1 | 0.896 |
| LY6E | PTAFR | 0.896 |
| OAS1 | SORT1 | 0.896 |
| OAS1 | TBXAS1 | 0.896 |
| OAS2 | EMR1 | 0.896 |
| OAS2 | LTA4H | 0.896 |
| OAS2 | TBXAS1 | 0.896 |
| OAS3 | TSPO | 0.896 |
| OASL | EMR1 | 0.896 |
| OASL | SLC12A9 | 0.896 |
| SIGLEC1 | GPAA1 | 0.896 |
| IFI27 | HERC5 | 0.895 |
| HESX1 | SLC12A9 | 0.895 |
| IFI6 | HK3 | 0.895 |
| IFIT1 | NINJ2 | 0.895 |
| IFIT1 | TBXAS1 | 0.895 |
| ISG15 | ACPP | 0.895 |
| MX1 | NRD1 | 0.895 |
| MX1 | PLP2 | 0.895 |
| MX1 | TBXAS1 | 0.895 |
| OAS2 | FLII | 0.895 |
| OAS2 | PLP2 | 0.895 |
| OAS3 | IMPA2 | 0.895 |
| OAS3 | PTAFR | 0.895 |
| IFI27 | DDX60 | 0.894 |
| EIF2AK2 | IMPA2 | 0.894 |
| EIF2AK2 | SORL1 | 0.894 |
| IFIH1 | IFI27 | 0.894 |
| IFI27 | TKT | 0.894 |
| IFI44L | PTAFR | 0.894 |
| IFIT1 | ACAA1 | 0.894 |
| LAX1 | ISG15 | 0.894 |
| ISG15 | DOK3 | 0.894 |
| ISG15 | STAT5B | 0.894 |
| OAS1 | RAB31 | 0.894 |
| OAS2 | NINJ2 | 0.894 |
| OAS2 | SORT1 | 0.894 |
| OAS3 | STAT5B | 0.894 |
| SIGLEC1 | CTSB | 0.894 |
| DDX60 | SORT1 | 0.893 |
| EIF2AK2 | PGD | 0.893 |
| EIF2AK2 | PLP2 | 0.893 |
| IFI44L | IFI27 | 0.893 |
| IFI6 | IFI27 | 0.893 |
| OASL | IFI27 | 0.893 |
| IFI27 | CAT | 0.893 |
| IFI44L | EMR1 | 0.893 |
| IFI44L | SLC12A9 | 0.893 |
| 1F16 | EMR1 | 0.893 |
| IFIS | TSPO | 0.893 |
| IFIT1 | STAT5B | 0.893 |
| ISG15 | TNIP1 | 0.893 |
| MX1 | ACAA1 | 0.893 |
| MX1 | FLII | 0.893 |
| OAS1 | EMR1 | 0.893 |
| OAS1 | PGD | 0.893 |
| OAS1 | PLP2 | 0.893 |
| OAS2 | LAPTM5 | 0.893 |
| SIGLEC1 | RTN3 | 0.893 |
| DDX60 | SORL1 | 0.892 |
| IFIT5 | IFI27 | 0.892 |
| IFI44 | ACPP | 0.892 |
| IFI44 | PTAFR | 0.892 |
| IFI44L | ACPP | 0.892 |
| ISG15 | GPAA1 | 0.892 |
| ISG15 | S100A12 | 0.892 |
| ISG15 | TBXAS1 | 0.892 |
| LY6E | IMPA2 | 0.892 |
| LY6E | SORT1 | 0.892 |
| MX1 | TNIP1 | 0.892 |
| OAS1 | PTAFR | 0.892 |
| OAS2 | CTSB | 0.892 |
| RSAD2 | STAT5B | 0.892 |
| SIGLEC1 | LTA4H | 0.892 |
| SIGLEC1 | NRD1 | 0.892 |
| SIGLEC1 | RAB31 | 0.892 |
| SIGLEC1 | TNIP1 | 0.892 |
| IFI44 | SORT1 | 0.891 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| IFI44L | DYSF | 0.891 |
| IFI44L | HK3 | 0.891 |
| IFIT1 | LAPTM5 | 0.891 |
| IFIT1 | PGD | 0.891 |
| IFIT1 | PLP2 | 0.891 |
| ISG15 | RAB31 | 0.891 |
| OASL | IMPA2 | 0.891 |
| DDX60 | SLC12A9 | 0.89 |
| EIF2AK2 | RAB31 | 0.89 |
| SAMD9 | IFI27 | 0.89 |
| IFI44 | SORL1 | 0.89 |
| IFIH1 | SLC12A9 | 0.89 |
| IFIT1 | NRD1 | 0.89 |
| IFIT3 | DYSF | 0.89 |
| ISG15 | TWF2 | 0.89 |
| JUP | ACPP | 0.89 |
| LY6E | FLII | 0.89 |
| MX1 | LTA4H | 0.89 |
| MX1 | S100A12 | 0.89 |
| MX1 | TALDO1 | 0.89 |
| OAS2 | TWF2 | 0.89 |
| OAS3 | ACPP | 0.89 |
| OAS3 | PLP2 | 0.89 |
| PARP12 | SLC12A9 | 0.89 |
| RSAD2 | RAB31 | 0.89 |
| SIGLEC1 | PYGL | 0.89 |
| EIF2AK2 | DOK3 | 0.889 |
| HERC5 | HK3 | 0.889 |
| IFIT3 | IFI27 | 0.889 |
| XAF1 | IFI27 | 0.889 |
| IFIT1 | PYGL | 0.889 |
| IFIT3 | HK3 | 0.889 |
| ISG15 | LAPTM5 | 0.889 |
| ISG15 | NINJ2 | 0.889 |
| ISG15 | PLP2 | 0.889 |
| MX1 | GPAA1 | 0.889 |
| MX1 | NINJ2 | 0.889 |
| OAS1 | CTSB | 0.889 |
| OAS1 | LTA4H | 0.889 |
| OAS1 | TALDO1 | 0.889 |
| OAS2 | TALDO1 | 0.889 |
| OAS3 | PGD | 0.889 |
| RSAD2 | IMPA2 | 0.889 |
| RSAD2 | TBXAS1 | 0.889 |
| SIGLEC1 | TKT | 0.889 |
| CHST12 | SLC12A9 | 0.888 |
| DDX60 | EMR1 | 0.888 |
| DDX60 | HK3 | 0.888 |
| DDX60 | TSPO | 0.888 |
| IFI44 | EMR1 | 0.888 |
| IFI44L | STAT5B | 0.888 |
| LAX1 | IFI6 | 0.888 |
| IFI6 | ACPP | 0.888 |
| LAX1 | IFIT1 | 0.888 |
| IFIT1 | S100A12 | 0.888 |
| IFIT1 | TWF2 | 0.888 |
| ISG15 | ACAA1 | 0.888 |
| ISG15 | IMPA2 | 0.888 |
| ISG15 | LTA4H | 0.888 |
| ISG15 | NRD1 | 0.888 |
| JUP | HK3 | 0.888 |
| KCTD14 | SLC12A9 | 0.888 |
| LY6E | GPAA1 | 0.888 |
| LY6E | LAPTM5 | 0.888 |
| OAS1 | ACPP | 0.888 |
| OAS1 | TWF2 | 0.888 |
| OAS2 | CETP | 0.888 |
| OAS3 | ACAA1 | 0.888 |
| OAS3 | DOK3 | 0.888 |
| OAS3 | RAB31 | 0.888 |
| OASL | TNIP1 | 0.888 |
| RSAD2 | PTAFR | 0.888 |
| RSAD2 | TSPO | 0.888 |
| SIGLEC1 | NINJ2 | 0.888 |
| EIF2AK2 | ADA | 0.887 |
| IFIT1 | ADA | 0.887 |
| IFI27 | DHX58 | 0.887 |
| HERC5 | EMR1 | 0.887 |
| HERC5 | SORT1 | 0.887 |
| IFI44L | SORL1 | 0.887 |
| IFI6 | SLC12A9 | 0.887 |
| IFIT1 | FLII | 0.887 |
| IFIT1 | LTA4H | 0.887 |
| JUP | PLP2 | 0.887 |
| KCTD14 | DOK3 | 0.887 |
| LY6E | ACAA1 | 0.887 |
| MX1 | CTSB | 0.887 |
| MX1 | PYGL | 0.887 |
| OAS1 | ACAA1 | 0.887 |
| OAS1 | SORL1 | 0.887 |
| OASL | TBXAS1 | 0.887 |
| RSAD2 | ACPP | 0.887 |
| MX1 | ADA | 0.886 |
| CUL1 | LTA4H | 0.886 |
| EIF2AK2 | EMR1 | 0.886 |
| HERC5 | ACPP | 0.886 |
| HERC5 | PTAFR | 0.886 |
| HERC5 | SLC12A9 | 0.886 |
| LAX1 | IFI44 | 0.886 |
| JUP | IFI44L | 0.886 |
| IFI44L | IMPA2 | 0.886 |
| IFI6 | DYSF | 0.886 |
| IFIH1 | SORT1 | 0.886 |
| ISG15 | FLII | 0.886 |
| JUP | DYSF | 0.886 |
| JUP | FLII | 0.886 |
| JUP | SLC12A9 | 0.886 |
| LAX1 | GPAA1 | 0.886 |
| LY6E | PLP2 | 0.886 |
| LY6E | TWF2 | 0.886 |
| MX1 | LAPTM5 | 0.886 |
| OAS1 | NRD1 | 0.886 |
| OAS1 | S100A12 | 0.886 |
| OAS3 | FLII | 0.886 |
| OASL | ACPP | 0.886 |
| OASL | DOK3 | 0.886 |
| RSAD2 | LTA4H | 0.886 |
| DHX58 | EMR1 | 0.885 |
| DHX58 | SLC12A9 | 0.885 |
| DHX58 | SORT1 | 0.885 |
| IFI44 | TBXAS1 | 0.885 |
| IFI44 | TSPO | 0.885 |
| IFIH1 | PTAFR | 0.885 |
| IFIT3 | SLC12A9 | 0.885 |
| MX1 | LAX1 | 0.885 |
| LY6E | CTSB | 0.885 |
| LY6E | DOK3 | 0.885 |
| LY6E | S100A12 | 0.885 |
| LY6E | STAT5B | 0.885 |
| MX1 | TKT | 0.885 |
| MX1 | TWF2 | 0.885 |
| OAS1 | FLII | 0.885 |
| OAS2 | PYGL | 0.885 |
| OAS2 | S100A12 | 0.885 |
| OASL | RAB31 | 0.885 |
| PARP12 | SORT1 | 0.885 |
| RSAD2 | NINJ2 | 0.885 |
| RSAD2 | S100A12 | 0.885 |
| GPAA1 | SORL1 | 0.885 |
| IFI44 | ADA | 0.884 |
| CUL1 | SLC12A9 | 0.884 |
| DDX60 | ACPP | 0.884 |
| EIF2AK2 | ACAA1 | 0.884 |
| EIF2AK2 | LAPTM5 | 0.884 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| EIF2AK2 | S100A12 | 0.884 |
| IFI44 | GZMB | 0.884 |
| IFI44L | ACAA1 | 0.884 |
| IFI44L | TBXAS1 | 0.884 |
| IFI6 | PLP2 | 0.884 |
| IFI6 | PTAFR | 0.884 |
| IFI6 | RAB31 | 0.884 |
| IFI6 | S100A12 | 0.884 |
| IFIT1 | CTSB | 0.884 |
| IFIT3 | PTAFR | 0.884 |
| ISG15 | CTSB | 0.884 |
| ISG15 | PYGL | 0.884 |
| JUP | RAB31 | 0.884 |
| JUP | TBXAS1 | 0.884 |
| OAS2 | LAX1 | 0.884 |
| LY6E | SORL1 | 0.884 |
| OAS1 | NINJ2 | 0.884 |
| OAS1 | TKT | 0.884 |
| OAS2 | RTN3 | 0.884 |
| OASL | S100A12 | 0.884 |
| RSAD2 | DOK3 | 0.884 |
| RSAD2 | LAPTM5 | 0.884 |
| RSAD2 | PLP2 | 0.884 |
| RSAD2 | TWF2 | 0.884 |
| SIGLEC1 | CETP | 0.884 |
| GPAA1 | LTA4H | 0.884 |
| ISG15 | DNMT1 | 0.883 |
| ISG15 | EIF2AK2 | 0.883 |
| EIF2AK2 | PTAFR | 0.883 |
| IFI44L | NRD1 | 0.883 |
| IFI44L | PLP2 | 0.883 |
| IFI44L | SORT1 | 0.883 |
| IFI44L | TSPO | 0.883 |
| IFI6 | TBXAS1 | 0.883 |
| IFIT1 | TNIP1 | 0.883 |
| JUP | PTAFR | 0.883 |
| JUP | TALDO1 | 0.883 |
| JUP | TNIP1 | 0.883 |
| RSAD2 | LAX1 | 0.883 |
| LY6E | ACPP | 0.883 |
| LY6E | RAB31 | 0.883 |
| MX1 | RTN3 | 0.883 |
| OAS1 | PYGL | 0.883 |
| OAS2 | TKT | 0.883 |
| OAS3 | CTSB | 0.883 |
| OASL | PLP2 | 0.883 |
| RSAD2 | NRD1 | 0.883 |
| LAX1 | EIF2AK2 | 0.882 |
| IFI44L | GZMB | 0.882 |
| ISG15 | GZMB | 0.882 |
| HESX1 | ACAA1 | 0.882 |
| JUP | IFI44 | 0.882 |
| IFI44 | ACAA1 | 0.882 |
| LAX1 | IFI44L | 0.882 |
| IFI44L | CTSB | 0.882 |
| IFI44L | NINJ2 | 0.882 |
| IFI6 | ACAA1 | 0.882 |
| IFI6 | IMPA2 | 0.882 |
| IFIH1 | HK3 | 0.882 |
| IFIT1 | TALDO1 | 0.882 |
| IFIT1 | TKT | 0.882 |
| JUP | ISG15 | 0.882 |
| SIGLEC1 | ISG15 | 0.882 |
| ISG15 | TKT | 0.882 |
| JUP | GPAA1 | 0.882 |
| JUP | LTA4H | 0.882 |
| LY6E | NINJ2 | 0.882 |
| LY6E | TALDO1 | 0.882 |
| MX1 | CETP | 0.882 |
| OAS1 | DOK3 | 0.882 |
| OAS1 | STAT5B | 0.882 |
| OAS1 | TNIP1 | 0.882 |
| OAS3 | LAPTM5 | 0.882 |
| OAS3 | TALDO1 | 0.882 |
| OAS3 | TNIP1 | 0.882 |
| OASL | NINJ2 | 0.882 |
| RSAD2 | ACAA1 | 0.882 |
| RSAD2 | CTSB | 0.882 |
| RSAD2 | TNIP1 | 0.882 |
| SAMD9 | HK3 | 0.882 |
| SAMD9 | SLC12A9 | 0.882 |
| LTA4H | SLC12A9 | 0.882 |
| MX1 | DNMT1 | 0.881 |
| EIF2AK2 | ACPP | 0.881 |
| EIF2AK2 | TNIP1 | 0.881 |
| HERC5 | DYSF | 0.881 |
| IFI44L | RAB31 | 0.881 |
| IFI44L | S100A12 | 0.881 |
| IFI6 | NINJ2 | 0.881 |
| IFI6 | PGD | 0.881 |
| IFI6 | TWF2 | 0.881 |
| IFIT1 | RTN3 | 0.881 |
| IFIT3 | EMR1 | 0.881 |
| IFIT3 | SORL1 | 0.881 |
| JUP | RTN3 | 0.881 |
| JUP | TWF2 | 0.881 |
| KCTD14 | SORT1 | 0.881 |
| LAX1 | SORL1 | 0.881 |
| OAS3 | LTA4H | 0.881 |
| OAS3 | PYGL | 0.881 |
| OASL | ACAA1 | 0.881 |
| PARP12 | EMR1 | 0.881 |
| XAF1 | SLC12A9 | 0.881 |
| STAT5B | LTA4H | 0.881 |
| ADA | IFI44L | 0.88 |
| ADA | ISG15 | 0.88 |
| ADA | RSAD2 | 0.88 |
| DDX60 | RAB31 | 0.88 |
| DDX60 | STAT5B | 0.88 |
| DNMT1 | IFI6 | 0.88 |
| EIF2AK2 | TBXAS1 | 0.88 |
| HERC5 | SORL1 | 0.88 |
| HERC5 | TBXAS1 | 0.88 |
| HESX1 | LTA4H | 0.88 |
| HESX1 | SORL1 | 0.88 |
| IFI44 | IMPA2 | 0.88 |
| IFI44 | RAB31 | 0.88 |
| IFI44L | DOK3 | 0.88 |
| IFIH1 | TSPO | 0.88 |
| IFIT5 | RAB31 | 0.88 |
| IFIT5 | SORL1 | 0.88 |
| JUP | MX1 | 0.88 |
| JUP | NINJ2 | 0.88 |
| JUP | STAT5B | 0.88 |
| KCTD14 | ACPP | 0.88 |
| KCTD14 | GPAA1 | 0.88 |
| KCTD14 | LTA4H | 0.88 |
| KCTD14 | PLP2 | 0.88 |
| KCTD14 | TNIP1 | 0.88 |
| LAX1 | OAS3 | 0.88 |
| LAX1 | SIGLEC1 | 0.88 |
| LY6E | LTA4H | 0.88 |
| OAS3 | NINJ2 | 0.88 |
| OAS3 | TWF2 | 0.88 |
| OASL | RTN3 | 0.88 |
| PARP12 | STAT5B | 0.88 |
| RSAD2 | PGD | 0.88 |
| RSAD2 | PYGL | 0.88 |
| GPAA1 | RAB31 | 0.88 |
| GPAA1 | SLC12A9 | 0.88 |
| LTA4H | TNIP1 | 0.88 |
| ADA | HERC5 | 0.879 |
| ADA | OAS3 | 0.879 |
| CHST12 | ISG15 | 0.879 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| CHST12 | STAT5B | 0.879 |
| GZMB | OAS3 | 0.879 |
| HERC5 | TSPO | 0.879 |
| IFI44 | LY6E | 0.879 |
| IFI44 | DYSF | 0.879 |
| IFI44 | LTA4H | 0.879 |
| IFI44L | PGD | 0.879 |
| IFI44L | TWF2 | 0.879 |
| IFIH1 | DYSF | 0.879 |
| IFIT1 | JUP | 0.879 |
| IFIT1 | PROS1 | 0.879 |
| IFIT3 | SORT1 | 0.879 |
| ISG15 | CETP | 0.879 |
| ISG15 | RTN3 | 0.879 |
| OAS3 | GPAA1 | 0.879 |
| OASL | PYGL | 0.879 |
| PARP12 | SORL1 | 0.879 |
| GPAA1 | RTN3 | 0.879 |
| ADA | IFI6 | 0.878 |
| CHST12 | DDX60 | 0.878 |
| CHST12 | MX1 | 0.878 |
| DDX60 | LAX1 | 0.878 |
| DHX58 | PTAFR | 0.878 |
| DNMT1 | IFIT1 | 0.878 |
| GZMB | IFIT1 | 0.878 |
| GZMB | MX1 | 0.878 |
| GZMB | RSAD2 | 0.878 |
| HERC5 | RAB31 | 0.878 |
| IFI44 | NINJ2 | 0.878 |
| IFI44 | STAT5B | 0.878 |
| IFI44L | FLII | 0.878 |
| IFI44L | LTA4H | 0.878 |
| IFI44L | TNIP1 | 0.878 |
| IFI6 | DOK3 | 0.878 |
| IFI6 | LAPTM5 | 0.878 |
| IFIH1 | EMR1 | 0.878 |
| IFIT3 | ACPP | 0.878 |
| ISG15 | CAT | 0.878 |
| ISG15 | TALDO1 | 0.878 |
| JUP | CTSB | 0.878 |
| KCTD14 | RSAD2 | 0.878 |
| LAX1 | OASL | 0.878 |
| LY6E | RTN3 | 0.878 |
| LY6E | TKT | 0.878 |
| MX1 | SIGLEC1 | 0.878 |
| OAS3 | S100A12 | 0.878 |
| OASL | TWF2 | 0.878 |
| RSAD2 | FLII | 0.878 |
| RSAD2 | GPAA1 | 0.878 |
| RSAD2 | TALDO1 | 0.878 |
| XAF1 | DYSF | 0.878 |
| XAF1 | SORT1 | 0.878 |
| DDX60 | IMPA2 | 0.877 |
| DDX60 | PTAFR | 0.877 |
| DDX60 | TBXAS1 | 0.877 |
| IFI44 | DNMT1 | 0.877 |
| IFI44L | DNMT1 | 0.877 |
| LAX1 | HERC5 | 0.877 |
| HESX1 | SORT1 | 0.877 |
| IFI44L | LAPTM5 | 0.877 |
| IFIT1 | CAT | 0.877 |
| IFIT3 | TBXAS1 | 0.877 |
| JUP | EMR1 | 0.877 |
| KCTD14 | PGD | 0.877 |
| OAS1 | LAPTM5 | 0.877 |
| OAS1 | RTN3 | 0.877 |
| OASL | TALDO1 | 0.877 |
| XAF1 | EMR1 | 0.877 |
| XAF1 | PTAFR | 0.877 |
| LTA4H | EMR1 | 0.877 |
| CHST12 | IFI44 | 0.876 |
| CUL1 | ACAA1 | 0.876 |
| DHX58 | SORL1 | 0.876 |
| EIF2AK2 | CTSB | 0.876 |
| EIF2AK2 | RTN3 | 0.876 |
| HESX1 | ISG15 | 0.876 |
| HESX1 | EMR1 | 0.876 |
| HESX1 | PLP2 | 0.876 |
| IFI44 | KCTD14 | 0.876 |
| IFI44 | DOK3 | 0.876 |
| IFI44 | TNIP1 | 0.876 |
| IFI44L | KCTD14 | 0.876 |
| IFI44L | LY6E | 0.876 |
| IFI6 | LTA4H | 0.876 |
| IFI6 | STAT5B | 0.876 |
| IFIT1 | KCTD14 | 0.876 |
| IFIT1 | GPAA1 | 0.876 |
| JUP | LAPTM5 | 0.876 |
| JUP | TKT | 0.876 |
| KCTD14 | ACAA1 | 0.876 |
| LY6E | LAX1 | 0.876 |
| SAMD9 | LAX1 | 0.876 |
| LY6E | CETP | 0.876 |
| OASL | CTSB | 0.876 |
| OASL | SORL1 | 0.876 |
| XAF1 | HK3 | 0.876 |
| XAF1 | SORL1 | 0.876 |
| IFIT1 | CHST12 | 0.875 |
| IFI44L | CUL1 | 0.875 |
| DDX60 | ACAA1 | 0.875 |
| EIF2AK2 | LTA4H | 0.875 |
| HERC5 | S100A12 | 0.875 |
| HESX1 | TBXAS1 | 0.875 |
| HESX1 | TSPO | 0.875 |
| IFI44 | CTSB | 0.875 |
| IFI44 | GPAA1 | 0.875 |
| ISG15 | IFI44L | 0.875 |
| SIGLEC1 | IFI44L | 0.875 |
| IFI6 | SORL1 | 0.875 |
| MX1 | ISG15 | 0.875 |
| ISG20 | SLC12A9 | 0.875 |
| KCTD14 | TSPO | 0.875 |
| LY6E | PYGL | 0.875 |
| OAS2 | CAT | 0.875 |
| OASL | STAT5B | 0.875 |
| PARP12 | PTAFR | 0.875 |
| RSAD2 | PROS1 | 0.875 |
| RSAD2 | RTN3 | 0.875 |
| ACPP | GPAA1 | 0.875 |
| CHST12 | IFI44L | 0.874 |
| CHST12 | TWF2 | 0.874 |
| CUL1 | TSPO | 0.874 |
| JUP | DDX60 | 0.874 |
| DDX60 | DYSF | 0.874 |
| DDX60 | LTA4H | 0.874 |
| DHX58 | TSPO | 0.874 |
| EIF2AK2 | NRD1 | 0.874 |
| HERC5 | IMPA2 | 0.874 |
| HERC5 | STAT5B | 0.874 |
| HESX1 | ACPP | 0.874 |
| IFI44 | PLP2 | 0.874 |
| IFI44 | S100A12 | 0.874 |
| IFI44 | TWF2 | 0.874 |
| IFI44L | RTN3 | 0.874 |
| IFI44L | TALDO1 | 0.874 |
| IFI44L | TKT | 0.874 |
| IFI6 | ISG15 | 0.874 |
| IFI6 | SIGLEC1 | 0.874 |
| IFI6 | CTSB | 0.874 |
| IFIH1 | ACAA1 | 0.874 |
| IFIH1 | SORL1 | 0.874 |
| IFIT1 | CETP | 0.874 |
| IFIT3 | IMPA2 | 0.874 |
| IFIT3 | NINJ2 | 0.874 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| IFIT5 | SORT1 | 0.874 |
| LY6E | ISG15 | 0.874 |
| ISG15 | CYBRD1 | 0.874 |
| KCTD14 | RTN3 | 0.874 |
| OAS1 | LAX1 | 0.874 |
| LY6E | NRD1 | 0.874 |
| MX1 | CAT | 0.874 |
| OAS3 | NRD1 | 0.874 |
| OAS3 | TKT | 0.874 |
| OASL | FLII | 0.874 |
| RSAD2 | CETP | 0.874 |
| GPAA1 | S100A12 | 0.874 |
| LTA4H | SORL1 | 0.874 |
| ADA | OASL | 0.873 |
| ADA | SIGLEC1 | 0.873 |
| CHST12 | IMPA2 | 0.873 |
| DDX60 | DOK3 | 0.873 |
| DNMT1 | GPAA1 | 0.873 |
| HERC5 | GZMB | 0.873 |
| HERC5 | PLP2 | 0.873 |
| ISG15 | IFI44 | 0.873 |
| IFI44 | CAT | 0.873 |
| IFI44 | NRD1 | 0.873 |
| OAS2 | IFI44L | 0.873 |
| IFI44L | CETP | 0.873 |
| IFI44L | GPAA1 | 0.873 |
| IFIH1 | ACPP | 0.873 |
| IFIT1 | CYBRD1 | 0.873 |
| IFIT2 | HK3 | 0.873 |
| IFIT5 | ACPP | 0.873 |
| IFIT5 | SLC12A9 | 0.873 |
| LAX1 | KCTD14 | 0.873 |
| MX1 | KCTD14 | 0.873 |
| XAF1 | STAT5B | 0.873 |
| LTA4H | TSPO | 0.873 |
| DDX60 | ADA | 0.872 |
| OAS2 | ADA | 0.872 |
| ADA | GPAA1 | 0.872 |
| RSAD2 | CHST12 | 0.872 |
| CHST12 | ACAA1 | 0.872 |
| CHST12 | FLII | 0.872 |
| CHST12 | LAPTM5 | 0.872 |
| CHST12 | PLP2 | 0.872 |
| CHST12 | PTAFR | 0.872 |
| CHST12 | TBXAS1 | 0.872 |
| CUL1 | GPAA1 | 0.872 |
| CUL1 | SORL1 | 0.872 |
| DDX60 | PYGL | 0.872 |
| DHX58 | DOK3 | 0.872 |
| DNMT1 | LTA4H | 0.872 |
| SIGLEC1 | EIF2AK2 | 0.872 |
| EIF2AK2 | PYGL | 0.872 |
| JUP | HERC5 | 0.872 |
| HERC5 | LTA4H | 0.872 |
| HESX1 | IMPA2 | 0.872 |
| SIGLEC1 | IFI44 | 0.872 |
| IFI44 | TALDO1 | 0.872 |
| IFI44L | CYBRD1 | 0.872 |
| IFI44L | PROS1 | 0.872 |
| IFI44L | PYGL | 0.872 |
| IFI6 | GPAA1 | 0.872 |
| IFI6 | RTN3 | 0.872 |
| IFI6 | TNIP1 | 0.872 |
| RSAD2 | JUP | 0.872 |
| OAS3 | KCTD14 | 0.872 |
| KCTD14 | RAB31 | 0.872 |
| LY6E | CAT | 0.872 |
| LY6E | PROS1 | 0.872 |
| MX1 | PROS1 | 0.872 |
| OAS1 | CAT | 0.872 |
| SIGLEC1 | OAS2 | 0.872 |
| OAS2 | PROS1 | 0.872 |
| OAS3 | RTN3 | 0.872 |
| PARP12 | HK3 | 0.872 |
| RSAD2 | CYBRD1 | 0.872 |
| RSAD2 | TKT | 0.872 |
| SAMD9 | SORT1 | 0.872 |
| SIGLEC1 | S100A12 | 0.872 |
| LY6E | ADA | 0.871 |
| OAS3 | CHST12 | 0.871 |
| DHX58 | HK3 | 0.871 |
| EIF2AK2 | LY6E | 0.871 |
| EIF2AK2 | CETP | 0.871 |
| EIF2AK2 | TALDO1 | 0.871 |
| EIF2AK2 | TKT | 0.871 |
| HERC5 | NINJ2 | 0.871 |
| IFI6 | HESX1 | 0.871 |
| HESX1 | RAB31 | 0.871 |
| IFI44L | CAT | 0.871 |
| IFI6 | FLII | 0.871 |
| ISG15 | IFIT1 | 0.871 |
| SIGLEC1 | IFIT1 | 0.871 |
| IFIT2 | PTAFR | 0.871 |
| IFIT5 | HK3 | 0.871 |
| IFIT5 | TSPO | 0.871 |
| ISG15 | PROS1 | 0.871 |
| ISG20 | PLP2 | 0.871 |
| OAS3 | JUP | 0.871 |
| JUP | ACAA1 | 0.871 |
| JUP | CETP | 0.871 |
| LAX1 | STAT5B | 0.871 |
| OAS1 | CETP | 0.871 |
| OASL | LAPTM5 | 0.871 |
| PARP12 | CTSB | 0.871 |
| PARP12 | TSPO | 0.871 |
| SAMD9 | EMR1 | 0.871 |
| ACPP | STAT5B | 0.871 |
| LTA4H | PLP2 | 0.871 |
| CHST12 | IFI6 | 0.87 |
| SIGLEC1 | CUL1 | 0.87 |
| DDX60 | NINJ2 | 0.87 |
| DDX60 | NRD1 | 0.87 |
| DHX58 | IMPA2 | 0.87 |
| DHX58 | STAT5B | 0.87 |
| RSAD2 | DNMT1 | 0.87 |
| OAS2 | GZMB | 0.87 |
| HERC5 | ACAA1 | 0.87 |
| HERC5 | DOK3 | 0.87 |
| IFI44 | HESX1 | 0.87 |
| HESX1 | DOK3 | 0.87 |
| HESX1 | FLII | 0.87 |
| OAS2 | IFI44 | 0.87 |
| IFI44 | PGD | 0.87 |
| IFI44 | PYGL | 0.87 |
| ISG20 | IFI44L | 0.87 |
| IFI6 | NRD1 | 0.87 |
| IFIH1 | RAB31 | 0.87 |
| MX1 | IFIT1 | 0.87 |
| LAX1 | IFIT3 | 0.87 |
| KCTD14 | ISG15 | 0.87 |
| RSAD2 | ISG15 | 0.87 |
| ISG20 | GPAA1 | 0.87 |
| JUP | DOK3 | 0.87 |
| KCTD14 | CETP | 0.87 |
| RSAD2 | LY6E | 0.87 |
| OAS2 | MX1 | 0.87 |
| OAS1 | GPAA1 | 0.87 |
| OAS1 | PROS1 | 0.87 |
| OASL | TKT | 0.87 |
| RSAD2 | CAT | 0.87 |
| GPAA1 | IMPA2 | 0.87 |
| GPAA1 | STAT5B | 0.87 |
| LTA4H | SORT1 | 0.87 |
| CHST12 | ACPP | 0.869 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
| --- | --- | --- |
| ISG15 | CUL1 | 0.869 |
| CUL1 | IMPA2 | 0.869 |
| LY6E | DDX60 | 0.869 |
| DDX60 | PGD | 0.869 |
| DHX58 | DYSF | 0.869 |
| GZMB | EIF2AK2 | 0.869 |
| EIF2AK2 | GPAA1 | 0.869 |
| OASL | GZMB | 0.869 |
| HERC5 | TWF2 | 0.869 |
| IFI44L | HESX1 | 0.869 |
| HESX1 | PGD | 0.869 |
| IFI44 | LAPTM5 | 0.869 |
| IFI44 | PROS1 | 0.869 |
| OAS2 | IFI6 | 0.869 |
| IFI6 | TALDO1 | 0.869 |
| IFIH1 | DOK3 | 0.869 |
| IFIT5 | STAT5B | 0.869 |
| OAS2 | ISG15 | 0.869 |
| ISG20 | TNIP1 | 0.869 |
| SIGLEC1 | KCTD14 | 0.869 |
| LY6E | OAS2 | 0.869 |
| OAS3 | CETP | 0.869 |
| OASL | CETP | 0.869 |
| SAMD9 | TSPO | 0.869 |
| FLII | LTA4H | 0.869 |
| SIGLEC1 | CHST12 | 0.868 |
| CHST12 | EMR1 | 0.868 |
| CIFIT1 | UL1 | 0.868 |
| DNMT1 | DDX60 | 0.868 |
| ISG15 | DDX60 | 0.868 |
| EIF2AK2 | DNMT1 | 0.868 |
| DNMT1 | HERC5 | 0.868 |
| IFI44L | EIF2AK2 | 0.868 |
| EIF2AK2 | FLII | 0.868 |
| EIF2AK2 | TWF2 | 0.868 |
| LY6E | GZMB | 0.868 |
| HERC5 | LAPTM5 | 0.868 |
| HERC5 | PYGL | 0.868 |
| HESX1 | DYSF | 0.868 |
| IFIT1 | IFI44L | 0.868 |
| MX1 | IFI44L | 0.868 |
| JUP | IFI6 | 0.868 |
| IFIH1 | LTA4H | 0.868 |
| IFIT2 | DYSF | 0.868 |
| IFIT2 | SLC12A9 | 0.868 |
| IFIT3 | S100A12 | 0.868 |
| IFIT3 | STAT5B | 0.868 |
| IFIT3 | TSPO | 0.868 |
| IFIT5 | EMR1 | 0.868 |
| IFIT5 | IMPA2 | 0.868 |
| OAS3 | ISG15 | 0.868 |
| JUP | NRD1 | 0.868 |
| JUP | PYGL | 0.868 |
| KCTD14 | TBXAS1 | 0.868 |
| MX1 | LY6E | 0.868 |
| SIGLEC1 | LY6E | 0.868 |
| OASL | LTA4H | 0.868 |
| PARP12 | IMPA2 | 0.868 |
| PARP12 | RAB31 | 0.868 |
| SIGLEC1 | RSAD2 | 0.868 |
| SAMD9 | RAB31 | 0.868 |
| SAMD9 | S100A12 | 0.868 |
| ACAA1 | LTA4H | 0.868 |
| PLP2 | SORL1 | 0.868 |
| RAB31 | SLC12A9 | 0.868 |
| CHST12 | TSPO | 0.867 |
| IFI44 | CUL1 | 0.867 |
| DDX60 | PLP2 | 0.867 |
| SIGLEC1 | HERC5 | 0.867 |
| HERC5 | CTSB | 0.867 |
| HESX1 | GPAA1 | 0.867 |
| HESX1 | RTN3 | 0.867 |
| HESX1 | STAT5B | 0.867 |
| IFI44 | FLII | 0.867 |
| IFI44 | TKT | 0.867 |
| RSAD2 | IFI44L | 0.867 |
| IFI6 | CETP | 0.867 |
| IFI6 | TKT | 0.867 |
| IFIH1 | S100A12 | 0.867 |
| IFIH1 | TBXAS1 | 0.867 |
| ISG20 | IFIT1 | 0.867 |
| IFIT3 | PLP2 | 0.867 |
| IFIT3 | RAB31 | 0.867 |
| ISG20 | IMPA2 | 0.867 |
| ISG20 | TSPO | 0.867 |
| JUP | S100A12 | 0.867 |
| KCTD14 | IMPA2 | 0.867 |
| KCTD14 | TALDO1 | 0.867 |
| PARP12 | PLP2 | 0.867 |
| XAF1 | ACPP | 0.867 |
| GPAA1 | TALDO1 | 0.867 |
| OAS1 | ADA | 0.866 |
| EIF2AK2 | IFI44 | 0.866 |
| OAS1 | GZMB | 0.866 |
| SIGLEC1 | GZMB | 0.866 |
| HERC5 | PGD | 0.866 |
| LAX1 | HESX1 | 0.866 |
| MX1 | HESX1 | 0.866 |
| HESX1 | CTSB | 0.866 |
| HESX1 | HK3 | 0.866 |
| HESX1 | PTAFR | 0.866 |
| IFI44 | ISG20 | 0.866 |
| IFI44 | CYBRD1 | 0.866 |
| IFI6 | IFI44L | 0.866 |
| KCTD14 | IFI6 | 0.866 |
| MX1 | IFI6 | 0.866 |
| IFI6 | RSAD2 | 0.866 |
| IFIH1 | IMPA2 | 0.866 |
| IFIH1 | STAT5B | 0.866 |
| LY6E | IFIT1 | 0.866 |
| IFIT3 | DOK3 | 0.866 |
| IFIT3 | TALDO1 | 0.866 |
| ISG20 | ISG15 | 0.866 |
| SIGLEC1 | JUP | 0.866 |
| KCTD14 | NRD1 | 0.866 |
| PARP12 | LAX1 | 0.866 |
| LAX1 | SLC12A9 | 0.866 |
| MX1 | CYBRD1 | 0.866 |
| SAMD9 | ACPP | 0.866 |
| SAMD9 | PTAFR | 0.866 |
| GPAA1 | TSPO | 0.866 |
| SORL1 | S100A12 | 0.866 |
| CHST12 | LTA4H | 0.865 |
| CHST12 | PGD | 0.865 |
| CHST12 | SORL1 | 0.865 |
| CUL1 | MX1 | 0.865 |
| DDX60 | GZMB | 0.865 |
| DHX58 | ACAA1 | 0.865 |
| EIF2AK2 | IFIT1 | 0.865 |
| EIF2AK2 | OAS2 | 0.865 |
| GZMB | LTA4H | 0.865 |
| GZMB | PGD | 0.865 |
| GZMB | TSPO | 0.865 |
| HERC5 | PROS1 | 0.865 |
| HERC5 | TALDO1 | 0.865 |
| IFI44 | CETP | 0.865 |
| IFI44 | RTN3 | 0.865 |
| IFI44L | OASL | 0.865 |
| IFI6 | PYGL | 0.865 |
| IFIH1 | NRD1 | 0.865 |
| IFIH1 | PLP2 | 0.865 |
| IFIH1 | PYGL | 0.865 |
| OAS2 | IFIT1 | 0.865 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| IFIT2 | ACPP | 0.865 |
| IFIT3 | PGD | 0.865 |
| ISG20 | LTA4H | 0.865 |
| KCTD14 | PTAFR | 0.865 |
| OAS2 | CYBRD1 | 0.865 |
| SIGLEC1 | OAS3 | 0.865 |
| OASL | GPAA1 | 0.865 |
| PARP12 | LTA4H | 0.865 |
| SAMD9 | IMPA2 | 0.865 |
| SAMD9 | SORL1 | 0.865 |
| XAF1 | TSPO | 0.865 |
| CETP | SLC12A9 | 0.865 |
| GPAA1 | NRD1 | 0.865 |
| GPAA1 | TBXAS1 | 0.865 |
| LAPTM5 | LTA4H | 0.865 |
| CHST12 | HERC5 | 0.864 |
| CHST12 | OAS1 | 0.864 |
| OAS2 | CHST12 | 0.864 |
| CHST12 | SORT1 | 0.864 |
| OAS2 | DDX60 | 0.864 |
| DDX60 | S100A12 | 0.864 |
| DHX58 | PLP2 | 0.864 |
| OAS2 | DNMT1 | 0.864 |
| DNMT1 | FLII | 0.864 |
| EIF2AK2 | MX1 | 0.864 |
| EIF2AK2 | NINJ2 | 0.864 |
| GZMB | IFI6 | 0.864 |
| HERC5 | CAT | 0.864 |
| HERC5 | FLII | 0.864 |
| HERC5 | NRD1 | 0.864 |
| HERC5 | RTN3 | 0.864 |
| HERC5 | TNIP1 | 0.864 |
| IFI44 | IFI44L | 0.864 |
| IFI44 | MX1 | 0.864 |
| IFI44 | RSAD2 | 0.864 |
| IFI6 | PROS1 | 0.864 |
| IFIH1 | ISG15 | 0.864 |
| IFIT2 | EMR1 | 0.864 |
| IFIT2 | SORL1 | 0.864 |
| IFIT3 | ACAA1 | 0.864 |
| IFIT3 | LTA4H | 0.864 |
| IFIT5 | PLP2 | 0.864 |
| ISG15 | OAS1 | 0.864 |
| ISG20 | RAB31 | 0.864 |
| ISG20 | STAT5B | 0.864 |
| KCTD14 | TKT | 0.864 |
| LAX1 | LTA4H | 0.864 |
| PARP12 | DYSF | 0.864 |
| PARP12 | NINJ2 | 0.864 |
| PARP12 | TBXAS1 | 0.864 |
| SAMD9 | TBXAS1 | 0.864 |
| GPAA1 | PLP2 | 0.864 |
| LTA4H | PGD | 0.864 |
| S100A12 | SLC12A9 | 0.864 |
| ADA | IFIT5 | 0.863 |
| CUL1 | PLP2 | 0.863 |
| DDX60 | CAT | 0.863 |
| DNMT1 | OAS3 | 0.863 |
| GZMB | IFIT3 | 0.863 |
| HERC5 | ISG15 | 0.863 |
| HESX1 | OAS2 | 0.863 |
| IFI44 | OASL | 0.863 |
| IFI6 | IFIT1 | 0.863 |
| IFI6 | LY6E | 0.863 |
| IFIH1 | LAX1 | 0.863 |
| IFIT3 | JUP | 0.863 |
| IFIT3 | RTN3 | 0.863 |
| IFIT5 | LTA4H | 0.863 |
| ISG15 | OASL | 0.863 |
| ISG20 | MX1 | 0.863 |
| JUP | SORL1 | 0.863 |
| KCTD14 | EMR1 | 0.863 |
| KCTD14 | FLII | 0.863 |
| KCTD14 | LAPTM5 | 0.863 |
| KCTD14 | SORL1 | 0.863 |
| KCTD14 | STAT5B | 0.863 |
| LY6E | OAS3 | 0.863 |
| OASL | PROS1 | 0.863 |
| PARP12 | ACPP | 0.863 |
| SAMD9 | PYGL | 0.863 |
| CYBRD1 | SLC12A9 | 0.863 |
| LTA4H | NRD1 | 0.863 |
| LTA4H | TBXAS1 | 0.863 |
| RTN3 | SLC12A9 | 0.863 |
| ADA | IFIT3 | 0.862 |
| CHST12 | LY6E | 0.862 |
| CHST12 | NRD1 | 0.862 |
| CUL1 | TBXAS1 | 0.862 |
| CUL1 | TWF2 | 0.862 |
| DDX60 | KCTD14 | 0.862 |
| DHX58 | PGD | 0.862 |
| DHX58 | TBXAS1 | 0.862 |
| DNMT1 | SORL1 | 0.862 |
| EIF2AK2 | IFI6 | 0.862 |
| EIF2AK2 | OAS3 | 0.862 |
| HERC5 | GPAA1 | 0.862 |
| HERC5 | TKT | 0.862 |
| HESX1 | LY6E | 0.862 |
| IFI44L | IFIH1 | 0.862 |
| IFI44L | OAS1 | 0.862 |
| IFI44L | OAS3 | 0.862 |
| IFI6 | CYBRD1 | 0.862 |
| IFIT3 | ISG15 | 0.862 |
| IFIT3 | PROS1 | 0.862 |
| IFIT3 | PYGL | 0.862 |
| IFIT3 | TKT | 0.862 |
| IFIT5 | ISG15 | 0.862 |
| IFIT5 | LAX1 | 0.862 |
| IFIT5 | S100A12 | 0.862 |
| ISG20 | RSAD2 | 0.862 |
| JUP | LY6E | 0.862 |
| MX1 | RSAD2 | 0.862 |
| OAS1 | CYBRD1 | 0.862 |
| OAS2 | RSAD2 | 0.862 |
| PARP12 | ACAA1 | 0.862 |
| STAT1 | HK3 | 0.862 |
| XAF1 | PLP2 | 0.862 |
| ACPP | LTA4H | 0.862 |
| CTSB | GPAA1 | 0.862 |
| RAB31 | STAT5B | 0.862 |
| SORL1 | TSPO | 0.862 |
| ADA | SAMD9 | 0.861 |
| CHST12 | EIF2AK2 | 0.861 |
| CHST12 | TNIP1 | 0.861 |
| CUL1 | LY6E | 0.861 |
| CUL1 | RSAD2 | 0.861 |
| CUL1 | ACPP | 0.861 |
| CUL1 | PTAFR | 0.861 |
| DDX60 | SIGLEC1 | 0.861 |
| DNMT1 | OASL | 0.861 |
| HERC5 | LY6E | 0.861 |
| HESX1 | OAS3 | 0.861 |
| HESX1 | NRD1 | 0.861 |
| IFI44 | IFIT1 | 0.861 |
| IFI6 | ISG20 | 0.861 |
| IFI6 | CAT | 0.861 |
| IFIH1 | TALDO1 | 0.861 |
| IFIT3 | TWF2 | 0.861 |
| ISG20 | SORL1 | 0.861 |
| JUP | OAS2 | 0.861 |
| KCTD14 | HK3 | 0.861 |
| KCTD14 | TWF2 | 0.861 |
| LY6E | CYBRD1 | 0.861 |
| OAS3 | RSAD2 | 0.861 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| OAS3 | CAT | 0.861 |
| OAS3 | PROS1 | 0.861 |
| SAMD9 | STAT5B | 0.861 |
| STAT1 | SLC12A9 | 0.861 |
| XAF1 | IMPA2 | 0.861 |
| GPAA1 | CAT | 0.861 |
| GPAA1 | CYBRD1 | 0.861 |
| EMR1 | GPAA1 | 0.861 |
| GPAA1 | TKT | 0.861 |
| IMPA2 | LTA4H | 0.861 |
| SLC12A9 | SORL1 | 0.861 |
| STAT5B | TBXAS1 | 0.861 |
| IFIT3 | CHST12 | 0.86 |
| OASL | CHST12 | 0.86 |
| CUL1 | NRD1 | 0.86 |
| DDX60 | CTSB | 0.86 |
| DDX60 | TALDO1 | 0.86 |
| DDX60 | TWF2 | 0.86 |
| DHX58 | LAX1 | 0.86 |
| DHX58 | ACPP | 0.86 |
| DHX58 | RAB31 | 0.86 |
| LY6E | DNMT1 | 0.86 |
| SIGLEC1 | DNMT1 | 0.86 |
| HERC5 | CYBRD1 | 0.86 |
| HESX1 | TWF2 | 0.86 |
| MX1 | IFIH1 | 0.86 |
| IFIH1 | FLII | 0.86 |
| IFIH1 | RTN3 | 0.86 |
| IFIH1 | TKT | 0.86 |
| IFIH1 | TWF2 | 0.86 |
| IFIT3 | IFIT1 | 0.86 |
| IFIT2 | IMPA2 | 0.86 |
| LY6E | IFIT3 | 0.86 |
| MX1 | IFIT3 | 0.86 |
| IFIT3 | CTSB | 0.86 |
| IFIT3 | NRD1 | 0.86 |
| IFIT5 | DYSF | 0.86 |
| ISG20 | ACAA1 | 0.86 |
| ISG20 | NINJ2 | 0.86 |
| LAX1 | JUP | 0.86 |
| LAX1 | TNIP1 | 0.86 |
| OAS1 | LY6E | 0.86 |
| SIGLEC1 | OAS1 | 0.86 |
| RSAD2 | OASL | 0.86 |
| SAMD9 | DYSF | 0.86 |
| SIGLEC1 | CAT | 0.86 |
| SIGLEC1 | PROS1 | 0.86 |
| XAF1 | NINJ2 | 0.86 |
| XAF1 | NRD1 | 0.86 |
| XAF1 | TBXAS1 | 0.86 |
| ACAA1 | GPAA1 | 0.86 |
| ACPP | PROS1 | 0.86 |
| ACPP | SORL1 | 0.86 |
| CAT | SLC12A9 | 0.86 |
| EMR1 | SORL1 | 0.86 |
| HK3 | LTA4H | 0.86 |
| MPA2 | INRD1 | 0.86 |
| LTA4H | NINJ2 | 0.86 |
| LTA4H | TWF2 | 0.86 |
| NRD1 | TSPO | 0.86 |
| RTN3 | STAT5B | 0.86 |
| SLC12A9 | TSPO | 0.86 |
| CHST12 | HK3 | 0.859 |
| HERC5 | CUL1 | 0.859 |
| CUL1 | RAB31 | 0.859 |
| KCTD14 | EIF2AK2 | 0.859 |
| KCTD14 | HERC5 | 0.859 |
| HERC5 | CETP | 0.859 |
| RSAD2 | HESX1 | 0.859 |
| HESX1 | TALDO1 | 0.859 |
| HESX1 | TKT | 0.859 |
| IFI6 | IFI44 | 0.859 |
| OAS3 | IFI44 | 0.859 |
| STAT1 | IFI44L | 0.859 |
| IFIH1 | PGD | 0.859 |
| IFIT2 | NINJ2 | 0.859 |
| IFIT2 | RAB31 | 0.859 |
| IFIT2 | TBXAS1 | 0.859 |
| IFIT2 | TSPO | 0.859 |
| IFIT3 | KCTD14 | 0.859 |
| IFIT3 | FLII | 0.859 |
| IFIT3 | LAPTM5 | 0.859 |
| PARP12 | ISG15 | 0.859 |
| SAMD9 | ISG15 | 0.859 |
| ISG20 | PGD | 0.859 |
| JUP | PROS1 | 0.859 |
| XAF1 | LAX1 | 0.859 |
| XAF1 | LY6E | 0.859 |
| OAS3 | MX1 | 0.859 |
| PARP12 | PGD | 0.859 |
| SAMD9 | LTA4H | 0.859 |
| XAF1 | ACAA1 | 0.859 |
| IMPA2 | STAT5B | 0.859 |
| LTA4H | RTN3 | 0.859 |
| PROS1 | SLC12A9 | 0.859 |
| S100A12 | SORT1 | 0.859 |
| SORL1 | TBXAS1 | 0.859 |
| SORL1 | TWF2 | 0.859 |
| HESX1 | ADA | 0.858 |
| XAF1 | ADA | 0.858 |
| HESX1 | CHST12 | 0.858 |
| IFI6 | CUL1 | 0.858 |
| DDX60 | GPAA1 | 0.858 |
| DDX60 | LAPTM5 | 0.858 |
| DDX60 | PROS1 | 0.858 |
| DHX58 | GPAA1 | 0.858 |
| IFIT3 | DNMT1 | 0.858 |
| XAF1 | DNMT1 | 0.858 |
| EIF2AK2 | PROS1 | 0.858 |
| XAF1 | GZMB | 0.858 |
| GZMB | RAB31 | 0.858 |
| HESX1 | LAPTM5 | 0.858 |
| IFIT3 | IFI44L | 0.858 |
| RSAD2 | IFIT1 | 0.858 |
| IFIT3 | TNIP1 | 0.858 |
| IFIT5 | NINJ2 | 0.858 |
| IFIT5 | TBXAS1 | 0.858 |
| SIGLEC1 | ISG20 | 0.858 |
| ISG20 | EMR1 | 0.858 |
| ISG20 | TALDO1 | 0.858 |
| OAS1 | JUP | 0.858 |
| KCTD14 | DYSF | 0.858 |
| SAMD9 | LY6E | 0.858 |
| STAT1 | LY6E | 0.858 |
| OASL | MX1 | 0.858 |
| OASL | NRD1 | 0.858 |
| STAT1 | SORL1 | 0.858 |
| STAT1 | TSPO | 0.858 |
| XAF1 | TNIP1 | 0.858 |
| ACPP | FLII | 0.858 |
| ACPP | TNIP1 | 0.858 |
| SLC12A9 | TNIP1 | 0.858 |
| SORL1 | SORT1 | 0.858 |
| DHX58 | ADA | 0.857 |
| OAS2 | CUL1 | 0.857 |
| CUL1 | HK3 | 0.857 |
| CUL1 | PGD | 0.857 |
| DDX60 | FLII | 0.857 |
| DDX60 | TNIP1 | 0.857 |
| DHX58 | NINJ2 | 0.857 |
| OAS1 | DNMT1 | 0.857 |
| RSAD2 | EIF2AK2 | 0.857 |
| EIF2AK2 | CAT | 0.857 |
| KCTD14 | GZMB | 0.857 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| GZMB | IMPA2 | 0.857 |
| IFI44L | HERC5 | 0.857 |
| IFIT5 | IFI44L | 0.857 |
| PARP12 | IFI44L | 0.857 |
| SAMD9 | IFI44L | 0.857 |
| IFIT3 | IFI6 | 0.857 |
| OAS3 | IFI6 | 0.857 |
| IFIH1 | CTSB | 0.857 |
| IFIH1 | GPAA1 | 0.857 |
| IFIH1 | NINJ2 | 0.857 |
| IFIT2 | SORT1 | 0.857 |
| IFIT3 | CAT | 0.857 |
| IFIT5 | NRD1 | 0.857 |
| XAF1 | JUP | 0.857 |
| KCTD14 | NINJ2 | 0.857 |
| PARP12 | DOK3 | 0.857 |
| PARP12 | LAPTM5 | 0.857 |
| SAMD9 | ACAA1 | 0.857 |
| STAT1 | PTAFR | 0.857 |
| XAF1 | DOK3 | 0.857 |
| XAF1 | PGD | 0.857 |
| ACAA1 | SORL1 | 0.857 |
| ACPP | CETP | 0.857 |
| ACPP | RTN3 | 0.857 |
| CYBRD1 | STAT5B | 0.857 |
| GPAA1 | NINJ2 | 0.857 |
| GPAA1 | SORT1 | 0.857 |
| IMPA2 | S100A12 | 0.857 |
| NRD1 | TBXAS1 | 0.857 |
| STAT5B | TSPO | 0.857 |
| ADA | LTA4H | 0.856 |
| CHST12 | CTSB | 0.856 |
| CHST12 | DOK3 | 0.856 |
| CHST12 | DYSF | 0.856 |
| EIF2AK2 | CUL1 | 0.856 |
| OAS3 | CUL1 | 0.856 |
| CUL1 | TALDO1 | 0.856 |
| RSAD2 | DDX60 | 0.856 |
| DDX60 | RTN3 | 0.856 |
| DHX58 | LTA4H | 0.856 |
| DNMT1 | STAT5B | 0.856 |
| GZMB | SORL1 | 0.856 |
| OAS2 | HERC5 | 0.856 |
| IFIT1 | HESX1 | 0.856 |
| OAS1 | IFI44 | 0.856 |
| IFIT2 | IFI44L | 0.856 |
| LY6E | IFIH1 | 0.856 |
| IFIT2 | S100A12 | 0.856 |
| RSAD2 | IFIT3 | 0.856 |
| SIGLEC1 | IFIT3 | 0.856 |
| XAF1 | ISG15 | 0.856 |
| ISG20 | LY6E | 0.856 |
| ISG20 | ACPP | 0.856 |
| ISG20 | NRD1 | 0.856 |
| ISG20 | TWF2 | 0.856 |
| KCTD14 | LY6E | 0.856 |
| OAS2 | KCTD14 | 0.856 |
| OAS1 | MX1 | 0.856 |
| PARP12 | NRD1 | 0.856 |
| PARP12 | TNIP1 | 0.856 |
| XAF1 | CTSB | 0.856 |
| XAF1 | S100A12 | 0.856 |
| ACPP | CTSB | 0.856 |
| ACPP | SORT1 | 0.856 |
| CAT | EMR1 | 0.856 |
| LTA4H | TALDO1 | 0.856 |
| PLP2 | STAT5B | 0.856 |
| KCTD14 | ADA | 0.855 |
| ADA | EMR1 | 0.855 |
| CHST12 | TKT | 0.855 |
| CUL1 | FLII | 0.855 |
| CUL1 | RTN3 | 0.855 |
| DDX60 | TKT | 0.855 |
| GZMB | DHX58 | 0.855 |
| IFIT1 | DHX58 | 0.855 |
| DNMT1 | TWF2 | 0.855 |
| GZMB | PLP2 | 0.855 |
| GZMB | S100A12 | 0.855 |
| GZMB | TKT | 0.855 |
| MX1 | HERC5 | 0.855 |
| SIGLEC1 | IFIH1 | 0.855 |
| IFIH1 | TNIP1 | 0.855 |
| OAS1 | IFIT1 | 0.855 |
| OAS3 | IFIT1 | 0.855 |
| OASL | IFIT1 | 0.855 |
| IFIT2 | PYGL | 0.855 |
| IFIT3 | OAS2 | 0.855 |
| IFIT3 | GPAA1 | 0.855 |
| IFIT5 | PTAFR | 0.855 |
| IFIT5 | PYGL | 0.855 |
| OAS2 | ISG20 | 0.855 |
| OAS1 | KCTD14 | 0.855 |
| LAX1 | FLII | 0.855 |
| LAX1 | IMPA2 | 0.855 |
| LAX1 | PGD | 0.855 |
| STAT1 | EMR1 | 0.855 |
| STAT1 | SORT1 | 0.855 |
| XAF1 | TALDO1 | 0.855 |
| XAF1 | TWF2 | 0.855 |
| CETP | STAT5B | 0.855 |
| GPAA1 | HK3 | 0.855 |
| GPAA1 | PYGL | 0.855 |
| IMPA2 | SLC12A9 | 0.855 |
| LAPTM5 | SORL1 | 0.855 |
| LTA4H | RAB31 | 0.855 |
| LTA4H | S100A12 | 0.855 |
| RAB31 | SORL1 | 0.855 |
| SORT1 | STAT5B | 0.855 |
| PARP12 | ADA | 0.854 |
| CHST12 | RAB31 | 0.854 |
| CUL1 | DYSF | 0.854 |
| IFI44L | DDX60 | 0.854 |
| DHX58 | TNIP1 | 0.854 |
| DHX58 | TWF2 | 0.854 |
| HESX1 | EIF2AK2 | 0.854 |
| EIF2AK2 | JUP | 0.854 |
| JUP | GZMB | 0.854 |
| GZMB | GPAA1 | 0.854 |
| GZMB | TALDO1 | 0.854 |
| GZMB | TBXAS1 | 0.854 |
| HESX1 | HERC5 | 0.854 |
| IFIT1 | HERC5 | 0.854 |
| OAS1 | HESX1 | 0.854 |
| HESX1 | PYGL | 0.854 |
| XAF1 | IFI44L | 0.854 |
| IFIH1 | CAT | 0.854 |
| IFIH1 | CETP | 0.854 |
| IFIT3 | CETP | 0.854 |
| IFIT5 | ACAA1 | 0.854 |
| STAT1 | ISG15 | 0.854 |
| ISG20 | FLII | 0.854 |
| ISG20 | LAPTM5 | 0.854 |
| ISG20 | TBXAS1 | 0.854 |
| SAMD9 | JUP | 0.854 |
| JUP | CAT | 0.854 |
| KCTD14 | CTSB | 0.854 |
| OAS2 | OAS1 | 0.854 |
| OAS3 | OAS2 | 0.854 |
| PARP12 | PYGL | 0.854 |
| PARP12 | TWF2 | 0.854 |
| SAMD9 | NRD1 | 0.854 |
| XAF1 | LAPTM5 | 0.854 |
| XAF1 | RAB31 | 0.854 |
| CTSB | TSPO | 0.854 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| DYSF | LTA4H | 0.854 |
| EMR1 | RTN3 | 0.854 |
| EMR1 | STAT5B | 0.854 |
| PLP2 | SLC12A9 | 0.854 |
| S100A12 | STAT5B | 0.854 |
| IFIT1 | DDX60 | 0.853 |
| MX1 | DDX60 | 0.853 |
| DDX60 | CETP | 0.853 |
| MX1 | DHX58 | 0.853 |
| PARP12 | DNMT1 | 0.853 |
| DNMT1 | SLC12A9 | 0.853 |
| DNMT1 | TKT | 0.853 |
| GZMB | CTSB | 0.853 |
| GZMB | SLC12A9 | 0.853 |
| IFI44 | HERC5 | 0.853 |
| ISG20 | HERC5 | 0.853 |
| HESX1 | TNIP1 | 0.853 |
| PARP12 | IFI44 | 0.853 |
| OAS1 | IFI6 | 0.853 |
| OAS2 | IFIH1 | 0.853 |
| IFIT3 | CYBRD1 | 0.853 |
| IFIT5 | DOK3 | 0.853 |
| IFIT5 | RTN3 | 0.853 |
| ISG20 | DYSF | 0.853 |
| KCTD14 | PYGL | 0.853 |
| RSAD2 | OAS1 | 0.853 |
| PARP12 | FLII | 0.853 |
| PARP12 | S100A12 | 0.853 |
| SAMD9 | PGD | 0.853 |
| SIGLEC1 | CYBRD1 | 0.853 |
| STAT1 | IMPA2 | 0.853 |
| XAF1 | LTA4H | 0.853 |
| CYBRD1 | SORL1 | 0.853 |
| DYSF | GPAA1 | 0.853 |
| EMR1 | SLC12A9 | 0.853 |
| IFIH1 | ADA | 0.852 |
| ADA | TWF2 | 0.852 |
| CUL1 | SORT1 | 0.852 |
| CUL1 | STAT5B | 0.852 |
| IFI44L | DHX58 | 0.852 |
| DHX58 | PYGL | 0.852 |
| DNMT1 | IMPA2 | 0.852 |
| EIF2AK2 | CYBRD1 | 0.852 |
| HESX1 | GZMB | 0.852 |
| GZMB | TWF2 | 0.852 |
| RSAD2 | HERC5 | 0.852 |
| OASL | IFI6 | 0.852 |
| LAX1 | IFIT2 | 0.852 |
| IFIT2 | CTSB | 0.852 |
| LY6E | IFIT5 | 0.852 |
| IFIT5 | CAT | 0.852 |
| ISG20 | HK3 | 0.852 |
| OASL | OAS2 | 0.852 |
| PARP12 | RTN3 | 0.852 |
| PARP12 | TKT | 0.852 |
| SAMD9 | NINJ2 | 0.852 |
| SAMD9 | PLP2 | 0.852 |
| SIGLEC1 | STAT1 | 0.852 |
| STAT1 | DYSF | 0.852 |
| XAF1 | FLII | 0.852 |
| XAF1 | TKT | 0.852 |
| ACPP | IMPA2 | 0.852 |
| CAT | SORL1 | 0.852 |
| CETP | SORT1 | 0.852 |
| CTSB | LTA4H | 0.852 |
| CTSB | RAB31 | 0.852 |
| DOK3 | LTA4H | 0.852 |
| EMR1 | IMPA2 | 0.852 |
| FLII | S100A12 | 0.852 |
| GPAA1 | TNIP1 | 0.852 |
| IMPA2 | SORL1 | 0.852 |
| NINJ2 | SORL1 | 0.852 |
| STAT5B | TWF2 | 0.852 |
| CHST12 | IFIH1 | 0.851 |
| CHST12 | S100A12 | 0.851 |
| IFI44 | DHX58 | 0.851 |
| DHX58 | CTSB | 0.851 |
| DHX58 | NRD1 | 0.851 |
| DHX58 | RTN3 | 0.851 |
| SAMD9 | DNMT1 | 0.851 |
| EIF2AK2 | ISG20 | 0.851 |
| IFIT2 | GZMB | 0.851 |
| GZMB | HK3 | 0.851 |
| GZMB | NINJ2 | 0.851 |
| GZMB | PROS1 | 0.851 |
| HESX1 | CETP | 0.851 |
| IFIT3 | IFI44 | 0.851 |
| IFIH1 | IFI6 | 0.851 |
| IFIT2 | LTA4H | 0.851 |
| IFIT2 | PGD | 0.851 |
| IFIT2 | PLP2 | 0.851 |
| IFIT5 | RSAD2 | 0.851 |
| IFIT5 | CYBRD1 | 0.851 |
| ISG20 | OAS3 | 0.851 |
| ISG20 | CETP | 0.851 |
| JUP | SORT1 | 0.851 |
| LAX1 | TSPO | 0.851 |
| LY6E | OASL | 0.851 |
| MX1 | XAF1 | 0.851 |
| OAS1 | OAS3 | 0.851 |
| OAS2 | XAF1 | 0.851 |
| PARP12 | TALDO1 | 0.851 |
| STAT1 | TBXAS1 | 0.851 |
| XAF1 | GPAA1 | 0.851 |
| XAF1 | RTN3 | 0.851 |
| SLC12A9 | LAPTM5 | 0.851 |
| NRD1 | SLC12A9 | 0.851 |
| RTN3 | SORL1 | 0.851 |
| S100A12 | TBXAS1 | 0.851 |
| SLC12A9 | TWF2 | 0.851 |
| TNIP1 | SORL1 | 0.851 |
| ADA | SLC12A9 | 0.85 |
| CHST12 | SAMD9 | 0.85 |
| CHST12 | CETP | 0.85 |
| CUL1 | TKT | 0.85 |
| DDX60 | EIF2AK2 | 0.85 |
| DHX58 | SIGLEC1 | 0.85 |
| GZMB | ACAA1 | 0.85 |
| GZMB | ACPP | 0.85 |
| GZMB | FLII | 0.85 |
| GZMB | PYGL | 0.85 |
| IFIH1 | RSAD2 | 0.85 |
| IFIT1 | XAF1 | 0.85 |
| IFIT2 | RTN3 | 0.85 |
| IFIT5 | MX1 | 0.85 |
| ISG20 | TKT | 0.85 |
| KCTD14 | XAF1 | 0.85 |
| MX1 | PARP12 | 0.85 |
| OAS3 | CYBRD1 | 0.85 |
| OASL | CAT | 0.85 |
| OASL | CYBRD1 | 0.85 |
| PARP12 | GPAA1 | 0.85 |
| RSAD2 | XAF1 | 0.85 |
| SIGLEC1 | XAF1 | 0.85 |
| STAT1 | LTA4H | 0.85 |
| ACAA1 | RTN3 | 0.85 |
| ACPP | CAT | 0.85 |
| ACPP | PGD | 0.85 |
| ACPP | SLC12A9 | 0.85 |
| CAT | IMPA2 | 0.85 |
| CTSB | IMPA2 | 0.85 |
| EMR1 | S100A12 | 0.85 |
| GPAA1 | PGD | 0.85 |
| NINJ2 | SLC12A9 | 0.85 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| S100A12 | TWF2 | 0.85 |
| CHST12 | NINJ2 | 0.849 |
| CUL1 | CTSB | 0.849 |
| CUL1 | NINJ2 | 0.849 |
| DDX60 | OASL | 0.849 |
| DHX58 | ISG15 | 0.849 |
| DHX58 | OAS2 | 0.849 |
| DHX58 | RSAD2 | 0.849 |
| DHX58 | FLII | 0.849 |
| DNMT1 | TSPO | 0.849 |
| EIF2AK2 | HERC5 | 0.849 |
| EIF2AK2 | IFIT3 | 0.849 |
| GZMB | PARP12 | 0.849 |
| GZMB | CETP | 0.849 |
| HERC5 | IFI6 | 0.849 |
| HERC5 | OAS3 | 0.849 |
| HESX1 | NINJ2 | 0.849 |
| IFIT1 | IFIT5 | 0.849 |
| IFIT2 | TALDO1 | 0.849 |
| IFIT5 | SIGLEC1 | 0.849 |
| IFIT5 | CTSB | 0.849 |
| IFIT5 | PGD | 0.849 |
| IFIT5 | PROS1 | 0.849 |
| JUP | OASL | 0.849 |
| KCTD14 | S100A12 | 0.849 |
| LAX1 | PTAFR | 0.849 |
| PARP12 | RSAD2 | 0.849 |
| SAMD9 | CAT | 0.849 |
| XAF1 | PYGL | 0.849 |
| ACPP | NRD1 | 0.849 |
| LTA4H | PTAFR | 0.849 |
| ADA | IFIT2 | 0.848 |
| CHST12 | JUP | 0.848 |
| CHST12 | XAF1 | 0.848 |
| CUL1 | IFIT3 | 0.848 |
| CUL1 | CAT | 0.848 |
| DDX60 | CYBRD1 | 0.848 |
| DHX58 | LAPTM5 | 0.848 |
| DNMT1 | TALDO1 | 0.848 |
| EIF2AK2 | OAS1 | 0.848 |
| GZMB | IFIH1 | 0.848 |
| GZMB | DYSF | 0.848 |
| HERC5 | IFIT3 | 0.848 |
| IFI6 | PARP12 | 0.848 |
| IFIH1 | IFIT1 | 0.848 |
| IFIH1 | LAPTM5 | 0.848 |
| IFIT2 | MX1 | 0.848 |
| ISG20 | DOK3 | 0.848 |
| ISG20 | PTAFR | 0.848 |
| JUP | STAT1 | 0.848 |
| LAX1 | ACAA1 | 0.848 |
| LAX1 | TBXAS1 | 0.848 |
| LAX1 | TKT | 0.848 |
| LY6E | PARP12 | 0.848 |
| OAS2 | SAMD9 | 0.848 |
| PARP12 | CETP | 0.848 |
| STAT1 | ACPP | 0.848 |
| ACPP | LAPTM5 | 0.848 |
| ACPP | PLP2 | 0.848 |
| CAT | LTA4H | 0.848 |
| CETP | GPAA1 | 0.848 |
| CYBRD1 | EMR1 | 0.848 |
| PLP2 | NRD1 | 0.848 |
| PROS1 | STAT5B | 0.848 |
| S100A12 | TNIP1 | 0.848 |
| SLC12A9 | TALDO1 | 0.848 |
| SLC12A9 | TBXAS1 | 0.848 |
| SLC12A9 | TKT | 0.848 |
| STAT5B | TALDO1 | 0.848 |
| STAT5B | TKT | 0.848 |
| ADA | TNIP1 | 0.847 |
| DHX58 | CHST12 | 0.847 |
| CHST12 | TALDO1 | 0.847 |
| CUL1 | EMR1 | 0.847 |
| IFI44 | DDX60 | 0.847 |
| IFI6 | DDX60 | 0.847 |
| JUP | DHX58 | 0.847 |
| IFIT5 | DNMT1 | 0.847 |
| DNMT1 | CETP | 0.847 |
| OASL | HERC5 | 0.847 |
| HESX1 | CAT | 0.847 |
| IFIH1 | IFI44 | 0.847 |
| XAF1 | IFI44 | 0.847 |
| XAF1 | IFI6 | 0.847 |
| IFIT2 | DOK3 | 0.847 |
| OAS2 | IFIT5 | 0.847 |
| IFIT5 | TNIP1 | 0.847 |
| LAX1 | LAPTM5 | 0.847 |
| LAX1 | NRD1 | 0.847 |
| SAMD9 | MX1 | 0.847 |
| STAT1 | MX1 | 0.847 |
| PARP12 | SIGLEC1 | 0.847 |
| SAMD9 | CTSB | 0.847 |
| SAMD9 | DOK3 | 0.847 |
| ACPP | TSPO | 0.847 |
| CYBRD1 | IMPA2 | 0.847 |
| PGD | EMR1 | 0.847 |
| PYGL | EMR1 | 0.847 |
| GPAA1 | PROS1 | 0.847 |
| IMPA2 | SORT1 | 0.847 |
| LAPTM5 | NRD1 | 0.847 |
| PLP2 | RTN3 | 0.847 |
| PROS1 | SORL1 | 0.847 |
| RAB31 | TBXAS1 | 0.847 |
| S100A12 | TSPO | 0.847 |
| JUP | ADA | 0.846 |
| ADA | IMPA2 | 0.846 |
| ADA | TBXAS1 | 0.846 |
| ADA | TSPO | 0.846 |
| KCTD14 | CHST12 | 0.846 |
| CHST12 | CAT | 0.846 |
| CHST12 | RTN3 | 0.846 |
| OAS1 | CUL1 | 0.846 |
| OASL | CUL1 | 0.846 |
| CUL1 | PYGL | 0.846 |
| ISG20 | DDX60 | 0.846 |
| OAS1 | DDX60 | 0.846 |
| IFIH1 | DNMT1 | 0.846 |
| DNMT1 | NRD1 | 0.846 |
| IFIH1 | EIF2AK2 | 0.846 |
| GZMB | TNIP1 | 0.846 |
| OAS1 | HERC5 | 0.846 |
| JUP | HESX1 | 0.846 |
| PARP12 | IFIT1 | 0.846 |
| STAT1 | IFIT1 | 0.846 |
| ISG20 | RTN3 | 0.846 |
| ISG20 | S100A12 | 0.846 |
| LAX1 | PLP2 | 0.846 |
| SAMD9 | RSAD2 | 0.846 |
| SAMD9 | PROS1 | 0.846 |
| STAT1 | ACAA1 | 0.846 |
| STAT1 | PYGL | 0.846 |
| ACAA1 | NRD1 | 0.846 |
| ACAA1 | STAT5B | 0.846 |
| CETP | SORL1 | 0.846 |
| IMPA2 | TNIP1 | 0.846 |
| LTA4H | TKT | 0.846 |
| NRD1 | PGD | 0.846 |
| NRD1 | RTN3 | 0.846 |
| PGD | SLC12A9 | 0.846 |
| PGD | STAT5B | 0.846 |
| SLC12A9 | SORT1 | 0.846 |
| ADA | ACPP | 0.845 |
| CUL1 | S100A12 | 0.845 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| DNMT1 | DHX58 | 0.845 |
| DHX58 | S100A12 | 0.845 |
| DNMT1 | CAT | 0.845 |
| GZMB | CAT | 0.845 |
| GZMB | EMR1 | 0.845 |
| GZMB | PTAFR | 0.845 |
| IFIT3 | HESX1 | 0.845 |
| SIGLEC1 | HESX1 | 0.845 |
| JUP | IFIH1 | 0.845 |
| ISG15 | IFIT2 | 0.845 |
| IFIT2 | PROS1 | 0.845 |
| IFIT5 | TALDO1 | 0.845 |
| IFIT5 | TKT | 0.845 |
| OAS1 | ISG20 | 0.845 |
| ISG20 | CTSB | 0.845 |
| JUP | CYBRD1 | 0.845 |
| KCTD14 | CAT | 0.845 |
| LAX1 | ACPP | 0.845 |
| LAX1 | EMR1 | 0.845 |
| OASL | OAS3 | 0.845 |
| PARP12 | CYBRD1 | 0.845 |
| SAMD9 | CYBRD1 | 0.845 |
| STAT1 | S100A12 | 0.845 |
| CYBRD1 | SORT1 | 0.845 |
| EMR1 | RAB31 | 0.845 |
| NRD1 | TWF2 | 0.845 |
| PLP2 | TSPO | 0.845 |
| PYGL | SLC12A9 | 0.845 |
| RAB31 | TSPO | 0.845 |
| RTN3 | TBXAS1 | 0.845 |
| SORT1 | TSPO | 0.845 |
| IFIT5 | CHST12 | 0.844 |
| PARP12 | CHST12 | 0.844 |
| CUL1 | TNIP1 | 0.844 |
| OAS3 | DDX60 | 0.844 |
| IFI6 | DHX58 | 0.844 |
| IFIH1 | DHX58 | 0.844 |
| HESX1 | DNMT1 | 0.844 |
| DNMT1 | PGD | 0.844 |
| IFIH1 | HERC5 | 0.844 |
| OAS3 | IFIT3 | 0.844 |
| OASL | IFIT3 | 0.844 |
| IFIT5 | TWF2 | 0.844 |
| OASL | ISG20 | 0.844 |
| ISG20 | CAT | 0.844 |
| ISG20 | PYGL | 0.844 |
| OASL | KCTD14 | 0.844 |
| PARP12 | KCTD14 | 0.844 |
| STAT1 | OAS2 | 0.844 |
| XAF1 | OAS3 | 0.844 |
| PARP12 | CAT | 0.844 |
| PARP12 | PROS1 | 0.844 |
| XAF1 | CAT | 0.844 |
| XAF1 | CETP | 0.844 |
| XAF1 | PROS1 | 0.844 |
| ACAA1 | SLC12A9 | 0.844 |
| CTSB | SORL1 | 0.844 |
| CTSB | STAT5B | 0.844 |
| EMR1 | PROS1 | 0.844 |
| EMR1 | TSPO | 0.844 |
| FLII | RAB31 | 0.844 |
| FLII | SORL1 | 0.844 |
| GPAA1 | LAPTM5 | 0.844 |
| MPA2 | IPLP2 | 0.844 |
| IMPA2 | TSPO | 0.844 |
| RAB31 | SORT1 | 0.844 |
| RAB31 | TNIP1 | 0.844 |
| TBXAS1 | TNIP1 | 0.844 |
| HESX1 | DDX60 | 0.843 |
| IFIT3 | DDX60 | 0.843 |
| DHX58 | TKT | 0.843 |
| DNMT1 | TBXAS1 | 0.843 |
| OASL | HESX1 | 0.843 |
| IFIT5 | IFI44 | 0.843 |
| IFIH1 | CYBRD1 | 0.843 |
| IFIT2 | TKT | 0.843 |
| OAS3 | IFIT5 | 0.843 |
| IFIT5 | LAPTM5 | 0.843 |
| ISG20 | SORT1 | 0.843 |
| LAX1 | CETP | 0.843 |
| OASL | OAS1 | 0.843 |
| PARP12 | OAS2 | 0.843 |
| XAF1 | CYBRD1 | 0.843 |
| ACAA1 | CAT | 0.843 |
| ACPP | TALDO1 | 0.843 |
| CAT | TNIP1 | 0.843 |
| CETP | EMR1 | 0.843 |
| CETP | LTA4H | 0.843 |
| CTSB | SORT1 | 0.843 |
| CYBRD1 | LTA4H | 0.843 |
| CYBRD1 | PLP2 | 0.843 |
| EMR1 | NRD1 | 0.843 |
| IMPA2 | RAB31 | 0.843 |
| IMPA2 | RTN3 | 0.843 |
| LTA4H | PYGL | 0.843 |
| NINJ2 | PGD | 0.843 |
| NINJ2 | STAT5B | 0.843 |
| NINJ2 | TSPO | 0.843 |
| PROS1 | SORT1 | 0.843 |
| RTN3 | S100A12 | 0.843 |
| RTN3 | SORT1 | 0.843 |
| RTN3 | TSPO | 0.843 |
| SORL1 | TKT | 0.843 |
| ADA | FLII | 0.842 |
| CHST12 | PYGL | 0.842 |
| DDX60 | CUL1 | 0.842 |
| HERC5 | DDX60 | 0.842 |
| PARP12 | DDX60 | 0.842 |
| LY6E | DHX58 | 0.842 |
| EIF2AK2 | OASL | 0.842 |
| GZMB | NRD1 | 0.842 |
| HESX1 | CYBRD1 | 0.842 |
| IFI44 | STAT1 | 0.842 |
| IFI6 | IFIT5 | 0.842 |
| IFIH1 | PROS1 | 0.842 |
| OAS2 | IFIT2 | 0.842 |
| OAS1 | IFIT3 | 0.842 |
| IFIT5 | CETP | 0.842 |
| PARP12 | JUP | 0.842 |
| KCTD14 | CYBRD1 | 0.842 |
| KCTD14 | PROS1 | 0.842 |
| STAT1 | LAX1 | 0.842 |
| LAX1 | CTSB | 0.842 |
| LAX1 | DYSF | 0.842 |
| XAF1 | OASL | 0.842 |
| STAT1 | RSAD2 | 0.842 |
| STAT1 | NINJ2 | 0.842 |
| STAT1 | RAB31 | 0.842 |
| CAT | SORT1 | 0.842 |
| CAT | TSPO | 0.842 |
| CETP | TBXAS1 | 0.842 |
| CTSB | PLP2 | 0.842 |
| DOK3 | SORL1 | 0.842 |
| EMR1 | PLP2 | 0.842 |
| EMR1 | TNIP1 | 0.842 |
| LTA4H | PROS1 | 0.842 |
| PLP2 | PYGL | 0.842 |
| TSPO | TWF2 | 0.842 |
| HESX1 | CUL1 | 0.841 |
| OAS3 | DHX58 | 0.841 |
| KCTD14 | DNMT1 | 0.841 |
| GZMB | CYBRD1 | 0.841 |
| GZMB | LAPTM5 | 0.841 |
| XAF1 | HESX1 | 0.841 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
| --- | --- | --- |
| HESX1 | S100A12 | 0.841 |
| SAMD9 | IFI44 | 0.841 |
| SAMD9 | IFI6 | 0.841 |
| OASL | IFIH1 | 0.841 |
| SAMD9 | IFIT1 | 0.841 |
| LY6E | IFIT2 | 0.841 |
| IFIT2 | STAT5B | 0.841 |
| JUP | IFIT5 | 0.841 |
| LAX1 | TWF2 | 0.841 |
| XAF1 | OAS1 | 0.841 |
| PARP12 | OAS3 | 0.841 |
| SIGLEC1 | OASL | 0.841 |
| STAT1 | PLP2 | 0.841 |
| STAT1 | STAT5B | 0.841 |
| ACPP | RAB31 | 0.841 |
| DYSF | TBXAS1 | 0.841 |
| EMR1 | TALDO1 | 0.841 |
| GPAA1 | PTAFR | 0.841 |
| NINJ2 | SORT1 | 0.841 |
| PLP2 | SORT1 | 0.841 |
| SORL1 | TALDO1 | 0.841 |
| TNIP1 | TSPO | 0.841 |
| ADA | ACAA1 | 0.84 |
| ADA | STAT5B | 0.84 |
| OAS1 | DHX58 | 0.84 |
| DNMT1 | ACAA1 | 0.84 |
| DNMT1 | TNIP1 | 0.84 |
| SAMD9 | GZMB | 0.84 |
| XAF1 | HERC5 | 0.84 |
| ISG20 | HESX1 | 0.84 |
| IFIT2 | IFI44 | 0.84 |
| IFIT2 | IFIT1 | 0.84 |
| RSAD2 | IFIT2 | 0.84 |
| SIGLEC1 | IFIT2 | 0.84 |
| KCTD14 | IFIT5 | 0.84 |
| LAX1 | DOK3 | 0.84 |
| PARP12 | OAS1 | 0.84 |
| ACPP | TBXAS1 | 0.84 |
| ACPP | TKT | 0.84 |
| CAT | PLP2 | 0.84 |
| CAT | STAT5B | 0.84 |
| CAT | TBXAS1 | 0.84 |
| CTSB | EMR1 | 0.84 |
| CYBRD1 | TNIP1 | 0.84 |
| FLII | SLC12A9 | 0.84 |
| HK3 | NINJ2 | 0.84 |
| HK3 | SORL1 | 0.84 |
| IMPA2 | PGD | 0.84 |
| LAPTM5 | STAT5B | 0.84 |
| PGD | SORL1 | 0.84 |
| PLP2 | TBXAS1 | 0.84 |
| PROS1 | TBXAS1 | 0.84 |
| PYGL | STAT5B | 0.84 |
| RTN3 | TNIP1 | 0.84 |
| S100A12 | TALDO1 | 0.84 |
| SLC12A9 | STAT5B | 0.84 |
| ADA | PTAFR | 0.839 |
| JUP | CUL1 | 0.839 |
| XAF1 | CUL1 | 0.839 |
| HERC5 | DHX58 | 0.839 |
| PARP12 | EIF2AK2 | 0.839 |
| OAS1 | IFIH1 | 0.839 |
| JUP | ISG20 | 0.839 |
| ISG20 | PROS1 | 0.839 |
| LAX1 | TALDO1 | 0.839 |
| STAT1 | PGD | 0.839 |
| ACAA1 | IMPA2 | 0.839 |
| ACAA1 | TBXAS1 | 0.839 |
| ACPP | DYSF | 0.839 |
| ACPP | NINJ2 | 0.839 |
| ACPP | TWF2 | 0.839 |
| CAT | FLII | 0.839 |
| CAT | PGD | 0.839 |
| CYBRD1 | DYSF | 0.839 |
| CYBRD1 | TSPO | 0.839 |
| DYSF | NINJ2 | 0.839 |
| NRD1 | RAB31 | 0.839 |
| NRD1 | SORL1 | 0.839 |
| SORT1 | NRD1 | 0.839 |
| NRD1 | TKT | 0.839 |
| PLP2 | S100A12 | 0.839 |
| S100A12 | TKT | 0.839 |
| ADA | CETP | 0.838 |
| ADA | TKT | 0.838 |
| IFIT2 | CHST12 | 0.838 |
| CHST12 | CYBRD1 | 0.838 |
| CUL1 | CETP | 0.838 |
| IFIH1 | DDX60 | 0.838 |
| DNMT1 | ACPP | 0.838 |
| DNMT1 | PTAFR | 0.838 |
| HESX1 | PROS1 | 0.838 |
| IFI6 | IFIT2 | 0.838 |
| IFIH1 | OAS3 | 0.838 |
| JUP | IFIT2 | 0.838 |
| IFIT2 | ACAA1 | 0.838 |
| IFIT2 | CAT | 0.838 |
| IFIT2 | CYBRD1 | 0.838 |
| LAX1 | S100A12 | 0.838 |
| SAMD9 | TALDO1 | 0.838 |
| SAMD9 | TWF2 | 0.838 |
| ACAA1 | CETP | 0.838 |
| ACAA1 | SORT1 | 0.838 |
| CTSB | RTN3 | 0.838 |
| SLC12A9 | CTSB | 0.838 |
| GPAA1 | DOK3 | 0.838 |
| FLII | NRD1 | 0.838 |
| GPAA1 | TWF2 | 0.838 |
| IMPA2 | NINJ2 | 0.838 |
| IMPA2 | PYGL | 0.838 |
| NRD1 | STAT5B | 0.838 |
| PYGL | SORL1 | 0.838 |
| RAB31 | TWF2 | 0.838 |
| CUL1 | DOK3 | 0.837 |
| IFIT3 | DHX58 | 0.837 |
| EIF2AK2 | XAF1 | 0.837 |
| IFIT5 | GZMB | 0.837 |
| GZMB | DOK3 | 0.837 |
| PARP12 | HERC5 | 0.837 |
| IFIT2 | NRD1 | 0.837 |
| IFIT3 | ISG20 | 0.837 |
| LAX1 | PYGL | 0.837 |
| OASL | PARP12 | 0.837 |
| STAT1 | OASL | 0.837 |
| STAT1 | TALDO1 | 0.837 |
| ACAA1 | ACPP | 0.837 |
| ACAA1 | CTSB | 0.837 |
| ACAA1 | PYGL | 0.837 |
| ACPP | S100A12 | 0.837 |
| DYSF | NRD1 | 0.837 |
| TBXAS1 | EMR1 | 0.837 |
| EMR1 | TKT | 0.837 |
| HK3 | RTN3 | 0.837 |
| IMPA2 | LAPTM5 | 0.837 |
| PYGL | SORT1 | 0.837 |
| TBXAS1 | SORT1 | 0.837 |
| TBXAS1 | TSPO | 0.837 |
| ADA | CTSB | 0.836 |
| CUL1 | LAPTM5 | 0.836 |
| XAF1 | DDX60 | 0.836 |
| DNMT1 | DYSF | 0.836 |
| DNMT1 | PLP2 | 0.836 |
| DNMT1 | RAB31 | 0.836 |
| GZMB | STAT5B | 0.836 |
| IFIT2 | CETP | 0.836 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| IFIT2 | FLII | 0.836 |
| IFIT5 | FLII | 0.836 |
| IFIT5 | GPAA1 | 0.836 |
| XAF1 | ISG20 | 0.836 |
| LAX1 | RAB31 | 0.836 |
| SAMD9 | GPAA1 | 0.836 |
| STAT1 | CTSB | 0.836 |
| ACAA1 | CYBRD1 | 0.836 |
| ACAA1 | TSPO | 0.836 |
| CYBRD1 | ACPP | 0.836 |
| ACPP | HK3 | 0.836 |
| CYBRD1 | PGD | 0.836 |
| DYSF | SORL1 | 0.836 |
| FLII | TSPO | 0.836 |
| IMPA2 | TBXAS1 | 0.836 |
| LAPTM5 | S100A12 | 0.836 |
| PGD | PROS1 | 0.836 |
| PGD | TBXAS1 | 0.836 |
| ADA | NRD1 | 0.835 |
| ADA | SORL1 | 0.835 |
| DNMT1 | IFIT2 | 0.835 |
| DNMT1 | CTSB | 0.835 |
| GZMB | STAT1 | 0.835 |
| HERC5 | SAMD9 | 0.835 |
| HERC5 | STAT1 | 0.835 |
| HESX1 | IFIH1 | 0.835 |
| IFI6 | STAT1 | 0.835 |
| KCTD14 | SAMD9 | 0.835 |
| LAX1 | HK3 | 0.835 |
| SAMD9 | SIGLEC1 | 0.835 |
| STAT1 | GPAA1 | 0.835 |
| ACPP | PTAFR | 0.835 |
| CAT | DYSF | 0.835 |
| CETP | NRD1 | 0.835 |
| CTSB | NRD1 | 0.835 |
| CYBRD1 | S100A12 | 0.835 |
| DYSF | SLC12A9 | 0.835 |
| EMR1 | PTAFR | 0.835 |
| EMR1 | SORT1 | 0.835 |
| FLII | GPAA1 | 0.835 |
| FLII | PLP2 | 0.835 |
| HK3 | IMPA2 | 0.835 |
| LAPTM5 | RAB31 | 0.835 |
| LAPTM5 | RTN3 | 0.835 |
| NINJ2 | RTN3 | 0.835 |
| NRD1 | PYGL | 0.835 |
| NRD1 | S100A12 | 0.835 |
| PTAFR | PLP2 | 0.835 |
| PYGL | TBXAS1 | 0.835 |
| CHST12 | PROS1 | 0.834 |
| DDX60 | DHX58 | 0.834 |
| DNMT1 | CYBRD1 | 0.834 |
| DNMT1 | PYGL | 0.834 |
| DNMT1 | S100A12 | 0.834 |
| GZMB | RTN3 | 0.834 |
| GZMB | SORT1 | 0.834 |
| IFIH1 | IFIT3 | 0.834 |
| IFIT2 | GPAA1 | 0.834 |
| IFIT2 | LAPTM5 | 0.834 |
| IFIT3 | IFIT5 | 0.834 |
| IFIT3 | XAF1 | 0.834 |
| IFIT5 | OAS1 | 0.834 |
| LAX1 | NINJ2 | 0.834 |
| LAX1 | SORT1 | 0.834 |
| ACPP | PYGL | 0.834 |
| CAT | NRD1 | 0.834 |
| CAT | RAB31 | 0.834 |
| CTSB | PGD | 0.834 |
| DYSF | EMR1 | 0.834 |
| DYSF | PROS1 | 0.834 |
| DYSF | RTN3 | 0.834 |
| DYSF | S100A12 | 0.834 |
| EMR1 | NINJ2 | 0.834 |
| EMR1 | TWF2 | 0.834 |
| HK3 | STAT5B | 0.834 |
| HK3 | TNIP1 | 0.834 |
| PTAFR | PYGL | 0.834 |
| SORL1 | STAT5B | 0.834 |
| SORT1 | TNIP1 | 0.834 |
| ADA | PGD | 0.833 |
| CUL1 | DHX58 | 0.833 |
| DHX58 | EIF2AK2 | 0.833 |
| DHX58 | CETP | 0.833 |
| DHX58 | TALDO1 | 0.833 |
| DNMT1 | EMR1 | 0.833 |
| IFIT2 | TWF2 | 0.833 |
| IFIT3 | PARP12 | 0.833 |
| IFIT3 | SAMD9 | 0.833 |
| IFIT5 | OASL | 0.833 |
| LAX1 | CAT | 0.833 |
| OAS1 | SAMD9 | 0.833 |
| SAMD9 | TKT | 0.833 |
| ACAA1 | RAB31 | 0.833 |
| DOK3 | S100A12 | 0.833 |
| DYSF | IMPA2 | 0.833 |
| EMR1 | FLII | 0.833 |
| IMPA2 | TWF2 | 0.833 |
| PGD | PLP2 | 0.833 |
| PLP2 | RAB31 | 0.833 |
| PTAFR | RTN3 | 0.833 |
| PTAFR | TSPO | 0.833 |
| PYGL | TSPO | 0.833 |
| SORT1 | TALDO1 | 0.833 |
| TALDO1 | TSPO | 0.833 |
| ADA | NINJ2 | 0.832 |
| CHST12 | GZMB | 0.832 |
| CUL1 | GZMB | 0.832 |
| DHX58 | ISG20 | 0.832 |
| DNMT1 | PROS1 | 0.832 |
| HESX1 | IFIT5 | 0.832 |
| IFIT2 | OAS1 | 0.832 |
| ISG20 | KCTD14 | 0.832 |
| JUP | KCTD14 | 0.832 |
| OAS3 | SAMD9 | 0.832 |
| OAS3 | STAT1 | 0.832 |
| SAMD9 | RTN3 | 0.832 |
| ACAA1 | PGD | 0.832 |
| CAT | CETP | 0.832 |
| CAT | RTN3 | 0.832 |
| CETP | S100A12 | 0.832 |
| CTSB | HK3 | 0.832 |
| CYBRD1 | DOK3 | 0.832 |
| DOK3 | RTN3 | 0.832 |
| DYSF | PLP2 | 0.832 |
| DYSF | RAB31 | 0.832 |
| DYSF | STAT5B | 0.832 |
| DYSF | TSPO | 0.832 |
| FLII | NINJ2 | 0.832 |
| FLII | RTN3 | 0.832 |
| FLII | SORT1 | 0.832 |
| FLII | STAT5B | 0.832 |
| HK3 | PLP2 | 0.832 |
| LAPTM5 | TSPO | 0.832 |
| NINJ2 | RAB31 | 0.832 |
| NINJ2 | S100A12 | 0.832 |
| PGD | SORT1 | 0.832 |
| PTAFR | PROS1 | 0.832 |
| PTAFR | SORL1 | 0.832 |
| RTN3 | TWF2 | 0.832 |
| STAT1 | ADA | 0.831 |
| ADA | PLP2 | 0.831 |
| ISG20 | CHST12 | 0.831 |
| IFIT5 | DDX60 | 0.831 |
| ISG20 | DNMT1 | 0.831 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| DNMT1 | LAPTM5 | 0.831 |
| SAMD9 | LAPTM5 | 0.831 |
| ACAA1 | PROS1 | 0.831 |
| ACPP | EMR1 | 0.831 |
| CETP | TSPO | 0.831 |
| CYBRD1 | FLII | 0.831 |
| EMR1 | LAPTM5 | 0.831 |
| HK3 | TBXAS1 | 0.831 |
| NINJ2 | NRD1 | 0.831 |
| NINJ2 | PYGL | 0.831 |
| PGD | S100A12 | 0.831 |
| PLP2 | TKT | 0.831 |
| RTN3 | RAB31 | 0.831 |
| ADA | DYSF | 0.83 |
| ADA | HK3 | 0.83 |
| STAT1 | CHST12 | 0.83 |
| IFIH1 | CUL1 | 0.83 |
| KCTD14 | DHX58 | 0.83 |
| DNMT1 | RTN3 | 0.83 |
| IFIT2 | HERC5 | 0.83 |
| ISG20 | IFIH1 | 0.83 |
| IFIT2 | TNIP1 | 0.83 |
| LAX1 | CYBRD1 | 0.83 |
| LAX1 | RTN3 | 0.83 |
| SAMD9 | OASL | 0.83 |
| XAF1 | PARP12 | 0.83 |
| STAT1 | DOK3 | 0.83 |
| STAT1 | NRD1 | 0.83 |
| STAT1 | PROS1 | 0.83 |
| ACAA1 | DYSF | 0.83 |
| ACAA1 | S100A12 | 0.83 |
| CAT | HK3 | 0.83 |
| CAT | LAPTM5 | 0.83 |
| CETP | CTSB | 0.83 |
| CETP | DYSF | 0.83 |
| CETP | IMPA2 | 0.83 |
| CTSB | TBXAS1 | 0.83 |
| CTSB | TWF2 | 0.83 |
| CYBRD1 | TBXAS1 | 0.83 |
| CYBRD1 | TWF2 | 0.83 |
| IMPA2 | FLII | 0.83 |
| HK3 | NRD1 | 0.83 |
| HK3 | PROS1 | 0.83 |
| HK3 | SLC12A9 | 0.83 |
| HK3 | TWF2 | 0.83 |
| IMPA2 | PROS1 | 0.83 |
| IMPA2 | PTAFR | 0.83 |
| IMPA2 | TALDO1 | 0.83 |
| PYGL | TWF2 | 0.83 |
| RAB31 | S100A12 | 0.83 |
| SORT1 | TKT | 0.83 |
| SORT1 | TWF2 | 0.83 |
| ADA | CYBRD1 | 0.829 |
| LAX1 | CUL1 | 0.829 |
| OASL | DHX58 | 0.829 |
| DHX58 | CAT | 0.829 |
| IFIT2 | EIF2AK2 | 0.829 |
| KCTD14 | IFIH1 | 0.829 |
| STAT1 | RTN3 | 0.829 |
| ACAA1 | PLP2 | 0.829 |
| CAT | TWF2 | 0.829 |
| CETP | RTN3 | 0.829 |
| CTSB | CYBRD1 | 0.829 |
| CTSB | PYGL | 0.829 |
| IMPA2 | TKT | 0.829 |
| NRD1 | TALDO1 | 0.829 |
| PLP2 | TNIP1 | 0.829 |
| TKT | TSPO | 0.829 |
| ISG20 | ADA | 0.828 |
| ADA | CAT | 0.828 |
| ADA | PROS1 | 0.828 |
| SAMD9 | DDX60 | 0.828 |
| IFIT5 | DHX58 | 0.828 |
| XAF1 | DHX58 | 0.828 |
| STAT1 | DNMT1 | 0.828 |
| ISG20 | GZMB | 0.828 |
| LAX1 | GZMB | 0.828 |
| KCTD14 | HESX1 | 0.828 |
| OASL | IFIT2 | 0.828 |
| LAX1 | ISG20 | 0.828 |
| PARP12 | ISG20 | 0.828 |
| SAMD9 | ISG20 | 0.828 |
| STAT1 | KCTD14 | 0.828 |
| STAT1 | OAS1 | 0.828 |
| STAT1 | CAT | 0.828 |
| ACAA1 | EMR1 | 0.828 |
| ACPP | DOK3 | 0.828 |
| CAT | PTAFR | 0.828 |
| CTSB | NINJ2 | 0.828 |
| CTSB | S100A12 | 0.828 |
| CTSB | TALDO1 | 0.828 |
| CYBRD1 | NINJ2 | 0.828 |
| CYBRD1 | NRD1 | 0.828 |
| DOK3 | IMPA2 | 0.828 |
| DOK3 | SLC12A9 | 0.828 |
| DOK3 | STAT5B | 0.828 |
| DYSF | TALDO1 | 0.828 |
| DYSF | TWF2 | 0.828 |
| PGD | RTN3 | 0.828 |
| PLP2 | TALDO1 | 0.828 |
| PYGL | RTN3 | 0.828 |
| TALDO1 | TBXAS1 | 0.828 |
| ADA | RAB31 | 0.827 |
| IFIT2 | DDX60 | 0.827 |
| DHX58 | PROS1 | 0.827 |
| STAT1 | EIF2AK2 | 0.827 |
| PARP12 | IFIH1 | 0.827 |
| XAF1 | IFIH1 | 0.827 |
| SAMD9 | FLII | 0.827 |
| ACAA1 | TALDO1 | 0.827 |
| CETP | HK3 | 0.827 |
| CETP | NINJ2 | 0.827 |
| CETP | PGD | 0.827 |
| CETP | PTAFR | 0.827 |
| CETP | RAB31 | 0.827 |
| LAPTM5 | PLP2 | 0.827 |
| PTAFR | S100A12 | 0.827 |
| ADA | TALDO1 | 0.826 |
| SAMD9 | EIF2AK2 | 0.826 |
| HERC5 | IFIT5 | 0.826 |
| OAS3 | IFIT2 | 0.826 |
| STAT1 | TKT | 0.826 |
| CAT | DOK3 | 0.826 |
| CAT | S100A12 | 0.826 |
| CETP | CYBRD1 | 0.826 |
| CETP | FLII | 0.826 |
| CETP | PLP2 | 0.826 |
| CYBRD1 | PTAFR | 0.826 |
| DOK3 | PYGL | 0.826 |
| DYSF | PTAFR | 0.826 |
| HK3 | RAB31 | 0.826 |
| HK3 | TSPO | 0.826 |
| NRD1 | TNIP1 | 0.826 |
| PGD | TNIP1 | 0.826 |
| PGD | TSPO | 0.826 |
| PTAFR | STAT5B | 0.826 |
| PTAFR | TBXAS1 | 0.826 |
| PYGL | S100A12 | 0.826 |
| ADA | RTN3 | 0.825 |
| CUL1 | PROS1 | 0.825 |
| HESX1 | DHX58 | 0.825 |
| DHX58 | CYBRD1 | 0.825 |
| DNMT1 | HK3 | 0.825 |
| PARP12 | HESX1 | 0.825 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| STAT1 | HESX1 | 0.825 |
| ISG20 | CYBRD1 | 0.825 |
| STAT1 | TNIP1 | 0.825 |
| ACAA1 | TKT | 0.825 |
| CTSB | DYSF | 0.825 |
| CYBRD1 | HK3 | 0.825 |
| EMR1 | HK3 | 0.825 |
| FLII | TBXAS1 | 0.825 |
| LAPTM5 | PYGL | 0.825 |
| NINJ2 | TBXAS1 | 0.825 |
| PGD | RAB31 | 0.825 |
| PLP2 | PROS1 | 0.825 |
| PROS1 | TSPO | 0.825 |
| PTAFR | RAB31 | 0.825 |
| PTAFR | SLC12A9 | 0.825 |
| RAB31 | TALDO1 | 0.825 |
| TBXAS1 | TKT | 0.825 |
| CUL1 | ADA | 0.824 |
| ADA | PYGL | 0.824 |
| IFIT2 | DHX58 | 0.824 |
| EIF2AK2 | IFIT5 | 0.824 |
| IFIT3 | IFIT2 | 0.824 |
| STAT1 | IFIT3 | 0.824 |
| LAX1 | PROS1 | 0.824 |
| SAMD9 | CETP | 0.824 |
| STAT1 | TWF2 | 0.824 |
| CAT | CYBRD1 | 0.824 |
| CTSB | PROS1 | 0.824 |
| CYBRD1 | LAPTM5 | 0.824 |
| DOK3 | RAB31 | 0.824 |
| DYSF | LAPTM5 | 0.824 |
| FLII | PYGL | 0.824 |
| HK3 | S100A12 | 0.824 |
| HK3 | TKT | 0.824 |
| LAPTM5 | SORT1 | 0.824 |
| LAPTM5 | TALDO1 | 0.824 |
| LAPTM5 | TBXAS1 | 0.824 |
| PTAFR | SORT1 | 0.824 |
| PYGL | TNIP1 | 0.824 |
| ISG20 | CUL1 | 0.823 |
| PARP12 | CUL1 | 0.823 |
| CUL1 | CYBRD1 | 0.823 |
| ACAA1 | TNIP1 | 0.823 |
| CAT | TKT | 0.823 |
| DOK3 | TBXAS1 | 0.823 |
| DYSF | SORT1 | 0.823 |
| FLII | HK3 | 0.823 |
| NRD1 | PTAFR | 0.823 |
| PROS1 | RTN3 | 0.823 |
| PYGL | RAB31 | 0.823 |
| RAB31 | TKT | 0.823 |
| STAT5B | TNIP1 | 0.823 |
| GZMB | ADA | 0.822 |
| LAX1 | CHST12 | 0.822 |
| IFIT2 | CUL1 | 0.822 |
| KCTD14 | CUL1 | 0.822 |
| SAMD9 | DHX58 | 0.822 |
| JUP | DNMT1 | 0.822 |
| ISG20 | IFIT2 | 0.822 |
| XAF1 | IFIT5 | 0.822 |
| SAMD9 | TNIP1 | 0.822 |
| STAT1 | CYBRD1 | 0.822 |
| CAT | TALDO1 | 0.822 |
| CETP | TNIP1 | 0.822 |
| CTSB | FLII | 0.822 |
| CYBRD1 | RAB31 | 0.822 |
| FLII | PROS1 | 0.822 |
| NRD1 | PROS1 | 0.822 |
| PYGL | TKT | 0.822 |
| BXAS1 | TTWF2 | 0.822 |
| ADA | S100A12 | 0.821 |
| SAMD9 | HESX1 | 0.821 |
| SAMD9 | IFIH1 | 0.821 |
| STAT1 | CETP | 0.821 |
| STAT1 | FLII | 0.821 |
| CAT | PYGL | 0.821 |
| CTSB | TKT | 0.821 |
| RTN3 | CYBRD1 | 0.821 |
| DOK3 | PROS1 | 0.821 |
| DYSF | PYGL | 0.821 |
| RTN3 | TKT | 0.821 |
| ADA | SORT1 | 0.82 |
| PARP12 | DHX58 | 0.82 |
| ISG20 | IFIT5 | 0.82 |
| ACAA1 | FLII | 0.82 |
| ACAA1 | LAPTM5 | 0.82 |
| CTSB | DOK3 | 0.82 |
| CYBRD1 | TALDO1 | 0.82 |
| DYSF | HK3 | 0.82 |
| DYSF | TKT | 0.82 |
| DYSF | TNIP1 | 0.82 |
| HK3 | LAPTM5 | 0.82 |
| NINJ2 | PLP2 | 0.82 |
| NINJ2 | PROS1 | 0.82 |
| PGD | PTAFR | 0.82 |
| PGD | PYGL | 0.82 |
| PROS1 | S100A12 | 0.82 |
| PROS1 | TNIP1 | 0.82 |
| PYGL | TALDO1 | 0.82 |
| ADA | LAPTM5 | 0.819 |
| CUL1 | CHST12 | 0.819 |
| SAMD9 | CUL1 | 0.819 |
| STAT1 | DDX60 | 0.819 |
| CETP | PYGL | 0.819 |
| PYGL | CYBRD1 | 0.819 |
| DOK3 | EMR1 | 0.819 |
| HK3 | SORT1 | 0.819 |
| RTN3 | TALDO1 | 0.819 |
| DNMT1 | GZMB | 0.818 |
| IFIT2 | HESX1 | 0.818 |
| XAF1 | IFIT2 | 0.818 |
| XAF1 | SAMD9 | 0.818 |
| CTSB | CAT | 0.818 |
| CETP | TKT | 0.818 |
| CTSB | PTAFR | 0.818 |
| TNIP1 | CTSB | 0.818 |
| DOK3 | NRD1 | 0.818 |
| DOK3 | SORT1 | 0.818 |
| DOK3 | TSPO | 0.818 |
| HK3 | TALDO1 | 0.818 |
| LAPTM5 | PGD | 0.818 |
| PGD | TALDO1 | 0.818 |
| PROS1 | PYGL | 0.818 |
| PTAFR | TWF2 | 0.818 |
| TALDO1 | TNIP1 | 0.818 |
| ADA | DOK3 | 0.817 |
| DNMT1 | CUL1 | 0.817 |
| IFIT5 | IFIH1 | 0.817 |
| PARP12 | IFIT5 | 0.817 |
| SAMD9 | PARP12 | 0.817 |
| STAT1 | LAPTM5 | 0.817 |
| ACAA1 | HK3 | 0.817 |
| ACAA1 | TWF2 | 0.817 |
| CAT | PROS1 | 0.817 |
| FLII | PGD | 0.817 |
| HK3 | PYGL | 0.817 |
| LAPTM5 | TNIP1 | 0.817 |
| NINJ2 | TKT | 0.817 |
| TKT | TNIP1 | 0.817 |
| CHST12 | ADA | 0.816 |
| IFIT5 | CUL1 | 0.816 |
| PARP12 | IFIT2 | 0.816 |
| CAT | NINJ2 | 0.816 |
| DYSF | FLII | 0.816 |

SUPPLEMENTAL TABLE 4-continued

Mean Area Under the Curve (AUC) for 2-Gene Combinations. Each 2-gene set was taken from the set of genes found by iterated greedy forward search (the pool of 71 genes). The AUC is the mean AUC across the discovery datasets. Only shown are those two-gene combinations with a mean AUC ≥ 0.80.

| Gene 1 | Gene 2 | AUC |
|---|---|---|
| PGD | TWF2 | 0.816 |
| PROS1 | TKT | 0.816 |
| PTAFR | TNIP1 | 0.816 |
| TKT | TWF2 | 0.816 |
| STAT1 | DHX58 | 0.815 |
| DNMT1 | NINJ2 | 0.815 |
| KCTD14 | IFIT2 | 0.815 |
| ACAA1 | NINJ2 | 0.815 |
| ACAA1 | PTAFR | 0.815 |
| CYBRD1 | PROS1 | 0.815 |
| DYSF | DOK3 | 0.815 |
| HK3 | PTAFR | 0.815 |
| NINJ2 | PTAFR | 0.815 |
| NINJ2 | TNIP1 | 0.815 |
| PROS1 | RAB31 | 0.815 |
| CETP | DOK3 | 0.814 |
| CTSB | LAPTM5 | 0.814 |
| TKT | CYBRD1 | 0.814 |
| FLII | TNIP1 | 0.814 |
| LAPTM5 | NINJ2 | 0.814 |
| PLP2 | TWF2 | 0.814 |
| PROS1 | TWF2 | 0.814 |
| CETP | LAPTM5 | 0.813 |
| CETP | TALDO1 | 0.813 |
| DOK3 | NINJ2 | 0.813 |
| DYSF | PGD | 0.813 |
| TNIP1 | TWF2 | 0.813 |
| DOK3 | PLP2 | 0.812 |
| FLII | TALDO1 | 0.812 |
| LAPTM5 | PROS1 | 0.812 |
| NINJ2 | TALDO1 | 0.812 |
| PGD | TKT | 0.812 |
| TWF2 | TALDO1 | 0.812 |
| SAMD9 | IFIT2 | 0.811 |
| STAT1 | ISG20 | 0.811 |
| XAF1 | STAT1 | 0.811 |
| CETP | TWF2 | 0.811 |
| HK3 | PGD | 0.811 |
| PTAFR | TALDO1 | 0.811 |
| PARP12 | STAT1 | 0.81 |
| ACAA1 | DOK3 | 0.81 |
| FLII | PTAFR | 0.81 |
| TKT | LAPTM5 | 0.81 |
| DNMT1 | DOK3 | 0.809 |
| PTAFR | LAPTM5 | 0.809 |
| PTAFR | TKT | 0.809 |
| STAT1 | IFIT5 | 0.808 |
| TWF2 | LAPTM5 | 0.808 |
| PROS1 | TALDO1 | 0.808 |
| DNMT1 | SORT1 | 0.807 |
| ADA | LAX1 | 0.806 |
| DOK3 | HK3 | 0.806 |
| SAMD9 | IFIT5 | 0.805 |
| DOK3 | PTAFR | 0.805 |
| FLII | TKT | 0.805 |
| DNMT1 | CHST12 | 0.804 |
| IFIT2 | IFIH1 | 0.804 |
| NINJ2 | TWF2 | 0.804 |
| STAT1 | IFIH1 | 0.803 |
| IFIT5 | IFIT2 | 0.803 |
| CETP | PROS1 | 0.802 |
| DOK3 | TKT | 0.802 |
| FLII | TWF2 | 0.802 |
| STAT1 | IFIT2 | 0.801 |
| SAMD9 | STAT1 | 0.8 |
| DOK3 | TWF2 | 0.8 |

REFERENCES

1. Ferrer, R., et al. Empiric antibiotic treatment reduces mortality in severe sepsis and septic shock from the first hour: results from a guideline-based performance improvement program*. *Crit Care Med* 42, 1749-1755 (2014).

2. Fridkin, S., et al. Vital signs: improving antibiotic use among hospitalized patients. *MMWR Morb Mortal Wkly Rep* 63, 194-200 (2014).

3. Grijalva, C. G., Nuorti, J. P. & Griffin, M. R. Antibiotic prescription rates for acute respiratory tract infections in US ambulatory settings. *JAMA* 302, 758-766 (2009).

4. Andrews, J. High rates of enteric fever diagnosis and low burden of disease in rural Nepal. in *9th International Conference on Typhoid and Invasive NTS Disease* (Bali, Indonesia, 2015).

5. *National strategy and action plan for combating antibiotic resistant bacteria*, (New York: Nova Publishers, 2015).

6. Liesenfeld, O., Lehman, L., Hunfeld, K. P. & Kost, G. Molecular diagnosis of sepsis: New aspects and recent developments. *Eur J Microbial Immunol (Bp)* 4, 1-25 (2014).

7. Sweeney, T. E., Shidham, A., Wong, H. R. & Khatri, P. A comprehensive time-course-based multicohort analysis of sepsis and sterile inflammation reveals a robust diagnostic gene set. *Sci Transl Med* 7, 287ra271 (2015).

8. Sweeney, T. E. & Khatri, P. Comprehensive Validation of the FAIM3:PLAC8 Ratio in Time-matched Public Gene Expression Data. *Am J Respir Crit Care Med* 192, 1260-1261 (2015).

9. McHugh, L., et al. A Molecular Host Response Assay to Discriminate Between Sepsis and Infection-Negative Systemic Inflammation in Critically Ill Patients: Discovery and Validation in Independent Cohorts. *PLoS Med* 12, e1001916 (2015).

10. Scicluna, B. P., et al. A Molecular Biomarker to Diagnose Community-acquired Pneumonia on Intensive Care Unit Admission. *Am J Respir Crit Care Med* (2015).

11. Hu, X., Yu, J., Crosby, S. D. & Storch, G. A. Gene expression profiles in febrile children with defined viral and bacterial infection. *Proc Natl Acad Sci USA* 110, 12792-12797 (2013).

12. Zaas, A. K., et al. A host-based rt-PCR gene expression signature to identify acute respiratory viral infection. *Sci Transl Med* 5, 203ra126 (2013).

13. Suarez, N. M., et al. Superiority of Transcriptional Profiling Over Procalcitonin for Distinguishing Bacterial From Viral Lower Respiratory Tract Infections in Hospitalized Adults. *J Infect Dis* (2015).

14. Tsalik, E. L., et al. Host gene expression classifiers diagnose acute respiratory illness etiology. *Sci Transl Med* 8, 322ra311 (2016).

15. Andres-Terre, M., et al. Integrated, Multi-cohort Analysis Identifies Conserved Transcriptional Signatures across Multiple Respiratory Viruses. *Immunity* 43, 1199-1211 (2015).

16. Sweeney, T. E., Braviak, L., Tato, C. M. & Khatri, P. Multi-Cohort Analysis of Genome-Wide Expression for Diagnosis of Pulmonary Tuberculosis. *Lancet Resp Med* (Accepted, January 2016).

17. Sweeney, T. E. & Khatri, P. Benchmarking sepsis gene expression diagnostics using public data. *Under Review*, January 2016.

18. Shanley, T. P., et al. Genome-level longitudinal expression of signaling pathways and gene networks in pediatric septic shock. *Mol Med* 13, 495-508 (2007).

19. Wong, H. R., et al. Genome-level expression profiles in pediatric septic shock indicate a role for altered zinc homeostasis in poor outcome. *Physiol Genomics* 30, 146-155 (2007).

20. Cvijanovich, N., et al. Validating the genomic signature of pediatric septic shock. *Physiol Genomics* 34, 127-134 (2008).

21. Wong, H. R., et al. Genomic expression profiling across the pediatric systemic inflammatory response syndrome, sepsis, and septic shock spectrum. *Crit Care Med* 37, 1558-1566 (2009).

22. Wong, H. R., et al. Interleukin-27 is a novel candidate diagnostic biomarker for bacterial infection in critically ill children. *Crit Care* 16, R213 (2012).

23. Ramilo, O., et al. Gene expression patterns in blood leukocytes discriminate patients with acute infections. *Blood* 109, 2066-2077 (2007).

24. Parnell, G., et al. Aberrant cell cycle and apoptotic changes characterise severe influenza A infection--a meta-analysis of genomic signatures in circulating leukocytes. *PLoS One* 6, e17186 (2011).

25. Parnell, G. P., et al. A distinct influenza infection signature in the blood transcriptome of patients with severe community-acquired pneumonia. *Crit Care* 16, R157 (2012).

26. Herberg, J. A., et al. Transcriptomic profiling in childhood H1N1/09 influenza reveals reduced expression of protein synthesis genes. *J Infect Dis* 208, 1664-1668 (2013).

27. Khatri, P., et al. A common rejection module (CRM) for acute rejection across multiple organs identifies novel therapeutics for organ transplantation. *J Exp Med* 210, 2205-2221 (2013).

28. Popper, S. J., et al. Gene transcript abundance profiles distinguish Kawasaki disease from adenovirus infection. *J Infect Dis* 200, 657-666 (2009).

29. Smith, C. L., et al. Identification of a human neonatal immune-metabolic network associated with bacterial infection. *Nat Commun* 5, 4649 (2014).

30. Almansa, R., et al. Critical COPD respiratory illness is linked to increased transcriptomic activity of neutrophil proteases genes. *BMC Res Notes* 5, 401 (2012).

31. Lee, M. N., et al. Common genetic variants modulate pathogen-sensing responses in human dendritic cells. *Science* 343, 1246980 (2014).

32. Johnson, W. E., Li, C. & Rabinovic, A. Adjusting batch effects in microarray expression data using empirical Bayes methods. *Biostatistics* 8, 118-127 (2007).

33. Zhai, Y., et al. Host Transcriptional Response to Influenza and Other Acute Respiratory Viral Infections--A Prospective Cohort Study. *PLoS Pathog* 11, e1004869 (2015).

34. Kwissa, M., et al. Dengue virus infection induces expansion of a CD14(+)CD16(+) monocyte population that stimulates plasmablast differentiation. *Cell Host Microbe* 16, 115-127 (2014).

35. Mejias, A., et al. Whole blood gene expression profiles to assess pathogenesis and disease severity in infants with respiratory syncytial virus infection. *PLoS Med* 10, e1001549 (2013).

36. Berdal, J. E., et al. Excessive innate immune response and mutant D222G/N in severe A (H1N1) pandemic influenza. *J infect* 63, 308-316 (2011).

37. Bermejo-Martin, J. F., et al. Host adaptive immunity deficiency in severe pandemic influenza. Crit Care 14, R167 (2010).

38. Zaas, A. K., et al. Gene expression signatures diagnose influenza and other symptomatic respiratory viral infections in humans. *Cell Host Microbe* 6, 207-217 (2009).

39. van de Weg, C. A., et al. Time since onset of disease and individual clinical markers associate with transcriptional changes in uncomplicated dengue. PLoS Negl Trop Dis 9, e0003522 (2015).

40. Conejero, L., et al. The Blood Transcriptome of Experimental Melioidosis Reflects Disease Severity and Shows Considerable Similarity with the Human Disease. *J Immunol* 195, 3248-3261 (2015).

41. Cazalis, M. A., et al. Early and dynamic changes in gene expression in septic shock patients: a genome-wide approach. *Intensive Care Med Exp* 2, 20 (2014).

42. Lill, M., et al. Peripheral blood RNA gene expression profiling in patients with bacterial meningitis. *Front Neurosci* 7, 33 (2013).

43. Ahn, S. H., et al. Gene expression-based classifiers identify *Staphylococcus aureus* infection in mice and humans. *PLoS One* 8, e48979 (2013).

44. Thuny, F., et al. The gene expression analysis of blood reveals S100A11 and AQP9 as potential biomarkers of infective endocarditis. *PLoS One* 7, e31490 (2012).

45. Sutherland, A., et al. Development and validation of a novel molecular biomarker diagnostic test for the early detection of sepsis. *Crit Care* 15, R149 (2011).

46. Berry, M. P., et al. An interferon-inducible neutrophil-driven blood transcriptional signature in human tuberculosis. *Nature* 466, 973-977 (2010).

47. Pankla, R., et al. Genomic transcriptional profiling identifies a candidate blood biomarker signature for the diagnosis of septicemic melioidosis. *Genome Biol* 10, R127 (2009).

48. Irwin, A. D., et al. Novel biomarker combination improves the diagnosis of serious bacterial infections in Malawian children. *BMC Med Genomics* 5, 13 (2012).

49. Bloom, C. I., et al. Transcriptional blood signatures distinguish pulmonary tuberculosis, pulmonary sarcoidosis, pneumonias and lung cancers. *PLoS One* 8, e70630 (2013).

50. Ardura, M. I., et al. Enhanced monocyte response and decreased central memory T cells in children with invasive *Staphylococcus aureus* infections. *PLoS One* 4, e5446 (2009).

51. Liu, K., Chen, L., Kaur, R. & Pichichero, M. Transcriptome signature in young children with acute otitis media due to *Streptococcus pneumoniae*. *Microbes Infect* 14, 600-609 (2012).

52. Ioannidis, I., et al. Plasticity and virus specificity of the airway epithelial cell immune response during respiratory virus infection. *J Virol* 86, 5422-5436 (2012).

53. Popper, S. J., et al. Temporal dynamics of the transcriptional response to dengue virus infection in Nicaraguan children. *PLoS Negl Trop Dis* 6, e1966 (2012).

54. Brand, H. K., et al. Olfactomedin 4 Serves as a Marker for Disease Severity in Pediatric Respiratory Syncytial Virus (RSV) Infection. *PLoS One* 10, e0131927 (2015).

55. Wacker, C., Prkno, A., Brunkhorst, F. M. & Schlattmann, P. Procalcitonin as a diagnostic marker for sepsis: a systematic review and meta-analysis. *Lancet Infect Dis* 13, 426-435 (2013).

56. Kulkarni, M. M. Digital multiplexed gene expression analysis using the NanoString nCounter system. *Curr Protoc Mol Biol Chapter* 25, Unit25B.10 (2011).

57. Tsalik, E. L., et al. Potential Cost-effectiveness of Early Identification of Hospital-acquired Infection in Critically Ill Patients. *Ann Am Thorac Soc* (2015).

58. Gilbert, D. N. Procalcitonin as a biomarker in respiratory tract infection. *Clin Infect Dis* 52 Suppl 4, S346-350 (2011).

59. Oved, K., et al. A novel host-proteome signature for distinguishing between acute bacterial and viral infections. *PLoS One* 10, e0120012 (2015).

60. Valim, C., et al. Responses to Bacteria, Virus, and Malaria Distinguish the Etiology of Pediatric Clinical Pneumonia. *Am J Respir Crit Care Med* 193, 448-459 (2016).

61. Tolfvenstam, T., et al. Characterization of early host responses in adults with dengue disease. *BMC Infect Dis* 11, 209 (2011).

62. Vanden Berghe, T., Linkermann, A., Jouan-Lanhouet, S., Walczak, H. & Vandenabeele, P. Regulated necrosis: the expanding network of non-apoptotic cell death pathways. *Nat Rev Mol Cell Biol* 15, 135-147 (2014).

63. Ashida, H., et al. A bacterial E3 ubiquitin ligase IpaH9.8 targets NEMO/IKKgamma to dampen the host NF-kappaB-mediated inflammatory response. *Nat Cell Biol* 12, 66-73; sup pp 61-69 (2010).

64. Zhu, M., et al. Negative regulation of lymphocyte activation by the adaptor protein LAX. *J Immunol* 174, 5612-5619 (2005).

65. Federzoni, E. A., et al. PU.1 is linking the glycolytic enzyme HK3 in neutrophil differentiation and survival of APL cells. *Blood* 119, 4963-4970 (2012).

66. Benjamini, Y. & Hochberg, Y. Controlling the false discovery rate: a practical and powerful approach to multiple testing. *Journal of the Royal Statistical Society, Series B* 57, 289-300 (1995).

67. Kester, A. D. & Buntinx, F. Meta-analysis of ROC curves. *Med Decis Making* 20, 430-439 (2000).

While the preferred embodiments of the invention have been illustrated and described, it will be appreciated that various changes can be made therein without departing from the spirit and scope of the invention.

What is claimed is:

1. A method for treating an infection in a patient, comprising:
    (a) identifying a patient that has an infection as having either a bacterial infection or a viral infection based on a score calculated using the expression levels of a set of biomarkers in a biological sample from the patient, wherein the set of biomarkers comprises transcripts of: CTSB and JUP;
    (b) administering an antibiotic to the patient if the patient is identified as having a bacterial infection or administering an antiviral agent to the patient if the patient is identified as having a viral infection.

2. The method of claim 1, wherein the method comprises: (a) identifying a patient that has an infection as having a bacterial infection based on the calculated score of the set of biomarkers; and (b) administering an antibiotic to the patient.

3. The method of claim 1, wherein the method comprises: (a) identifying a patient that has an infection as having a viral infection based on the calculated score of the set of biomarkers; and (b) administering an anti-viral agent to the patient.

4. The method of claim 1, wherein the set of biomarkers contains up to 30 biomarkers.

5. The method of claim 1, wherein the set of biomarkers contains at least 30 biomarkers.

6. The method of claim 1, wherein the biological sample comprises blood, blood cells, or a respiratory secretion.

7. The method of claim 6, wherein the biological sample comprises whole blood or peripheral blood mononucleated cells (PBMCs).

8. The method of claim 1, wherein the expression levels of the transcripts are measured by RT-PCR or isothermal amplification.

9. The method of claim 1, wherein step (a) comprises identifying the patient as having either a bacterial infection or a viral infection based on the calculated score using the level of expression of CTSB and JUP, relative to time-matched reference values for infected or non-infected subjects.

* * * * *